(12) United States Patent
Yang et al.

(10) Patent No.: US 11,738,042 B2
(45) Date of Patent: Aug. 29, 2023

(54) COMPOSITIONS AND METHODS FOR PROMOTING BONE REGENERATION

(71) Applicant: The Penn State Research Foundation, University Park, PA (US)

(72) Inventors: Jian Yang, State College, PA (US); Chuying Ma, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 924 days.

(21) Appl. No.: 16/537,303

(22) Filed: Aug. 9, 2019

(65) Prior Publication Data

US 2020/0093770 A1 Mar. 26, 2020

Related U.S. Application Data

(60) Provisional application No. 62/703,949, filed on Jul. 27, 2018.

(51) Int. Cl.
| | |
|---|---|
| *C08G 63/692* | (2006.01) |
| *A61K 35/28* | (2015.01) |
| *A61K 31/225* | (2006.01) |
| *A61K 31/197* | (2006.01) |

(Continued)

(52) U.S. Cl.
CPC .............. *A61K 31/80* (2013.01); *C08G 18/28* (2013.01); *C08G 18/66* (2013.01); *C08G 63/6924* (2013.01); *C08G 18/64* (2013.01)

(58) Field of Classification Search
CPC ........ A61K 31/80; C08G 18/28; C08G 18/66; C08G 63/6924
See application file for complete search history.

(56) References Cited

U.S. PATENT DOCUMENTS

| 4,595,713 A * | 6/1986 | St. John ................. A61L 27/18 |
| | | 623/23.72 |
| 2012/0178684 A1 | 7/2012 | Liu et al. |

(Continued)

FOREIGN PATENT DOCUMENTS

| WO | 2013059089 A1 | 4/2013 |
| WO | 2018107049 A1 | 6/2018 |

OTHER PUBLICATIONS

International Search Report and Written Opinion issued for Application No. PCT/US2019/045997, dated Dec. 2, 2019.

(Continued)

*Primary Examiner* — Tae H Yoon
(74) *Attorney, Agent, or Firm* — Meunier Carlin & Curfman LLC

(57) ABSTRACT

This invention relates to compositions and methods for promoting and/or accelerating bone regeneration, repair, and/or healing and, in particular, to compositions and methods of promoting bone regeneration, growth, repair, and/or healing using graft or scaffold materials. In exemplary embodiments, the disclosed compositions may be used to promote and/or accelerate bone regeneration by delivering a composition to a bone site, the composition comprising (a) a citrate component, (b) a phosphate component, and, optionally, (c) a particulate inorganic material. The citrate component and/or phosphate component is advantageously released from the composition at the bone site. The released citrate component may function to increase alkaline phosphatase activity and/or expression at the bone site, and the increased alkaline phosphatase activity and/or expression may release the phosphate component. The composition may be delivered in various forms, e.g., as a biodegradable scaffold.

18 Claims, 14 Drawing Sheets

(51) Int. Cl.
*A61K 31/661* (2006.01)
*A61K 33/42* (2006.01)
*A61K 33/06* (2006.01)
*A61K 35/32* (2015.01)
*C08G 18/00* (2006.01)
*A61K 31/194* (2006.01)
*A61K 31/80* (2006.01)
*C08G 18/66* (2006.01)
*C08G 18/28* (2006.01)
*C08G 18/64* (2006.01)

(56) References Cited

U.S. PATENT DOCUMENTS

| | | |
|---|---|---|
| 2013/0039990 A1 | 2/2013 | Xu et al. |
| 2014/0155516 A1 | 6/2014 | Ameer et al. |
| 2017/0080125 A1 | 3/2017 | Yang |

OTHER PUBLICATIONS

International Preliminary Report on Patentability, in connection to PCT/US2019/045997, dated Feb. 11, 2021.
Ma, Chuying, et al. "Citrate chemistry and biology for biomaterials design." Biomaterials 178 (2018): 383-400.
Morochnik, Simona, et al. "A thermoresponsive, citrate-based macromolecule for bone regenerative engineering." Journal of Biomedical Materials Research Part A 106.6 (2018): 1743-1752.
Extended European Search Report issued for Application No. 19841740.4, dated Feb. 8, 2022.

* cited by examiner

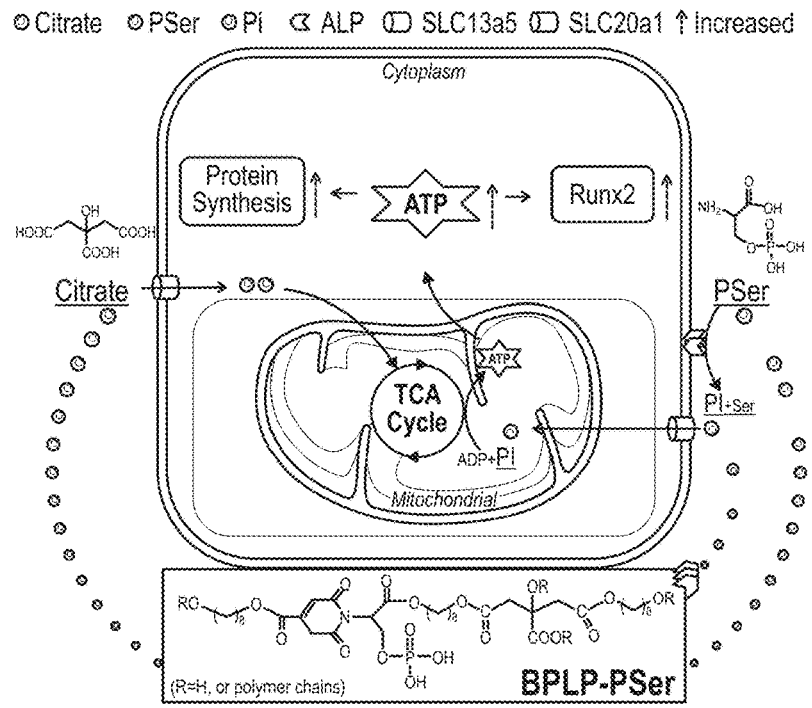
Fig. 1
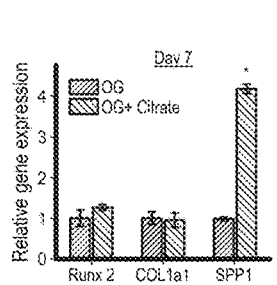
Fig. 2A
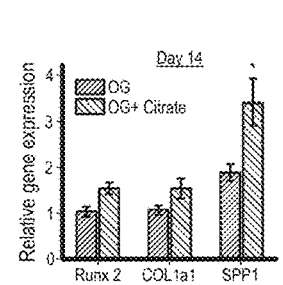
Fig. 2B
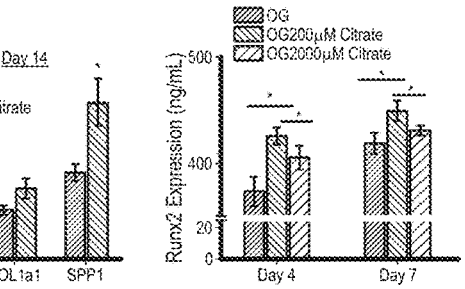
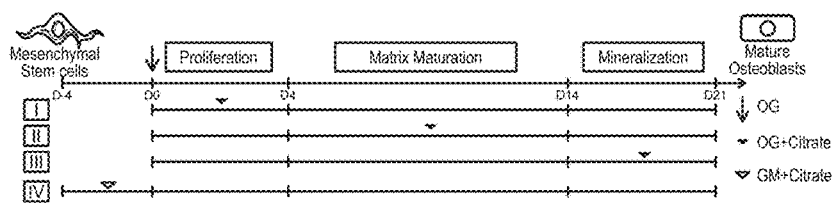
Fig. 2C
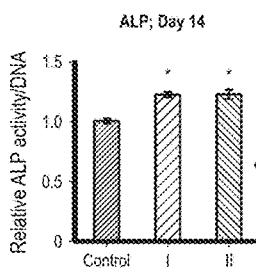
Fig. 2D
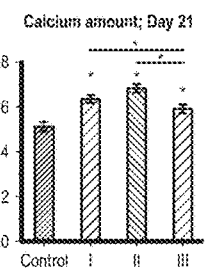
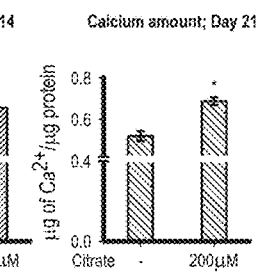
Fig. 2E

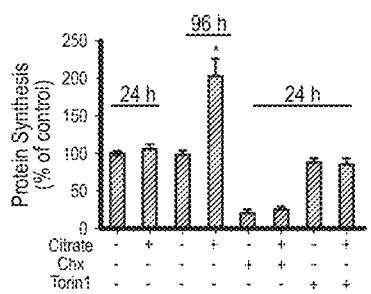 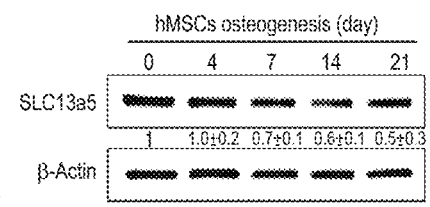 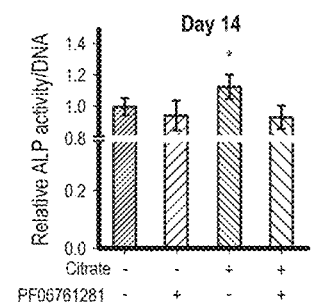
Fig. 3A Fig. 3B Fig. 3C
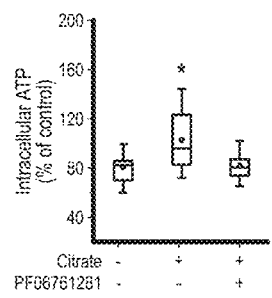 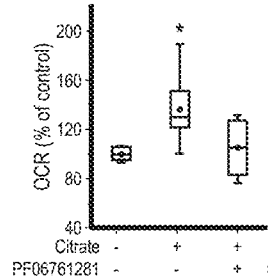 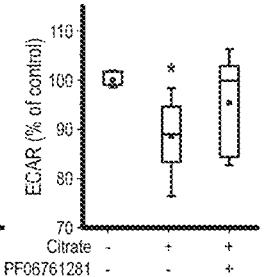 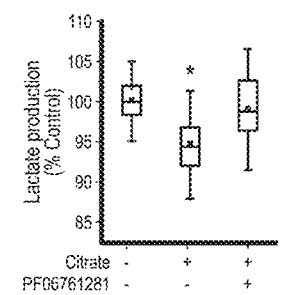
Fig. 3D Fig. 3E Fig. 3F Fig. 3G
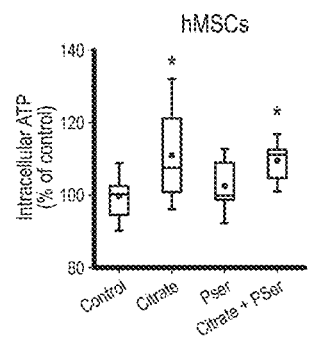 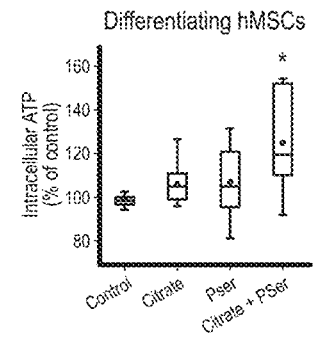 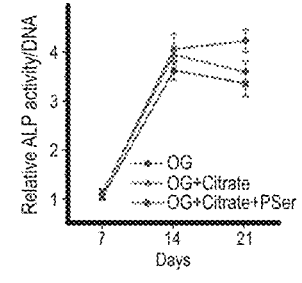
Fig. 3H Fig. 3I Fig. 3J
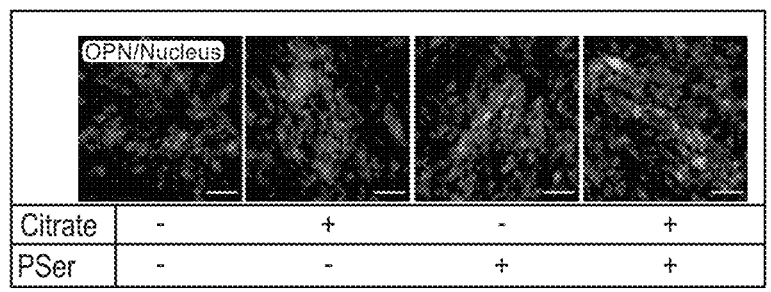
Fig. 3K

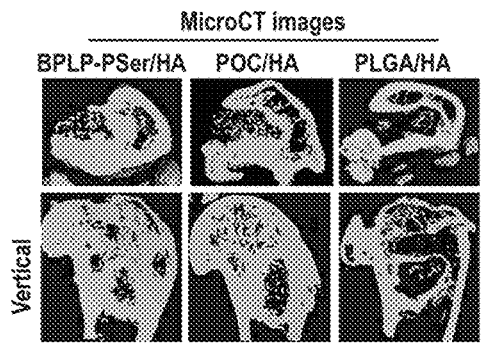
Fig. 6A
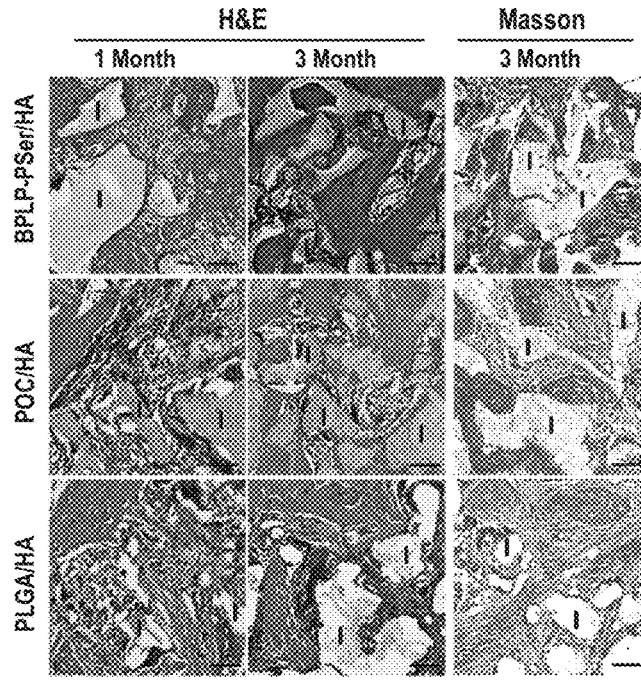
Fig. 6B
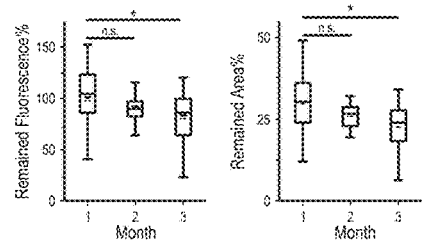
Fig. 6C
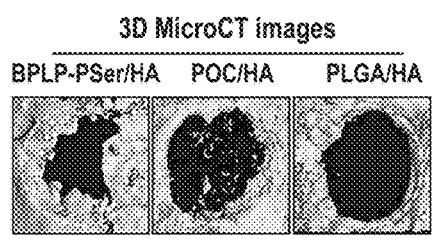
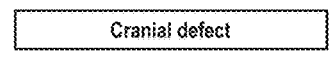
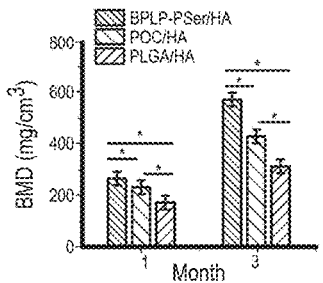
Fig. 6D
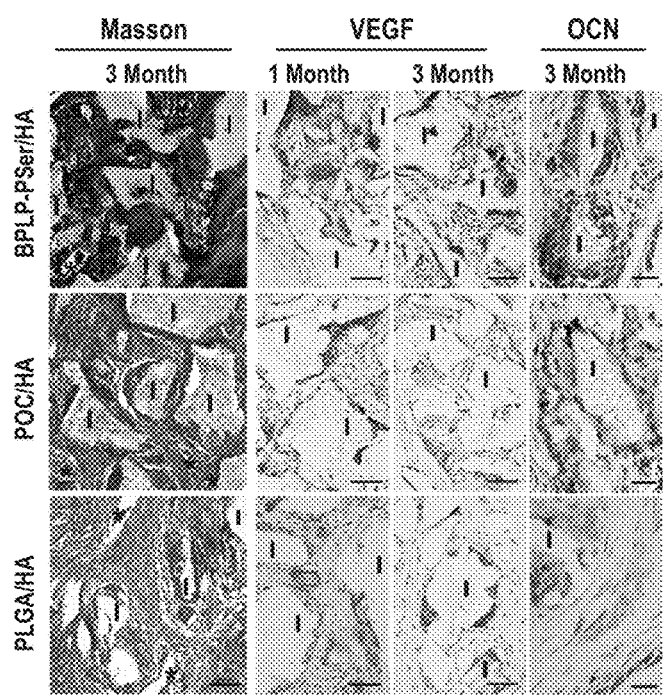
Fig. 6E

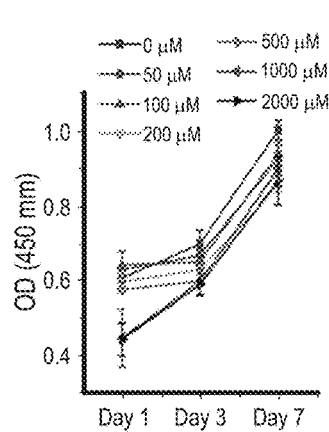
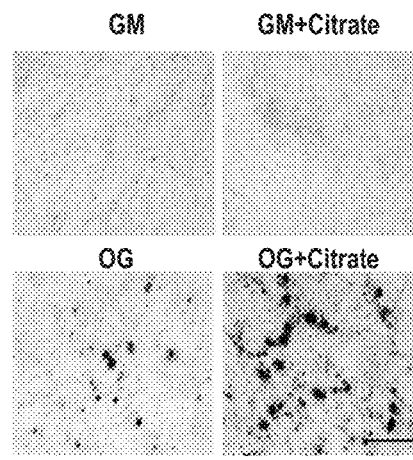
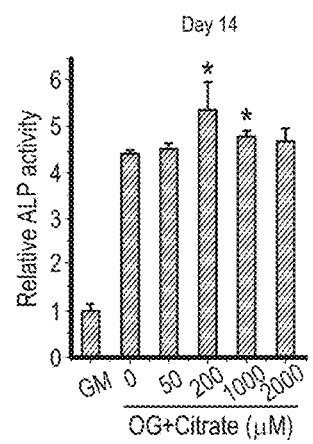
Fig. 7A     Fig. 7B     Fig. 7C
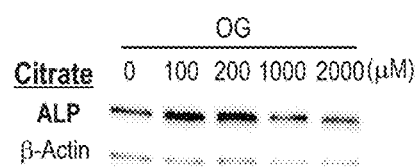
Fig. 7D
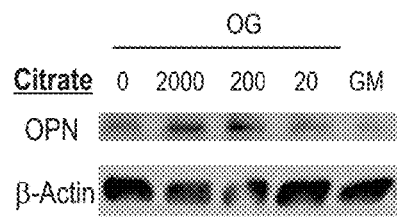
Fig. 7E
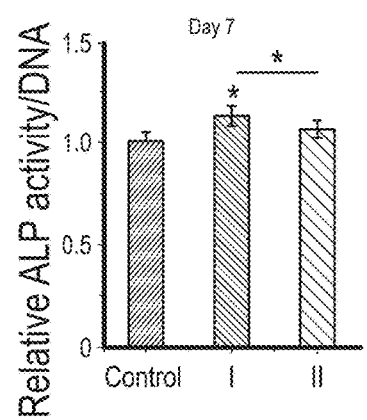
Fig. 7F

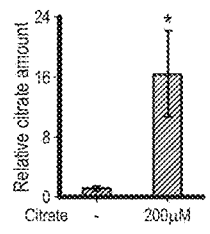 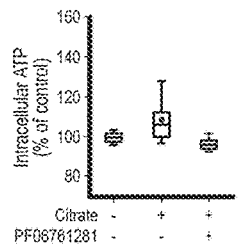 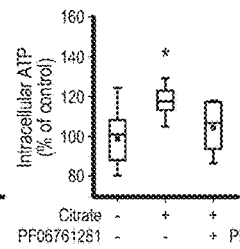 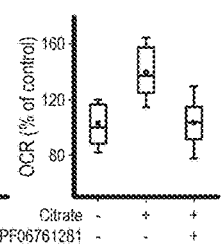 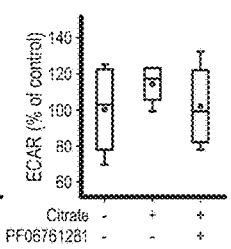
Fig. 8A  Fig. 8B  Fig. 8C  Fig. 8D  Fig. 8E
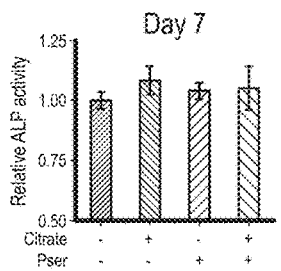 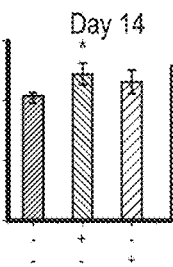 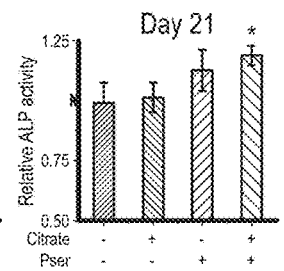 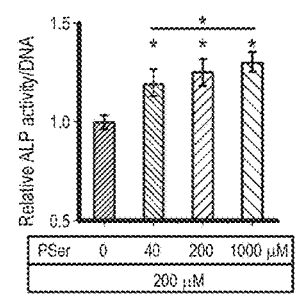
Fig. 8F  Fig. 8G
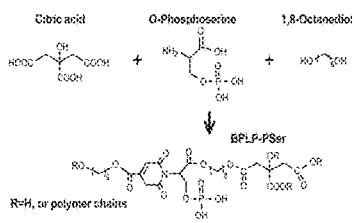 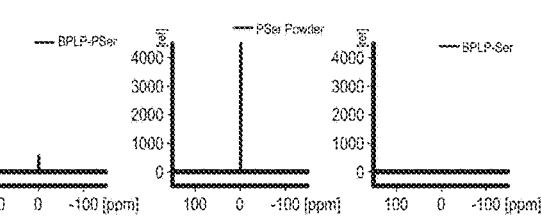
Fig. 9A  Fig. 9B
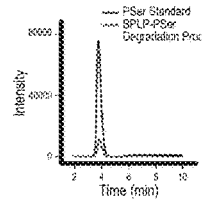 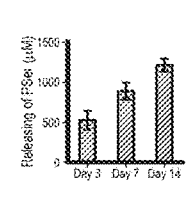 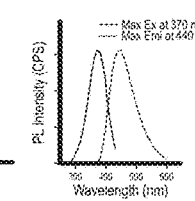 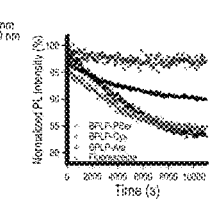 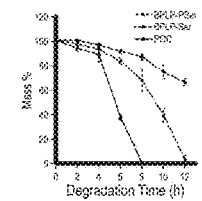
Fig. 9C  Fig. 9D  Fig. 9E  Fig. 9F  Fig. 9G  Fig. 9H

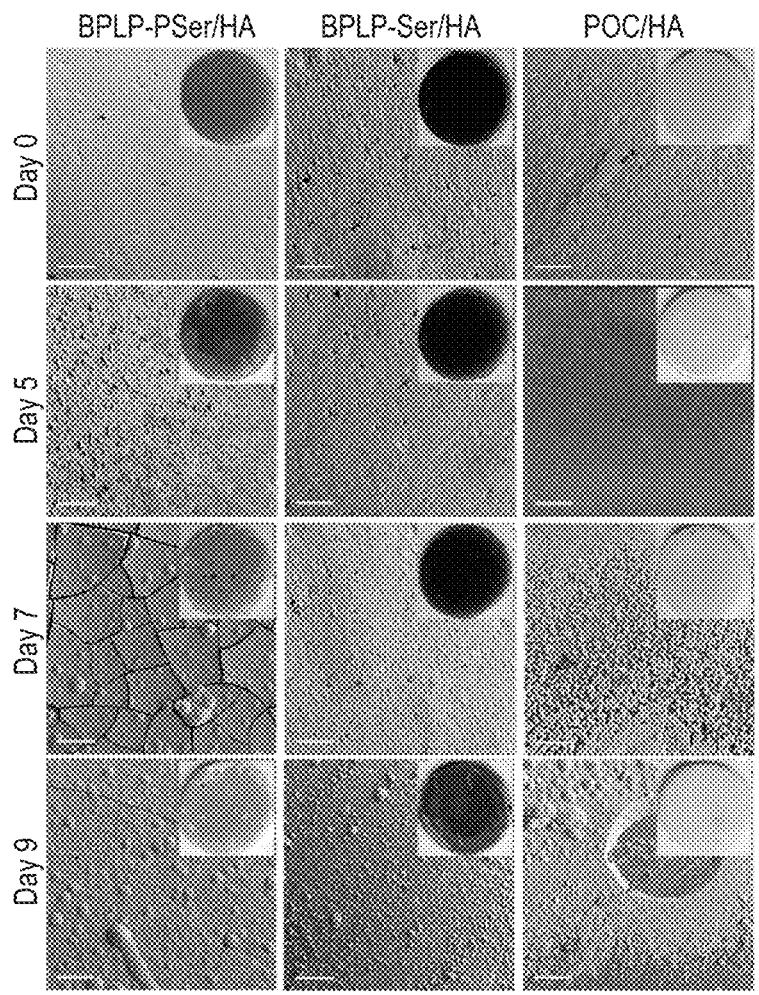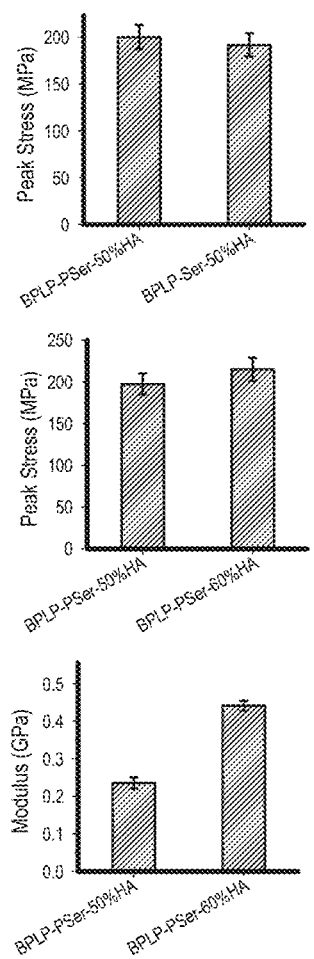
Fig. 11A                    Fig. 11B

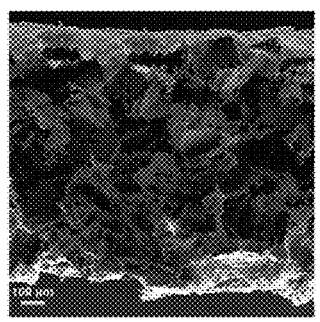
Fig. 13A
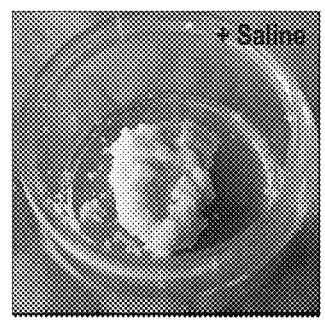
Fig. 13B
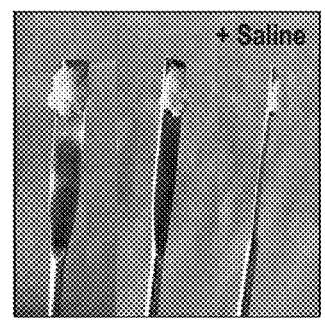
Fig. 13C
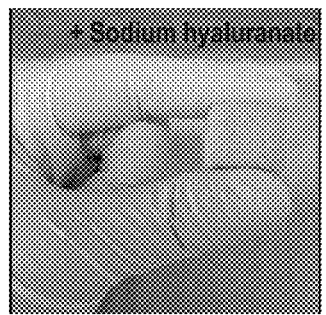
Fig. 13D
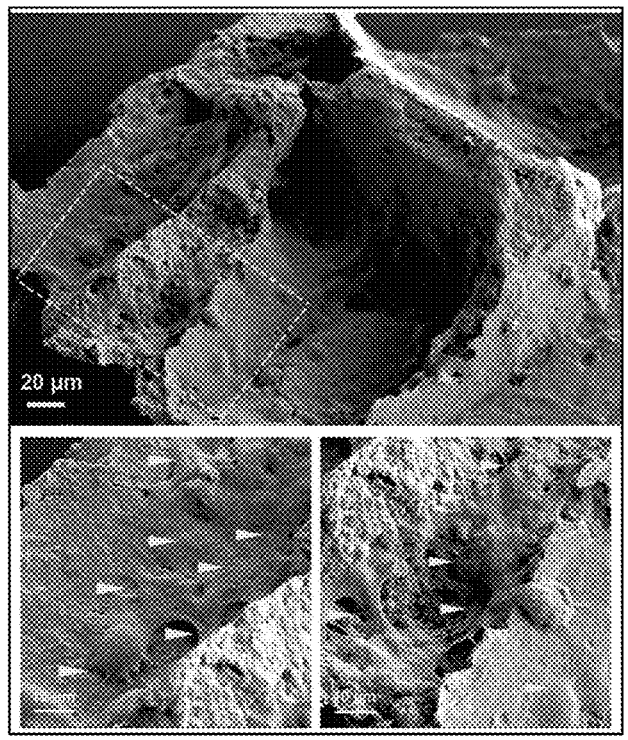
Fig. 13E
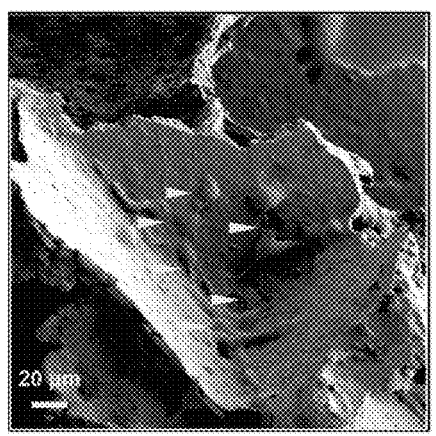
Fig. 13F
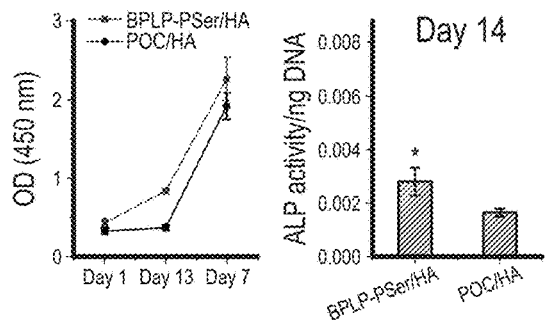
Fig. 13G
Fig. 13H

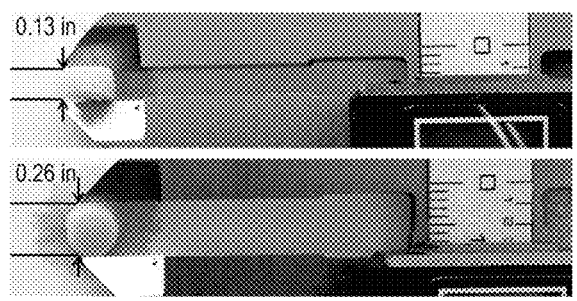
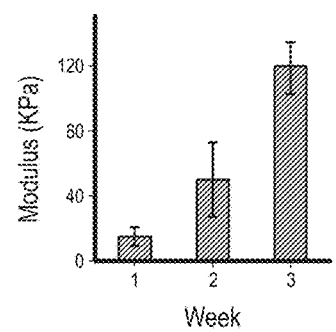
Fig. 14A
Fig. 14B
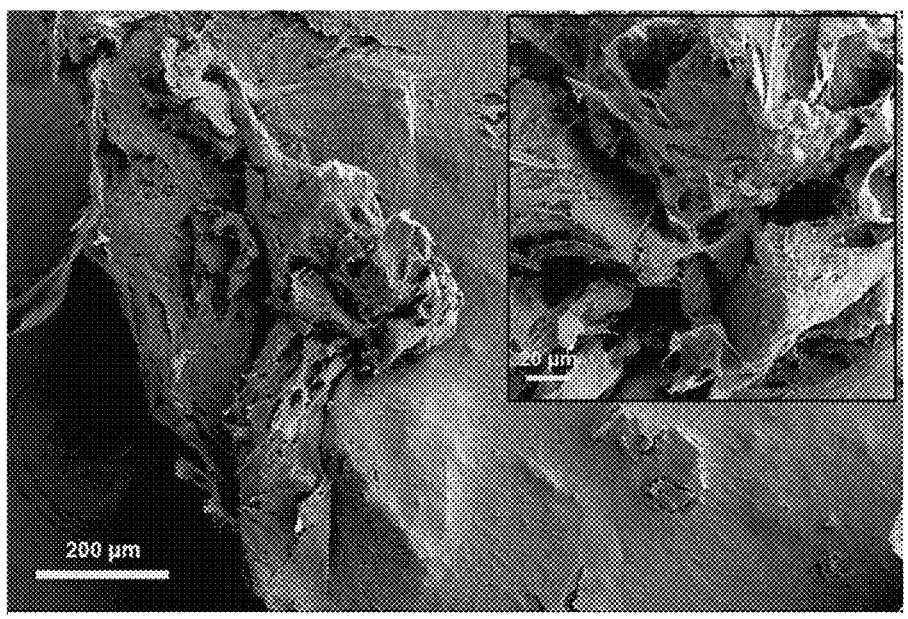
Fig. 14C
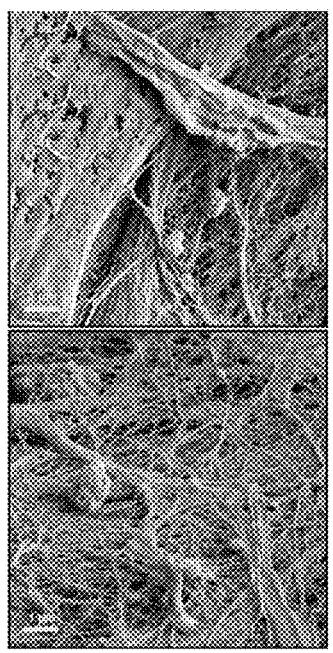
Fig. 14D
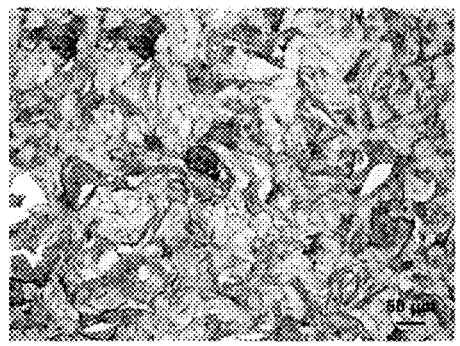
Fig. 14E

COMPOSITIONS AND METHODS FOR PROMOTING BONE REGENERATION

CROSS-REFERENCE TO RELATED APPLICATION

This application claims priority benefit to a US provisional patent application entitled "Compositions and Methods for Promoting Bone Regeneration," which was filed on Jul. 27, 2018, and assigned Ser. No. 62/703,949. The entire content of the foregoing provisional application is incorporated herein by reference.

STATEMENT REGARDING FEDERALLY SPONSORED RESEARCH

This invention was made with government support under Grant No. CA182670 awarded by the National Institutes of Health. The Government has certain rights in the invention.

FIELD

This invention relates to compositions and methods for promoting and/or accelerating bone regeneration, repair, and/or healing and, in particular, to compositions and methods of promoting bone regeneration, growth, repair, and/or healing using graft or scaffold materials.

BACKGROUND

Bone regeneration represents a substantial component of clinical practice with over 2 million cases of bone grafting performed each year worldwide towards the treatment of nonunion defects, trauma related injuries, congenital defects and tumor excision, as well as metabolic disorders such as obesity and diabetes mellitus. Although significant progress has been made in the development of orthopedic biomaterials, existing materials are limited by poor incorporation into the native bone, often lacking the biochemical and biological coordination necessary to mediate complex bone healing. Consequently, bone regeneration of nonunion defects, trauma related injuries, congenital defects and tumor excision, as well as metabolic disorders such as obesity and diabetes mellitus, can be a lengthy process reducing quality of life. Therefore, in light of these shortcomings, improved methods and materials for promoting and/or accelerating bone regeneration are needed.

SUMMARY

The methods and compositions disclosed herein take advantage of the novel finding that extracellular citrate, taken up through SLC13a5, mediates metabolic regulation of cellular energy status that influences the osteo-phenotype progression of human mesenchymal stem cells (hMSCs), a finding referred to as metabonegenic regulation. As described further herein, in some embodiments, metabonegenic regulation utilizes citrate and phosphoserine (PSer) to promote and/or accelerate bone regeneration. In particular, the temporal regulation of citrate metabolism and alkaline phosphatase at certain stages of osteogenesis promotes bone formation and accelerates bone regeneration. Further, as also described herein, a novel citrate-based orthopedic biomaterial was designed and implemented in animal models of cranial and condyle defects. In some embodiments, the biomaterial can be formed from a facile, one-pot synthesis comprising citrate, phosphoserine, and a diol to produce a brightly photoluminescent polymer that enables a multitude of imaging functionalities, as well as controlled temporal release of bioactive factors, citrate and PSer, from a biodegradable platform. The resulting biodegradable photoluminescent polymer, BPLP-PSer, was fabricated into BPLP-PSer/hydroxyapatite (HA) microparticulate (MP) scaffolds, exhibiting PSer-rich bioactive surfaces for improved tissue response and early bone deposition. Not intending to be bound by theory, it is believed that methods and compositions described herein promote and accelerate bone regeneration by promoting an osteogenic phenotype through metabonegenic regulation. Compositions described herein can be used as orthopedic materials, for example, to promote spinal fusion.

In one aspect, compositions for promoting and/or accelerating bone regeneration are described herein. Compositions described herein, in some cases, can be formed by additive manufacturing, such as methods of 3D printing. In some embodiments, a composition comprises a biodegradable scaffold. The composition comprises, in some cases, a citrate component, a phosphate component, and a particulate inorganic material. Moreover, as described further herein, the citrate component and/or phosphate component can be released from the composition simultaneously or sequentially, or in a manner that provides one component or the other to a bone site at a desired time or in a desired order.

The citrate component can be citric acid, citrate, or ester of a citric acid. The phosphate component can comprise a phosphate containing diol, polyol, or amine, serving as an organic phosphate donor. In some embodiments, the phosphate component comprises a phospho-serine, a phospho-threonine, and/or a phospho-tyrosine. Additionally, in some cases, the citrate component and/or phosphate component form a polymer. The citrate- and/or phosphate-containing polymer can further polymerize with, encapsulate, or otherwise incorporate the particulate inorganic material. The particulate inorganic material, in some embodiments, comprises hydroxyapatite, tricalcium phosphate, biphasic calcium phosphate, bioglass, ceramic, magnesium powder, magnesium alloy, decellularized bone tissue particles, or a combination of two or more of the foregoing.

In some embodiments, the biodegradable scaffold is microparticulate. Additionally, the microparticulate scaffold, in some embodiments, is a paste. In some cases, the biodegradable scaffold is a polymer network. In some cases, the scaffold comprises at least 20 weight percent, at least 30 weight percent, or at least 40 weight percent particulate inorganic material, based on the total weight of the scaffold.

Moreover, in some embodiments, the scaffold can have additional desirable properties including surface roughness, luminescence, and compressive strength. In some instances, the scaffold delivers 100-500 μM citric acid, citrate, or ester of a citric acid to the bone site. In some embodiments, the scaffold delivers 10-1000 μM phosphate component to the bone site. In still further embodiments, the molar ratio of (i) citrate component to (ii) phosphate component can be between 2:1 and 10:1.

In another aspect, methods of promoting and/or accelerating bone regeneration are described herein. Methods described herein can use one or more compositions described herein. For example, in some embodiments, a method of promoting and/or accelerating bone regeneration comprises delivering a composition to a bone site. The composition, in some cases, comprises a biodegradable scaffold. In other embodiments, the composition comprises a citrate component, a phosphate component, and, optionally, a particulate inorganic material, which may or may not be part of a biodegradable scaffold. Additionally, in some embodiments, delivering the composition comprises releasing the citrate component and releasing the phosphate component at the bone site. The citrate component, in some cases, is released before the phosphate component. In some embodiments, releasing the citrate component increases alkaline phosphatase activity and/or expression at the bone site and the alkaline phosphatase releases the phosphate component. For example, the phosphate component, in some cases, acts as a substrate of the alkaline phosphatase. Additionally, in some instances, a method described herein further comprises delivering stem cells to the bone site. The bone site, in some embodiments, is an intramembranous ossification site. In other embodiments, the bone site is an endochondral ossification site.

These and other embodiments are described in greater detail below in the detailed description.

BRIEF DESCRIPTION OF THE FIGURES

For purposes of the present disclosure, reference is made the appended figures, wherein:

FIG. 1 is a schematic model of the metabonegenic citrate-based material BPLP-PSer, inducing a concerted citrate/PSer regulation of cell energy metabolism towards osteo-phenotype progression (PSer: phosphoserine; Pi: inorganic phosphate; ALP: alkaline phosphatase; TCA cycle: tricarboxylic acid cycle; ADP: adenosine diphosphate; ATP: adenosine triphosphate; Runx2: Runt-related transcription factor 2).

FIG. 2A-2E are plots showing the osteopromotive effect of solute citrate. (A) Gene expression of Runx2, COL1a1 (encoding collagen type I alpha 1) and SPP1 (encoding osteopontin) in differentiating hMSCs with/without citrate supplementation at 200 µM in established osteogenic medium (OG) for 7 and 14 days, determined by real-time PCR. Data are shown as relative expression of target genes after normalization to corresponding control groups without citrate supplementation at day 7 (value set to 1.0). (B) Expression of Runx2 transcription factor in hMSCs with/without citrate supplementation in OG as determined by ELISA (In A&B, n≥4 biological replicates per group). (C) Schematic illustration of experimental design studying differentiation-stage dependence by restricting citrate supplementation (200 µM) only at the Proliferation stage (Group I; Day 0-Day 4), Matrix maturation stage (Group II; Day 4-Day 14), Mineralization stage (Group III; Day 14-Day 21), or 4 days in growth medium (GM) prior to osteo-induction (Group IV; Day −4-Day 0). (D) Alkaline phosphatase (ALP) expression at day 14 and calcium content in hMSCs at day 21 with citrate supplemented in OG only at specific differentiation stages (I, Group I; II, Group II; III, Group III). (E) ALP production and calcium content in hMSCs with/without 4 days of citrate pretreatment in GM before subjected to osteogenic differentiation in OG without citrate addition (Group IV). (In D&E, n=3-5 biological replicates per group; All plots throughout represent mean±s.d.; * indicating P<0.05).

FIGS. 3A-3K are plots and images related to citrate metabonegenic regulation and concerted action between citrate and PSer. (A) Protein synthesis of hMSCs with 200 µM citrate, Cycloheximide (Chx), or Torin 1 supplementation in GM for 1 and 4 days. (B) Western blot of SLC13a5 expression in hMSCs during osteogenic differentiation. (C) ALP production of hMSCs after 14 days of differentiation in OG supplemented with citrate, SLC13a5 inhibitor PF06761281, or both (In A-C, n=3-5 biological replicates per group). (D) Intracellular ATP determination, (E) oxygen consumption rate (OCR) study, (F) extracellular acidification rate (ECAR) study and (G) lactate production of undifferentiated hMSCs with 1 day treatment of citrate and SLC13a5 inhibitor in GM (In D-G, n≥8 biological replicates per group). Intracellular ATP determination of (H) hMSCs and (I) differentiating hMSCs with citrate, PSer or both, supplemented in GM and OG, respectively (In H&I, n=6-8 biological replicates per group). (J) ALP production of differentiating hMSCs after 7, 14 and 21 days of differentiation with citrate, or citrate and PSer supplemented in OG (n=4 biological replicates per group; All plots represent mean±s.d.; * indicating P<0.05). (K) Immunofluorescent staining of osteopontin (OPN; red, with DAPI nuclear counterstain, blue) expression after 21 days of differentiation in OG with citrate, PSer or both supplement. The plus (+) and minus (−) symbols in the figure denote GM/OG medium in the presence and absence of citrate and other specific chemicals, respectively. (Scale bar: 100 m).

FIGS. 6A-6E are plots and images related to in vivo efficacy of the BPLP-PSer/HA MP scaffolds. (A) MicroCT images of femoral condyle defects (top) with BPLP-PSer/HA, POC/HA, and PLGA/HA MP scaffolds at 3 months after implantation, along with bone mineral density (BMD) analysis (bottom; n=6 defects per group). (B) H&E staining (left) and Masson's trichrome staining (right) of femoral condyle defects treated with different Mps. Scale bars, 50 µm. I indicates implants. (C) Fluorescent analysis of remaining total fluorescent signal (left) as well as remaining scaffold area (right) in defects, determined by analyzing the fluorescent images of tissue sections in the BPLP-PSer/HA group using Image J (n≥40 per time point; All plots represent mean±s.d.; * indicating P<0.05; n.s., not significant). (D) MicroCT images of cranial defects (top) with BPLP-PSer/HA, POC/HA, and PLGA/HA MPs at month 3 after implantation, along with BMD analysis (bottom; n=5 defects per group). (E) Masson staining (left; scale bar: 50 µm), immunohistochemical staining for vascular endothelial growth factor (VEGF; middle; scale bar, 50 µm) and osteocalcin (OCN; Right; Scale bar, 20 µm) of cranial defects treated with different Mps. I indicates implant. * indicate blood vessels.

FIGS. 7A-7F are results of osteo-promotive effects of citrate. (A) Cell proliferation of hMSCs with treatment of citrate at different concentrations determined by cell counting kit-8 (CCK-8) assay (n≥4 biological replicates per group). (B) Calcium nodule formation by hMSCs cultured in growth medium (GM) or osteogenic medium (OG) with/without citrate supplementation at 200 µM for 14 days. (C) Alkaline phosphatase (ALP) expression of differentiating hMSCs with citrate supplement in OG at different concentrations (0-2000 µM) after 14 days of differentiation (Scale bar: 500 µm). (D) ALP expression of hMSCs differentiated for 14 days in OG with citrate treatment at different concentrations (0-2000 µM) by western blot. (E) Osteopontin (OPN) expression of hMSCs differentiated for 7 days in OG with citrate treatment at different concentrations (0-2000 µM) by western blot. (F) ALP expression of differentiating hMSCs at day 7 with citrate supplemented in OG only at specific differentiation stages (In C&F, n=3 biological replicates; All plots represent mean±s.d.; * indicating P<0.05).

FIGS. 8A-8G are results of citrate metabonegenic regulation and concerted action between citrate and PSer. (A) Intracellular citrate amount in hMSCs incubated with/without citrate supplementation in GM for 24 h, determined by Citrate Assay (n=3 biological replicates per group). Intracellular ATP determination of differentiating hMSCs (differentiated for 14 days) after (B) 1 day and (C) 4 days treatment of citrate, or citrate with SLC13a5 inhibitor PF06761281 in OG. (D) Oxygen consumption rate (OCR) study and (E) extracellular acidification rate (ECAR) study of differentiating hMSCs with 1 day treatment of citrate, or citrate with SLC13a5 inhibitor in OG (In B-E, n≥6 biological replicates; All plots represent mean±s.d.; * indicating P<0.05). (F) ALP production of hMSCs with citrate, PSer or both supplemented in OG after 7, 14 and 21 days. (G) ALP production of hMSCs differentiated for 21 days with citrate and increasing concentrations of PSer (0-1000 µM) supplement in OG. (In F&G, n≥4 biological replicates; All plots represent mean±s.d.; * indicating P<0.05).

FIGS. 9A-9H are results of BPLP-PSer synthesis and characterization. (A) Illustration of BPLP-PSer pre-polymer synthesis. (B) 31P-nuclear magnetic resonance (NMR) spectra of BPLP-PSer pre-polymer solution (Left) showed a clear peak corresponding to that of the reference PSer sample (Middle), whereas the spectra of pre-BPLP-Ser (Right; PSer replaced with L-Ser in the reaction scheme above) lacked this peak. High performance liquid chromatography (HPLC) analysis further confirmed the presence of PSer (C) in the accelerated degradation products of BPLP-PSer films, as well as (D) in release medium incubated with BPLP-PSer films. (E) The inorganic phosphate that liberated by incubating ALP solution with different polymer films, determined by Piper phosphate assay. (F) Max excitation and emission of BPLP-PSer. (G) Photostability of BPLP-PSer. (H) Accelerated degradation profile of BPLP-PSer, BPLP-Ser, and POC films by measuring remaining weight, showing that the degradation of BPLP-PSer was slower than POC but faster than BPLP-Ser films (In D, E&H, n≥5 replicates per group; All plots represent mean±s.d.).

FIGS. 11A-11B are images and plots showing in vitro mineralization tests and mechanical properties of polymer/hydroxyapatite (HA) composites. (A) In vitro Mineralization test on polymer/HA composites showed an accelerated mineralization on BPLP-PSer/HA composites over control composites (Scale bar: 100 µm). Inserted bright field images confirmed the superior performance of BPLP-PSer/HA. (B) Compressive mechanic properties of BPLP-PSer/50% HA, BPLP-PSer/60% HA and BPLP-Ser/50% HA cylindrical composites (n=6 composites per group; All plots represent mean±s.d.).

FIGS. 13A-13H are images and plots showing results of BPLP-PSer/HA MP scaffolds and stem cell studies. (A) SEM image of the cross-section of BPLP-PSer/HA porous composite scaffold with pore sizes of ~150-250 µm prepared by salt-leaching method. (B) MP scaffolds wetted with sterilized saline (C) showing great handling capacity. (D) Moldability of BPLP-PSer MPs after mixed with 2 mg/mL of sodium hyaluranate solution. (E) SEM images of hMSCs adhered onto the "ridge and cliff" and (F) "groove" surface features of MP scaffolds after 6 h of dynamic seeding. (Arrow heads: adhered hMSCs) (G) Proliferation of hMSCs on different MP scaffolds tested by CCK8. (H) ALP production of hMSCs cultured on Mps in transwell 3D models in GM without osteogenic inducers at day 14 (In G&H, n=3-4 biological replicates per group; All plots represent mean±s.d.; * indicating P<0.05).

FIGS. 14A-14E are images and a plot showing results of hMSC differentiation on MPs in transwell 3D model. (A) Round disk shaped cell-Mps constructs with defined size capable of being prepared reproducibly by controlling the size of transwell, Mps amount and cell seeding density. (B) Compressive modulus of disk shaped cell-MP constructs after differentiating cells for 1, 2 and 3 weeks in OG (n=3 cell-MP constructs per time point). (C) Additional SEM images of a thick layer of differentiating hMSCs covering and bridging MP scaffolds to generate intact constructs. (D) Additional SEM images of massive extracellular matrix production produced by differentiating hMSCs with signs of minerals deposition. (E) H&E staining of the cryosections of cells-MP constructs showing the close and integrated interaction between cells and MPs (Scale bar: 50 µm).

DETAILED DESCRIPTION

Figure 4A:
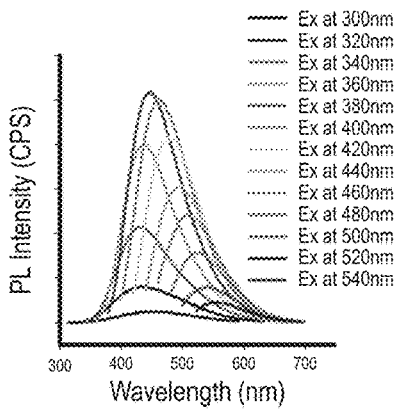
FIGS. 4A-4I are plots related to BPLP-PSer as a new biocompatible photoluminescent biodegradable polymer. (A) Emission spectra of BPLP-PSer-0.2 pre-polymer, displaying tunable emission wavelengths by changing the excitation wavelength. (B) Emission spectra of BPLP-PSer pre-polymer solutions with various molar ratios of PSer excited at 370 nm. (C) Fluorescent images of BPLP-PSer films after accelerated degradation for pre-determined time (0, 2, 4, 6, 8, 10, 12 h) in 0.05 M NaOH solution. (D) Quantitative analysis of the remaining fluorescent signal in BPLP-PSer films (L1) and corresponding fluorescent signal in degradation medium, released from polymer films (L2). (E) Comparison of the remaining fluorescence profile of BPLP-PSer films (L1) to the conventional mass remaining profile (L0; In c-e, n=5 films per time point). (F) Cytotoxicity test on leachable extracts from polymer films to L929 cells examined by cell counting kit-8 (CCK-8), showing a significantly higher cell viability in the BPLP-PSer group compared to POC. (G) Release of inflammatory factor interleukin-1 β(IL-1β) from THP-1 monocytes activated by incubating with polymer films, determined by ELISA. (H) ALP production of differentiating hMSCs cultured in OG on polymer films (BPLP-PSer 0.1/0.2/0.3 respectively indicating 0.1, 0.2, or 0.3 molar ratios of PSer to citrate). (I) Expression of SPP1 gene encoding osteopontin of differentiating hMSCs cultured on polymer films in OG. Data are shown as relative expression of SPP1 gene after normalization to corresponding control group without citrate supplemented at day 7 (set to 1). (In F-I, n=3-5 biological replicates per group; All plots represent mean±s.d.; * indicating P<0.05; n.s., not significant).

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of this invention. Numerous modifications and adaptations will be readily apparent to those of ordinary skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9. Similarly, a stated range of "1 to 5" should be considered to include any and all subranges beginning with a minimum value of 1 or more and ending with a maximum value of 5 or less, e.g., 1 to 4, or 2 to 5, or 3 to 4.

All ranges disclosed herein are also to be considered to include the end points of the range, unless expressly stated otherwise. For example, a range of "between 5 and 10," "from 5 to 10," or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Compositions

In one aspect, compositions for promoting and/or accelerating bone regeneration, including bone growth, bone healing, and/or bone repair are described herein. It should be understood that one or more compositions described herein can be used in one or more methods of promoting and/or accelerating bone regeneration described herein, including for bone growth, bone healing, and/or bone repair.

In some embodiments, a composition for promoting bone growth comprises a graft or scaffold. A "graft" or "scaffold," for reference purposes herein, can refer to any structure usable as a platform or implant for the replacement of missing bone or for promotion of growth of new bone. Moreover, as utilized herein, the terms "graft" or "scaffold" may be synonymous. For example, a graft or scaffold of a composition described herein can be used in the repair of a bone defect, the replacement of missing or removed bone, or for the promotion of new bone growth, as in the case of a bone fusion procedure. Further, it is to be understood that grafts or scaffolds consistent with compositions and methods described herein can have any structure or be formed in any shape, configuration, or orientation not inconsistent with the objectives of the present invention. For example, in some embodiments, a graft or scaffold can be shaped, configured, or oriented in such a manner as to correspond to a defect or bone growth site to be repaired. For example, a graft or scaffold utilized in the repair of a bone defect, such as a cranial defect or condyle defect, may be formed, molded, or resized to a size and/or shape corresponding to the defect. In certain other cases, such as in a bone fusion procedure, a graft or scaffold in compositions and methods described herein can have a shape, configuration, orientation, or dimensions adapted to traverse a gap between the bones to be fused and/or to reinforce a bone growth site. In this manner, particular shapes, sizes, orientations and/or configurations of grafts or scaffolds described herein are not intended to be limited to a particular set or subset of modalities on, within, or adjacent to a bone growth site. A "bone site," as referenced herein, can be any area in which bone regeneration, bone ossification, bone growth, or bone repair may be desired. In certain non-limiting examples, a bone site can comprise or include a bone defect, a site in which bone has been removed or degraded, and/or a site of desired new bone growth or regeneration, as in the case of a spinal or other bone fusion.

The graft or scaffold of compositions and methods described herein, in some cases, can comprise (a) a polymer formed from (i) citric acid, a citrate, or an ester of citric acid and (ii) a phosphate component. In some cases, the polymer can further comprise a (iii) polyol that differs from (i) and (ii). Additionally, the graft or scaffold can further comprise (b) a particulate inorganic material dispersed within the polymer and/or polymerized with the pre-polymer.

The polymer of a graft or scaffold described herein can comprise or be formed from any phosphate-containing polymer not inconsistent with the objectives of the present invention. A "phosphate-containing polymer," for reference purposes herein, comprises a polymer or oligomer comprising a phosphate moiety. The phosphate moiety is present in a pendant or side group or chain of the component. For example, the phosphate moiety should be readily accessible as a substrate for enzymatic cleavage, such as by a phosphatase enzyme. In some embodiments, the phosphate moiety is a repeating unit of the component. Further, a "phosphate-containing polymer," for reference purposes herein, comprises a moiety having the structure of Formula (I):

wherein $R_{100}$ and $R_{200}$ each comprise a moiety that is operable to incorporate the phosphate component into a polymer via a condensation reaction. For example, $R_{100}$ and $R_{200}$ can each comprise, independently, a moiety including —$NH_2$, —COOH, or —OH. It is further to be understood that the segment connecting $R_{100}$ and $R_{200}$ above need not be a direct bond between $R_{100}$ and $R_{200}$. Instead, the segment connecting $R_{100}$ and $R_{200}$ can include any number or type of atoms, provided that $R_{100}$ and $R_{200}$ are operable to incorporate the phosphate component of Formula (I) into a polymer or oligomer described herein. Moreover, in Formula (I), $R_{301}$ and $R_{302}$ can each independently be H or a C1-C4 hydrocarbyl (that is, a hydrocarbyl moiety have 1 to 4 carbon atoms, such as $CH_3$ or $CH_2CH_3$). Further, in some cases, $R_{301}$ and/or $R_{302}$ is replaced with a cation, such as a monovalent metal cation (e.g., $Na^+$ or $K^+$). In some preferred embodiments, both $R_{301}$ and $R_{302}$ are H.

Additionally, the phosphate-containing polymer of a graft or scaffold described herein can also be a citrate-containing polymer. A "citrate-containing polymer," for reference purposes herein, comprises a polymer or oligomer comprising a citrate moiety. Additionally, in some cases, the citrate moiety is present in the backbone or main chain of the polymer. The citrate moiety may also be present in a pendant or side group or chain of the polymer. In some embodiments, the citrate moiety is a repeating unit of the polymer or is formed from a repeating unit of the polymer. Further, a "citrate moiety," for reference purposes herein, comprises a moiety having the structure of Formula (II):

wherein $R_1$, $R_2$, and $R_3$ are independently —H, —$CH_3$, —$CH_2CH_3$, $M^+$, or a point of attachment to the remainder of the polymer;
$R_4$ is —H or a point of attachment to the remainder of the polymer; and
$M^+$ is a cation such as $Na^+$ or $K^+$, provided that at least one of $R_1$, $R_2$, $R_3$, and $R_4$ is a point of attachment to the remainder of the polymer.

For example, in some cases, a phosphate-containing polymer of a composition described herein comprises the reaction product of (i) citric acid, a citrate, or an ester of citric acid, such as triethyl citrate or another methyl or ethyl ester of citric acid, with (ii) a polyol, such as a diol, and (iii) a phospho-amino acid or phospho-polypeptide. Non-limiting examples of polyols suitable for use in some embodiments described herein include C2-C20, C2-C12, or C2-C6 aliphatic alkane diols, including α,ω-n-alkane diols, or α,ω-alkene diols. For instance, in some cases, a polyol comprises 1,4-butanediol, 1,6-hexanediol, 1,8-octanediol, 1,10-decanediol, 1,12-dodecanediol, 1,16-hexadecanediol, or 1,20-icosanediol. Branched α,ω-alkane diols or α,ω-alkene diols can also be used. Additionally, a polyol can also be an aromatic diol. Further, in some embodiments, a polyol comprises a poly(ethylene glycol) (PEG) or poly(propylene glycol) (PPG). Any PEG or PPG not inconsistent with the objectives of the present disclosure may be used. In some embodiments, for instance, a PEG or PPG has a weight average molecular weight between about 100 and about 5000 or between about 200 and about 1000.

A phospho-amino acid, in some embodiments, comprises an L-amino acid, a D-amino acid, or a D,L-amino acid that is phosphorylated. Non-limiting examples of phospho-amino acids suitable for use in some embodiments described herein include phospho-serine, phospho-threonine, or phospho-tyrosine. Further, in some instances, a phospho-amino acid comprises a phosphorylated, alkyl-substituted alpha-amino acid, such as a phosphorylated, methyl-substituted amino acid derived from any of the 22 "standard" or proteinogenic amino acids, such as methyl serine.

Moreover, in some cases, a phospho-polypeptide comprises one or more phosphorylated amino acids in the polypeptide (or oligopeptide). In some embodiments, some amino acids present in an oligopeptide or polypeptide can unphosphorylated, while others are phosphorylated. Additionally, in some embodiments, a phosphorylated oligopeptide or polypeptide can be mono-, di-, or triphosphorylated. Additionally, in some cases, an amino acid of a phospho-amino acid or of a phospho-polypeptide forms a luminescent moiety when the phosphate-containing component reacts with other components to form a polymer or oligomer, as previously described for "BPLP" polymers or oligomers. Thus, in some embodiments, the polymer or oligomer of a composition described herein can be a luminescent (e.g., fluorescent) polymer, thereby providing a luminescent (e.g., fluorescent) graft or scaffold. Such a luminescent polymer can be referred to generically herein, in some cases, as a phospho-amino acid biodegradable photoluminescent polymer (which may be denoted generically as "BPLP-PA"). Such a luminescent polymer may also be denoted with reference to a specific phosphorylated amino acid (such as phospho-serine ("PSer"), to provide "BPLP-PSer," for example).

Additionally, in some embodiments, phosphate-containing polymer of a graft or scaffold described herein can comprise the reaction product of (i) citric acid, a citrate, or an ester of citric acid with (ii) a polyol, (iii) a phospho-amino acid or -polypeptide, and (iv) an amine, an amide, or an isocyanate. In such instances, the polyol can comprise any polyol described above. The ester of citric acid can comprise any ester of citric acid described above, and the phospho-amino acid or phospho-polypeptide can comprise any phosphorylated amino acid or polypeptide described above. Further, an amine, in some embodiments, comprises one or more primary amines having two to ten carbon atoms. In other cases, an amine comprises one or more secondary or tertiary amines having two to fifteen carbon atoms. In some instances, an amine comprises a secondary or tertiary amine comprising one or more hydroxyl-containing groups bonded to the nitrogen. For example, in some cases, an amine comprises an amine-containing diol such as N-methyldiethanolamine (MDEA). An isocyanate, in some embodiments, comprises a monoisocyanate. In other instances, an isocyanate comprises a diisocyanate such as an alkane diisocyanate having four to twenty carbon atoms.

In addition, a phosphate-containing polymer of a graft or scaffold described herein can also comprise the reaction product of (i) citric acid, a citrate, or an ester of citric acid with (ii) a polyol, (iii) a phospho-amino acid or -polypeptide, and (iv) a polycarboxylic acid, such as a dicarboxylic acid or a functional equivalent of a polycarboxylic acid, such as a cyclic anhydride or an acid chloride of a polycarboxylic acid. In such cases, the polyol can comprise any polyol described above. The ester of citric acid can comprise any ester of citric acid described above, and the phospho-amino acid or -polypeptide can comprise any phosphorylated amino acid or polypeptide described above. Moreover, the polycarboxylic acid or functional equivalent thereof can be saturated or unsaturated. For example, in some instances, the polycarboxylic acid or functional equivalent thereof comprises maleic acid, maleic anhydride, fumaric acid, or fumaryl chloride. A vinyl-containing polycarboxylic acid or functional equivalent thereof may also be used, such as allylmalonic acid, allylmalonic chloride, itaconic acid, or itaconic chloride. Further, in some cases, the polycarboxylic acid or functional equivalent thereof can be at least partially replaced with an olefin-containing monomer that may or may not be a polycarboxylic acid. In some embodiments, for instance, an olefin-containing monomer comprises an unsaturated polyol such as a vinyl-containing diol.

Further, in some cases, a phosphate-containing polymer described herein comprises the reaction product of (i) citric acid, a citrate, or an ester of citric acid with (ii) a polyol, (iii) a phospho-amino acid or -polypeptide, and (iv) an isocyanate such as a diisocyanate. Additionally, in some instances, an acid anhydride and/or an acid chloride can be used in conjunction with the citric acid, citrate, or ester of citric acid. The polyol can be any polyol described above, the ester of citric acid can be any ester of citric acid described above, the isocyanate can be any isocyanate described above, and the phospho-amino acid or phosphor-polypeptide can comprise any phosphorylated amino acid or polypeptide described above. Further, the acid anhydride and/or acid chloride can include any acid anhydride and/or acid chloride described above, including, or instance, a polyacid anhydride or a polyacid chloride.

In addition, in some embodiments, a phosphate-containing polymer described herein comprises the reaction product of (i) citric acid, a citrate, or an ester of a citric acid with (ii) a polyol, (iii) a phospho-amino acid or -polypeptide, and (iv) a catechol-containing species. The citrate or ester of citric acid can be any citrate or ester of citric acid described above, such as a methyl or ethyl ester of citric acid. The polyol can be any polyol described above, and the phospho-amino acid or polypeptide can be any phosphorylated amino acid or polypeptide described above.

The catechol-containing species can comprise any catechol-containing species not inconsistent with the objectives of the present disclosure. In some cases, a catechol-containing species used to form a phosphate-containing polymer described herein comprises at least one moiety that can form an ester or amide bond with another chemical species used to form the polymer. For example, in some cases, a catechol-containing species comprises an amine moiety or a carboxylic acid moiety. Further, in some instances, a catechol-containing species comprises a hydroxyl moiety that is not part of the catechol moiety. In some embodiments, a catechol-containing species comprises dopamine. In other embodiments, a catechol-containing species comprises L-3,4-dihydroxyphenylalanine (L-DOPA) or D-3,4-dihydroxyphenylalanine (D-DOPA). In some cases, a catechol-containing species comprises 3,4-dihydroxyhydrocinnamic acid. Moreover, in some embodiments, a catechol-containing species is coupled to the backbone of the polymer through an amide bond. In other embodiments, a catechol-containing species is coupled to the backbone of the polymer through an ester bond.

Additionally, in some cases, a phosphate-containing polymer described herein is cross-linked via one or more click chemistry reactions. For example, in some embodiments, polymers described herein can comprise or include the reaction product of (i) citric acid, a citrate, or an ester of citric acid, such as triethyl citrate or another methyl or ethyl ester of citric acid with (ii) a polyol such as a diol (iii) a phospho-amino acid or -polypeptide and (iv) a monomer comprising an alkyne moiety and/or an azide moiety. Any polyol described herein above can be used. Further, in some instances, the polyol can be at least partially replaced by an alcohol having only one hydroxyl group or by an amine or an amide. Further, in some cases, the polyol can be at least partially replaced by a polymer or oligomer having one or more hydroxyl, amine, or amide groups. Such a polymer or oligomer, in some instances, can be a polyester, polyether, or polyamide. Thus, in some embodiments, a composition described herein comprises the reaction product of (i) citric acid, a citrate, or an ester of citric acid with (ii) an alcohol, amine, amide, polyester, polyether, or polyamide, (iii) a phospho-amino acid or -polypeptide, and (iv) a monomer comprising an alkyne moiety and/or an azide moiety.

Monomers comprising one or more alkyne and/or azide moieties used to form a polymer described herein can comprise any alkyne- and/or azide-containing chemical species not inconsistent with the objectives of the present disclosure. For example, in some instances, one or more such monomers comprise a polyol such as a diol. Such a monomer, in some cases, can be incorporated into the polymer through the reaction of one or more hydroxyl moieties of the monomer with a carboxyl or carboxylic acid moiety of another monomer (such as a citric acid monomer) described herein. Moreover, in some instances, an alkyne- or azide-containing monomer can be used to partially replace another monomer (such as a diol). For example, such a monomer can be a diazido-diol (DAzD) or an alkyne diol (AlD).

Further, in some embodiments, a phosphate-containing polymer of a composition described herein is formed from a combination of monomers described above. For example, in some cases, a polymer of a composition described herein can comprise the reaction product of (i) citric acid, a citrate, or an ester of citric acid with (ii) a polyol, (iii) one or more alkynes and/or azides, (iv) an amine, an amide, or an isocyanate, and (v) a phospho-amino acid or -polypeptide. In such instances, the polyol can comprise any polyol described above, and the ester of citric acid can comprise any ester of citric acid described above. Further, the amine can comprise any amine described above, such as one or more primary amines having two to ten carbon atoms, one or more secondary or tertiary amines having two to fifteen carbon atoms, or one or more secondary or tertiary amines having one or more hydroxyl groups bonded to the nitrogen, as in the case of an amine-containing diol. The isocyanate can comprise any isocyanate described above. The phospho-amino acid or phosphor-polypeptide can comprise any phospho-amino acid or phosphor-polypeptide described above.

Similarly, in other cases, a polymer comprises the reaction product of (i) citric acid, a citrate, or an ester of citric acid with (ii) a polyol, (iii) one or more alkynes and/or azides, (iv) a phospho-amino acid, and (v) a polycarboxylic acid such as a dicarboxylic acid or a functional equivalent of a polycarboxylic acid, such as a cyclic anhydride or an acid chloride of a polycarboxylic acid. In such cases, the polyol can comprise any polyol described above, and the ester of citric acid can comprise any ester of citric acid described above. The phospho-amino acid can comprise any phospho-amino acid described above. Moreover, the polycarboxylic acid can comprise any polycarboxylic acid or functional equivalent described above.

A reaction product described hereinabove, in some cases, is a condensation polymerization reaction product of the identified species. Thus, in some embodiments, at least two of the identified species are co-monomers for the formation of a copolymer. In some such embodiments, the reaction product forms an alternating copolymer or a statistical copolymer of the co-monomers. Additionally, as described further herein, species described hereinabove may also form pendant groups or side chains of a copolymer.

In some embodiments, a phosphate-containing polymer of a composition described herein is a polymer or oligomer formed from one or more monomers of Formula (A1), optionally one or more monomers of Formula (A2), and one or more monomers of Formula (B1), (B2), or (B3), and one or more monomers of Formula (J):

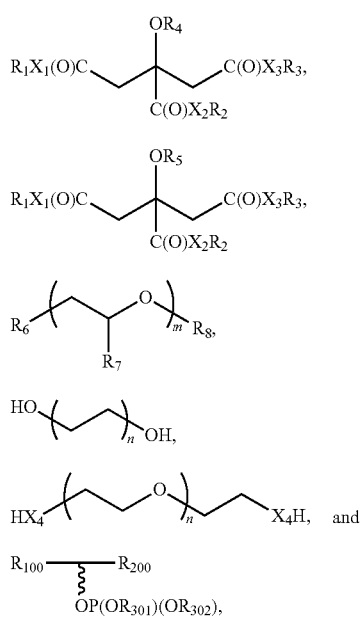

wherein $X_1$, $X_2$, $X_3$, and $X_4$ are each independently —O— or —NH—;
$R_1$, $R_2$, and $R_3$ are each, independently, —H or a C1 to C22 alkyl or alkenyl group or $M^+$,
$R_4$ is H;
$R_5$ is $C(O)R_{23}$;
$R_6$ is —H, —NH, —OH, —OCH$_3$, —OCH$_2$CH$_3$, —CH$_3$, or —CH$_2$CH$_3$;
$R_7$ is —H or a C1 to C23 alkyl or alkenyl group —CH$_3$;
$R_8$ is —H, a C3 to C22 alkyl or alkenyl group, —CH$_2$CH$_2$OH, or —CH$_2$CH$_2$NH$_2$;
$R_{23}$ is a C14 to C22 alkyl or alkenyl group;
n and m are independently integers ranging from 1 to 20; and
$R_{100}$, $R_{200}$, $R_{301}$, and $R_{302}$ are as described above in the context of Formula (I).

Further, the monomers of Formula (A1), (A2), (B1), (B2), (B3), and (J) can be used in any molar ratio not inconsistent with the objectives of the present disclosure. In addition, altering the molar ratios of monomers can, in some embodiments, alter the biodegradability, the mechanical strength, fluorescence intensity, and/or other properties of the polymer formed from the monomers. In some embodiments, the molar ratio of monomers (A1) and (A2) (the combination subsequently being referred to herein as "monomer (A)") to monomer (B1) or monomer (B2) or (B3) is between about 1:10 and about 10:1 or between about 1:5 and about 5:1. In some embodiments, the molar ratio of monomer (A) to monomer (B1) or monomer (B2) or (B3) is between about 1:4 and about 4:1. In some embodiments, the molar ratio is about 5:6.

In some embodiments, the molar ratio of monomer (B1) or monomer (B2) or monomer (B3) to monomer (J) is between about 1:20 and about 20:1 or between about 1:10 and about 10:1. In some embodiments, the molar ratio of monomer (B1) or monomer (B2) or monomer (B3) to monomer (J) is between about 1:5 and about 5:1. In some embodiments, the molar ratio is about 6:1.

In some embodiments, the molar ratio of monomer (A) to monomer (J) is between about 1:20 and about 20:1 or between about 1:10 and about 10:1. In some embodiments, the molar ratio of monomer (A) to monomer (J) is between about 1:3 and about 3:1. In some embodiments, the molar ratio is about 5:1.

In some embodiments, a phosphate-containing polymer of a graft or scaffold utilized in a method described herein is formed from one or more monomers of Formula (A), one or more monomers of Formula (B1) or (B2), one or more monomers of Formula (C), and one or more monomers of Formula (J):

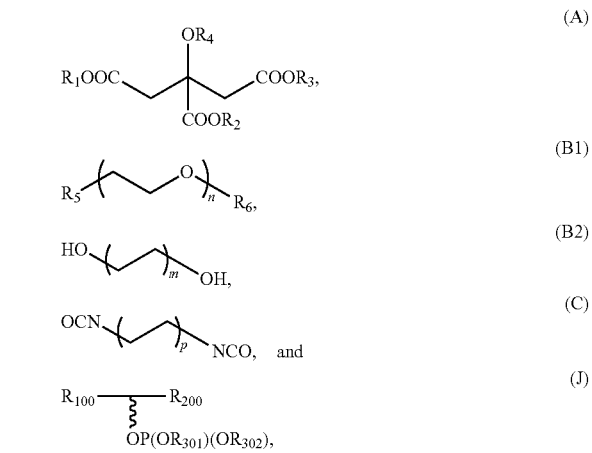

wherein $R_1$, $R_2$, and $R_3$ are independently —H, —CH$_3$, —CH$_2$CH$_3$, or M+;
$R_4$ is —H;
$R_5$ is —H, —OH, —OCH$_3$, —OCH$_2$CH$_3$, —CH$_3$, or —CH$_2$CH$_3$;

$R_6$ is —H, —$CH_3$, or —$CH_2CH_3$;

$M^+$ is a cation such as $Na^+$ or $K^+$;

n and m are independently integers ranging from 1 to 20;

p is an integer ranging from 1 to 10; and $R_{100}$, $R_{200}$, $R_{301}$, and $R_{302}$ are as described above in the context of Formula (I).

For example, in some instances, $R_1$, $R_2$, and $R_3$ are —H, or —$CH_2CH_3$, $R_5$ is —OH, $R_6$ is —H, n is 2 to 6, m is 2 to 8, and p is 2 to 6.

Further, the monomers of Formula (A), (B1), (B2), (C), and (J) can be used in any ratio not inconsistent with the objectives of the present disclosure. In addition, altering the ratios of monomers can, in some embodiments, alter the bone regeneration properties, the biodegradability, the mechanical strength, and/or other properties of the polymer formed from the monomers.

In some embodiments, the molar ratio of monomer (A) to monomer (B1) or monomer (B2) is between about 1:10 and about 10:1 or between about 1:5 and about 5:1. In some embodiments, the molar ratio of monomer (A) to monomer (B1) or monomer (B2) is between about 1:4 and about 4:1. In some embodiments, the molar ratio is about 5:6.

In some embodiments, the molar ratio of monomer (B1) or monomer (B2) to monomer (J) is between about 1:20 and about 20:1 or between about 1:10 and about 10:1. In some embodiments, the molar ratio of monomer (B1) or monomer (B2) to monomer (J) is between about 1:5 and about 5:1. In some embodiments, the molar ratio is about 6:1.

In some embodiments, the molar ratio of monomer (A) to monomer (J) is between about 1:20 and about 20:1 or between about 1:10 and about 10:1. In some embodiments, the molar ratio of monomer (A) to monomer (J) is between about 1:3 and about 3:1. In some embodiments, the molar ratio is about 5:1.

In some embodiments, the molar ratio of monomer (C) to monomer (J) is between about 1:20 and about 20:1 or between about 1:10 and about 10:1. In some embodiments, the molar ratio of monomer (C) to monomer (J) is between about 1:3 and about 3:1. In some embodiments, the molar ratio is about 1:2.

Further, in some embodiments described herein, a monomer of Formula (B1) or (B2) can be replaced by an alcohol that does not have the formula of Formula (B1) or (B2). For example, in some embodiments, an unsaturated alcohol or an unsaturated polyol can be used.

In some embodiments, a phosphate-containing polymer in a graft or scaffold utilized in a method described herein is formed from one or more monomers of Formula (A), one or more monomers of Formula (B1) or (B2), one or more monomers of Formula (D1) or (D2), and one or more monomers of Formula (J):

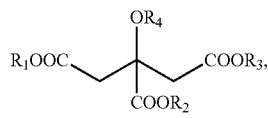

(A)

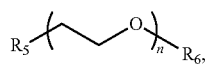

(B1)

(B2)

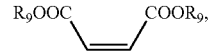

(D1)

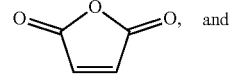

(D2)

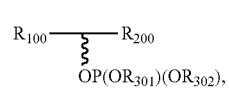

(J)

wherein $R_1$, $R_2$, and $R_3$ are each independently —H, —$CH_3$, —$CH_2CH_3$, or $M^+$, $R_4$ is —H;

$R_5$ is —H, —OH, —$OCH_3$, —$OCH_2CH_3$, —$CH_3$, or —$CH_2CH_3$;

$R_6$ is —H, —$CH_3$, or —$CH_2CH_3$;

$R_9$ is —H, —$CH_3$, or —$CH_2CH_3$;

$M^+$ is a cation such as $Na^+$ or $K^+$;

n and m are each independently integers ranging from 1 to 20 or from 1 to 100, and $R_{100}$, $R_{200}$, $R_{301}$, and $R_{302}$ are as described above in the context of Formula (I).

Further, the monomers of Formula (A), (B1), (B2), (D1), (D2), and (J) can be used in any ratio not inconsistent with the objectives of the present disclosure. In addition, altering the ratios of monomers can, in some embodiments, alter the properties of the phosphate-containing polymer formed from the monomers.

In some embodiments, the molar ratio of monomer (A) to monomer (B1) or monomer (B2) is between about 1:10 and about 10:1 or between about 1:5 and about 5:1. In some embodiments, the molar ratio of monomer (A) to monomer (B1) or monomer (B2) is between about 1:4 and about 4:1. In some embodiments, the molar ratio is about 5:6.

In some embodiments, the molar ratio of monomer (B1) or monomer (B2) to monomer (J) is between about 1:20 and about 20:1 or between about 1:10 and about 10:1. In some embodiments, the molar ratio of monomer (B1) or monomer (B2) to monomer (J) is between about 1:5 and about 5:1. In some embodiments, the molar ratio is about 6:1.

In some embodiments, the molar ratio of monomer (A) to monomer (J) is between about 1:20 and about 20:1 or between about 1:10 and about 10:1. In some embodiments, the molar ratio of monomer (A) to monomer (J) is between about 1:3 and about 3:1. In some embodiments, the molar ratio is about 5:1.

In some embodiments, the molar ratio of monomer (D) (the combination of (D1) and (D2)) to monomer (J) is between about 1:20 and about 20:1 or between about 1:10 and about 10:1. In some embodiments, the molar ratio of monomer (D) to monomer (J) is between about 1:3 and about 3:1. In some embodiments, the molar ratio is about 1:2.

In some embodiments, a phosphate-containing polymer of a graft or scaffold utilized in a method described herein is formed from one or more monomers of Formula (A) and one or more monomers of Formula (B1), (B2) or (B3), one or more monomers of Formula (E), and one or more monomers of Formula (J):

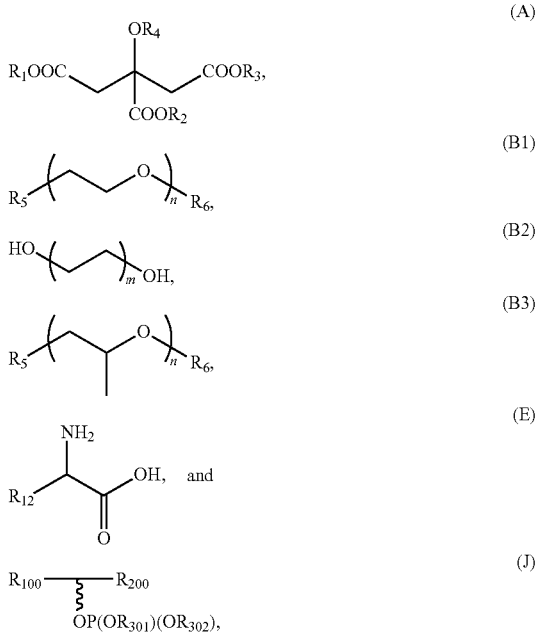

wherein $R_1$, $R_2$, and $R_3$ are independently —H, —CH$_3$, —CH$_2$CH$_3$, or M$^+$;
$R_4$ is —H;
$R_5$ is —H, —OH, —OCH$_3$, —OCH$_2$CH$_3$, —CH$_3$, or —CH$_2$CH$_3$;
$R_6$ is —H, —CH$_3$, or —CH$_2$CH$_3$;
$R_{12}$ is a side chain or "R group" of one of the 22 "standard" or proteinogenic amino acids provided above;
M$^+$ is a cation such as Na$^+$ or K$^+$;
n and m are independently integers ranging from 1 to 20; and
$R_{100}$, $R_{200}$, $R_{301}$, and $R_{302}$ are as described above in the context of Formula (I).

In some cases, for example, $R_{12}$ is —CH$_2$SH (for E=cysteine) or —CH$_2$OH (for E=serine). Further, in some embodiments, $R_1$, $R_2$, and $R_3$ are —H, $R_5$ is —OH, and $R_6$ is —H.

Moreover, the monomers of Formula (A), (B1), (B2), (B3), (E), and (J) can be used in any ratio not inconsistent with the objectives of the present disclosure. In addition, altering the ratios of monomers can, in some embodiments, alter one or more properties of the phosphate-containing polymer formed from the monomers.

In some embodiments, the ratio of monomer (A) to monomer (B1), monomer (B2), or monomer (B3) is between about 1:10 and about 10:1 or between about 1:5 and about 5:1. In some embodiments, the ratio of monomer (A) to monomer (B1), monomer (B2), or monomer (B3) is between about 1:4 and about 4:1. In some cases, the ratio is about 1:1. Further, in some embodiments, the ratio of monomer (A) to monomer (E) is between about 1:10 and about 10:1.

In some embodiments, the molar ratio of monomer (B1) or monomer (B2) or monomer (B3) (or the combined monomers (B1)-(B3)) to monomer (J) is between about 1:20 and about 20:1 or between about 1:10 and about 10:1. In some embodiments, the molar ratio of monomer (B1) or monomer (B2) to monomer (J) is between about 1:5 and about 5:1. In some embodiments, the molar ratio is about 6:1.

In some embodiments, the molar ratio of monomer (A) to monomer (J) is between about 1:20 and about 20:1 or between about 1:10 and about 10:1. In some embodiments, the molar ratio of monomer (A) to monomer (J) is between about 1:3 and about 3:1. In some embodiments, the molar ratio is about 5:1.

In some embodiments, the molar ratio of monomer (E) to monomer (J) is between about 1:20 and about 20:1 or between about 1:10 and about 10:1. In some embodiments, the molar ratio of monomer (E) to monomer (J) is between about 1:3 and about 3:1. In some embodiments, the molar ratio is about 1:2.

In some embodiments, a phosphate-containing polymer of a composition described herein comprises a phosphate-containing polymer formed from one or more monomers of Formula (A), one or more monomers of Formula (B1) or (B2), one or more monomers of Formula (F), and one or more monomers of Formula (J):

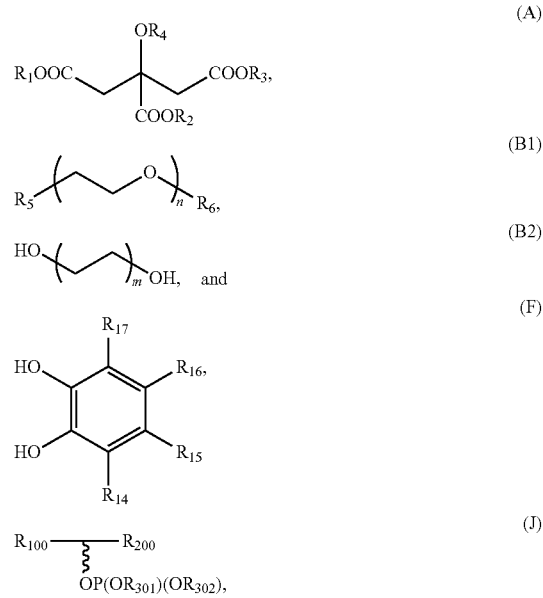

wherein $R_1$, $R_2$, and $R_3$ are independently —H, —CH$_3$, —CH$_2$CH$_3$, or M$^+$;
$R_4$ is —H;
$R_5$ is —H, —OH, —OCH$_3$, —OCH$_2$CH$_3$, —CH$_3$, or —CH$_2$CH$_3$;
$R_6$ is —H, —CH$_3$, or —CH$_2$CH$_3$;
$R_{14}$, $R_{15}$, $R_{16}$, and $R_{17}$ are independently —H, —CH$_2$(CH$_2$)$_x$NH$_2$, —CH$_2$(CHR$_{18}$)NH$_2$, or —CH$_2$(CH$_2$)$_x$COOH;
$R_{18}$ is —COOH or —(CH$_2$)$_y$COOH;
M$^+$ is a cation such as Na$^+$ or K$^+$;
n and m are independently integers ranging from 1 to 20;
x is an integer ranging from 0 to 20;
y is an integer ranging from 1 to 20; and
$R_{100}$, $R_{200}$, $R_{301}$, and $R_{302}$ are as described above in the context of Formula (I).

In some embodiments, $R_2$ is —H. In addition, in some cases, three of $R_{14}$, $R_{15}$, $R_{16}$, and $R_{17}$ are —H. Further, in some embodiments, $R_{14}$ and $R_{17}$ specifically are —H. In some cases, a monomer of Formula (F) comprises dopamine, L-DOPA, D-DOPA, or 3,4-dihydroxyhydrocinnamic acid. Moreover, in some embodiments, a monomer of Formula (F) is coupled to the backbone of the polymer through an amide bond. In other embodiments, a monomer of Formula (F) is coupled to the backbone of the polymer through an ester bond.

Further, in some embodiments, a monomer of Formula (B1) or (B2) can be replaced by an alcohol that does not have the formula of Formula (B1) or (B2). For example, in some embodiments, an unsaturated alcohol or an unsaturated polyol can be used.

Moreover, the monomers of Formula (A), (B1), (B2), (F), and (J) can be used in any ratio not inconsistent with the objectives of the present disclosure. In addition, altering the ratios of monomers can, in some embodiments, alter one or more properties of the phosphate-containing polymer formed from the monomers. In some embodiments, the ratio of monomer (A) to monomer (B1) or monomer (B2) is between about 1:10 and about 10:1 or between about 1:5 and about 5:1. In some embodiments, the ratio of monomer (A) to monomer (B1) or monomer (B2) is between about 1:4 and about 4:1. In some cases, the ratio is about 1:1. Further, in some embodiments, the ratio of monomer (A) to monomer (F) is between about 1:10 and about 10:1.

In some embodiments, the molar ratio of monomer (B1) or monomer (B2) to monomer (J) is between about 1:20 and about 20:1 or between about 1:10 and about 10:1. In some embodiments, the molar ratio of monomer (B1) or monomer (B2) to monomer (J) is between about 1:5 and about 5:1. In some embodiments, the molar ratio is about 6:1.

In some embodiments, the molar ratio of monomer (A) to monomer (J) is between about 1:20 and about 20:1 or between about 1:10 and about 10:1. In some embodiments, the molar ratio of monomer (A) to monomer (J) is between about 1:3 and about 3:1. In some embodiments, the molar ratio is about 5:1.

In some embodiments, the molar ratio of monomer (F) to monomer (J) is between about 1:20 and about 20:1 or between about 1:10 and about 10:1. In some embodiments, the molar ratio of monomer (F) to monomer (J) is between about 1:3 and about 3:1. In some embodiments, the molar ratio is about 1:2.

In still other cases, a phosphate-containing polymer described herein is formed from one or more monomers of Formula (A) above; one or more monomers of Formula (B1), (B2), or (B3) above; one or more monomers of Formula (J) above; and one or more monomers of Formula (G1), (G2), (G3), or (G4):

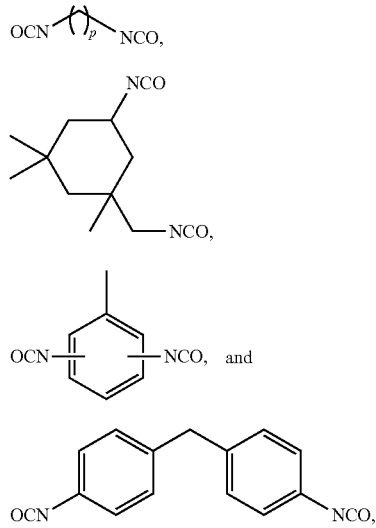

wherein
p is an integer ranging from 1 to 10.

Moreover, the monomers of Formula (A), (B1), (B2), (B3), (G1), (G2), (G3), (G4), and (J) can be used in any ratio not inconsistent with the objectives of the present disclosure. In addition, altering the ratios of monomers can, in some embodiments, alter the biodegradability, the luminescent intensity, the mechanical strength, and/or other properties of the polymer formed from the monomers. In some embodiments, the ratio of monomer (A) to monomer (B1), (B2), or (B3) is between about 1:10 and about 10:1 or between about 1:5 and about 5:1. In some embodiments, the ratio of monomer (A) to monomer (B) is between about 1:4 and about 4:1. In some embodiments, the ratio is about 1:1. Further, in some embodiments, the ratio of monomer (A) to monomer (G) is between about 1:10 and about 10:1. In some embodiments, the ratio of monomer (A) to monomer (G) is about 1:1.

In still other embodiments, a phosphate-containing polymer described herein is formed from one or more monomers of Formula (A1) above; optionally one or more monomers of Formula (A2) above; one or more monomers of Formula (B1), (B2), and/or (B3) above; one or more monomers of Formula (J) above; and one or more monomers of Formula (H1) or (H2):

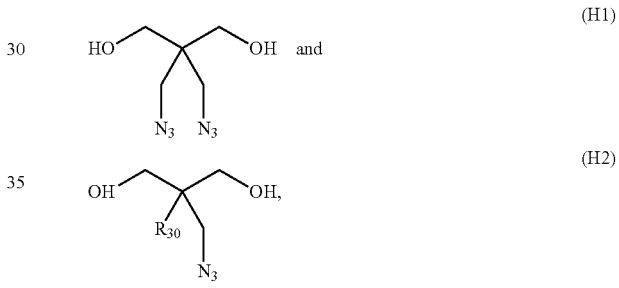

wherein
$R_{30}$ is —$CH_3$ or —$CH_2CH_3$.

Further, in some embodiments, a phosphate-containing polymer described herein is formed from one or more monomers of Formula (A1) above; optionally one or more monomers of Formula (A2) above; one or more monomers of Formula (B1), (B2), and/or (B3) above; one or more monomers of Formula (J) above; and one or more monomers of Formula (I1), (I2), (I3), (I4), (I5), or (I6):

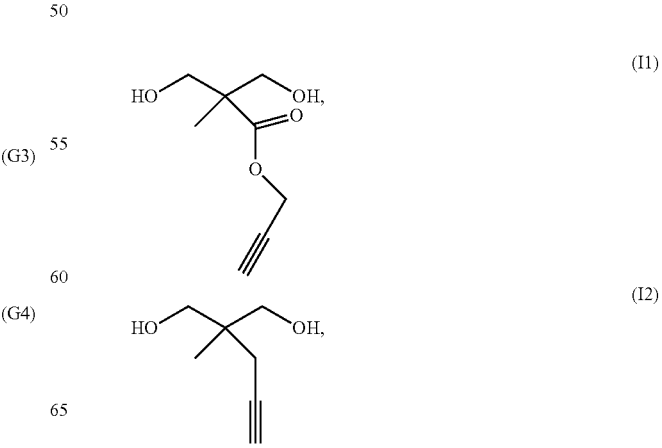

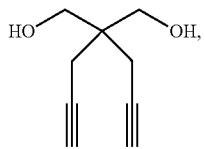

(I3)

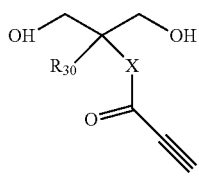

(I4)

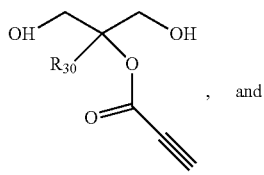

(I5)

, and

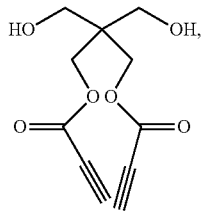

(I6)

wherein
$R_{30}$ is —$CH_3$ or —$CH_2CH_3$; and
X is —NH— or —O—.

Additionally, in some embodiments, a polymer described herein can be functionalized with a bioactive species. In some cases, the polymer is formed from an additional monomer comprising the bioactive species. Moreover, such an additional monomer can comprise one or more alkyne and/or azide moieties. For example, in some instances, a polymer described herein is formed from one or more monomers comprising a peptide, polypeptide, nucleic acid, or polysaccharide, wherein the peptide, polypeptide, nucleic acid, or polysaccharide is functionalized with one or more alkyne and/or azide moieties. In some cases, the bioactive species of a polymer described herein is a growth factor or signaling molecule. Further, a peptide can comprise a dipeptide, tripeptide, tetrapeptide, or a longer peptide. As described further hereinafter, forming a polymer from such a monomer, in some embodiments, can provide additional biological functionality to a composition described herein.

In addition, in some embodiments, a composition comprises a plurality of polymers described herein. In some instances, the polymers are selected to be reactive with one another through a click chemistry reaction scheme. In some cases, for example, a composition described herein comprises a first polymer formed from one or more monomers of Formula (A); one or more monomers of Formula (B1), (B2), or (B3); one or more monomers of Formula (J); and one or more monomers comprising one or more alkyne moieties; and further comprises a second polymer formed from one or more monomers of Formula (A); one or more monomers of Formula (B1), (B2), or (B3); one or more monomers of Formula (J); and one or more monomers comprising one or more azide moieties. Thus, in some such embodiments, a composition described herein can comprise an azide-alkyne cycloaddition product, such as a 1,4 or 1,5-triazole ring. In this manner, a first polymer and a second polymer of a composition described herein can form a polymer network by forming one or more azide-alkyne cycloaddition products to serve as cross-links of the polymer network.

Such a polymer network can have a high cross-linking density. "Cross-linking density," for reference purposes herein, can refer to the number of cross-links between polymer backbones or the molecular weight between cross-linking sites, calculated as described hereinafter. Further, in some embodiments, the cross-links of a polymer network described herein comprise azide-alkyne cycloaddition product cross-links. Cross-links may also include ester bonds formed by the esterification or reaction of one or more pendant carboxyl or carboxylic acid groups with one or more pendant hydroxyl groups of adjacent polymer backbones. In some embodiments, a polymer network described herein has a cross-linking density of at least about 500, at least about 1000, at least about 5000, at least about 7000, at least about 10,000, at least about 20,000, or at least about 30,000 $mol/m^3$. In some cases, the cross-linking density is between about 5000 and about 40,000 or between about 10,000 and about 40,000 $mol/m^3$.

It is also possible to form a polymer network using a click chemistry reaction scheme that does not necessarily form azide-alkyne cycloaddition products. For instance, in some cases, one or more monomers comprising an alkyne and/or azide moiety described herein can be at least partially replaced by one or more monomers comprising a different moiety that can participate in a click chemistry reaction scheme. For example, in some embodiments, a polymer or polymer network is formed from the reaction of one or more monomers comprising a thiol moiety with one or more monomers comprising an alkene (or alkyne) moiety through a thiol-ene/yne click reaction. Such a thiol-ene/yne click reaction can comprise the addition of an S—H bond across a carbon-carbon double bond or triple bond by a free radical or ionic mechanism. More generally, in some cases, a polymer described herein can be formed from one or more monomers of Formula (A); one or more monomers of Formula (B1), (B2), or (B3); one or more monomers of Formula (J); and one or more monomers comprising one or more first moieties operable to participate in a click chemistry reaction and/or one or more second moieties operable to participate in the same click chemistry reaction, where the first and second moieties differ. Any click chemistry reaction not inconsistent with the objectives of the present disclosure may be used. In some instances, the click chemistry reaction comprises a [3+2] cycloaddition such as a Huisgen alkyne-azide cycloaddition; a thiol-ene/yne reaction; a Diels-Alder reaction; an inverse electron demand Diels-Alder reaction; a [4+1] cycloaddition such as the cycloaddition reaction of an isocyanide with a tetrazine; or a nucleophilic substitution reaction involving a strained ring such as an epoxy or aziridine ring. Not intending to be bound by theory, it is believed that the use of a click chemistry reaction scheme to provide cross-linking in a polymer network can, in some cases, improve the mechanical strength of a polymer network without sacrificing pendant citric acid or phospho-amino acid carboxyl moieties for other purposes, such as hydroxyapatite (HA) calcium chelation.

As described above, a phosphate-containing polymer described herein can be a condensation polymerization reaction product of the identified monomers and/or other species. In some such embodiments, the reaction product forms an alternating copolymer or a statistical copolymer of the comonomers. Moreover, in some cases, the amount or ratio of a comonomer or other reactant comprising a phosphate moiety can be selected to provide or tune a desired property or effect to the polymer. For example, in some embodiments, the amount or ratio of a comonomer or other reactant comprising a phosphate moiety can be selected to provide a desired metabonegenic effect to the polymer, e.g. promoting bone regeneration, including bone mineralization. Other properties of a composition described herein can also be tuned by varying one or more of the mole percent or weight percent of a phosphate moiety in a phosphate-containing polymer. For example, tunable properties, in certain embodiments, can comprise or include one or more of: the metabonegenic properties of a polymer, the biodegradability of a polymer, alkaline phosphatase (ALP) promoting properties, and the osteopontin (OPN) promoting properties of a polymer.

Additionally, in some cases, a phosphate-containing polymer described herein comprises at least about 30 mole percent, at least about 40 mole percent, or at least about 50 mole percent citrate moiety, based on the total number of moles of the co-monomers of the polymer. In some embodiments, a polymer described herein comprises between about 30 mole percent and about 70 mole percent, between about 30 mole percent and about 60 mole percent, between about 30 mole percent and about 50 mole percent, between about 35 mole percent and about 60 mole percent, between about 35 mole percent and about 55 mole percent, between about 40 mole percent and about 70 mole percent, between about 40 mole percent and about 60 mole percent, or between about 40 mole percent and about 55 mole percent citrate moiety, based on the total number of moles of the co-monomers of the polymer.

Similarly, in some cases, a phosphate-containing polymer described herein comprises at least about 1 weight percent, at least about 5 weight percent, or at least about 10 weight percent, at least about 15 weight percent, at least about 20 weight percent, or at least about 30 weight percent phosphate moiety, based on the total weight of the polymer. In some embodiments, a phosphate-containing polymer described herein comprises between about 1 weight percent and about 50 weight percent, between about 1 weight percent and about 30 weight percent, between about 2 weight percent and about 20 weight percent, between about 3 weight percent and about 15 weight percent, between about 4 weight percent and about 10 weight percent phosphate moiety, based on the total weight of the polymer.

Additionally, in some cases, one or more properties of a phosphate-containing polymer may be tuned based on the amount of the phosphate moiety as well as on one or more other features of the chemical structure of the polymer. Moreover, one or more properties may be tunable independently of one or more other properties. For example, in some cases, the osteo-promotive effects and/or degradation rate of a polymer described herein can be tuned. Such tunability can provide advantages to a composition of a graft or scaffold utilized in a method described herein. The structure and chemical composition of some phosphate-containing polymers and compositions described herein can be selected to satisfy requirements, such as mechanical and tissue regeneration requirements, including bone regeneration to achieve one or more goals of the disclosure.

Additionally, a phosphate-containing polymer described herein can have at least one ester bond in the backbone of the polymer. In some cases, a polymer has a plurality of ester bonds in the backbone of the polymer, such as at least three ester bonds, at least four ester bonds, or at least five ester bonds. In some embodiments, a polymer described herein has between two ester bonds and fifty ester bonds in the backbone of the polymer. Polymers having one or more ester bonds in the backbone of the polymer can be hydrolyzed in a biological or other aqueous environment to release free citric acid or citrate and free phosphate in addition to other components. Not intending to be bound by theory, it is believed that the presence of phosphate in a biological environment can contribute to increased ALP expression and bone ossification, which may promote and/or accelerate bone regeneration at a bone site in need thereof.

Further, phosphate-containing polymers having a structure described herein, in some cases, can be biodegradable. A biodegradable polymer, in some embodiments, degrades in vivo to non-toxic components which can be cleared from the body by ordinary biological processes. In some embodiments, a biodegradable polymer completely or substantially completely degrades in vivo over the course of about 90 days or less, about 60 days or less, or about 30 days or less, where the extent of degradation is based on percent mass loss of the biodegradable polymer, and wherein complete degradation corresponds to 100% mass loss. Specifically, the mass loss is calculated by comparing the initial weight ($W_0$) of the polymer with the weight measured at a pre-determined time point ($W_t$) (such as 30 days), as shown in equation (1):

$$\text{Mass loss (\%)} = \frac{(W_0 - W_t)}{W_0} \times 100. \tag{1}$$

Additionally, in some embodiments, a polymer network comprising a phosphate-containing polymer described herein can further comprise a crosslinker. Any crosslinker not inconsistent with the objectives of the present disclosure may be used. In some cases, for example, a crosslinker comprises one or more olefins or olefinic moieties that can be used to crosslink phosphate-containing polymers comprising ethyleneically unsaturated moieties. In some embodiments, a crosslinker comprises an acrylate or polyacrylate, including a diacrylate. In other cases, a crosslinker comprises one or more of 1,3-butanediol diacrylate, 1,6-hexanediol diacrylate, glycerol 1,3-diglycerolate diacrylate, di(ethylene glycol) diacrylate, poly(ethylene glycol) diacrylate, poly(propylene glycol) diacrylate, and propylene glycol glycerolate diacrylate. In still other instances, a crosslinker comprises a nucleic acid, including DNA or RNA. In some embodiments, a crosslinker comprises a "click chemistry" reagent, such as an azide or an alkyne. In some embodiments, a crosslinker comprises an ionic cross linker. For instance, in some cases, a phosphate-containing polymer is crosslinked with a multivalent metal ion, such as a transition metal ion. In some embodiments, a multivalent metal ion used as a crosslinker of the polymer comprises one or more of Fe, Ni, Cu, Zn, or Al, including in the +2 or +3 state.

In addition, a crosslinker described herein can be present in a graft or scaffold in any amount not inconsistent with the objectives of the present invention. For example, in some embodiments, a crosslinker is present in a composition for a graft or scaffold in an amount between about 5 weight percent and about 50 weight percent, between about 5 weight percent and about 40 weight percent, between about 5 weight percent and about 30 weight percent, between about 10 weight percent and about 40 weight percent, between about 10 weight percent and about 30 weight percent, or between about 20 weight percent and about 40 weight percent, based on the total weight of the composition.

Thus, in some embodiments, a graft or scaffold utilized in a method described herein comprises a phosphate-containing polymer that is crosslinked to form a polymer network. A polymer network, in some embodiments, comprises a hydrogel. A hydrogel, in some cases, comprises an aqueous continuous phase and a polymeric disperse or discontinuous phase. Further, in some embodiments, a crosslinked polymer network described herein is not water soluble.

Polymers such as phosphate-containing polymers described herein can be prepared in any manner not inconsistent with the objectives of the present disclosure. In some cases, for instance, a polymer described herein is prepared by one or more polycondensation reactions. Further, in some embodiments, a polycondensation reaction can be followed by cross linking of the polymer. As described further herein, such cross linking can be thermal cross linking or photoinitiated cross linking such as ultraviolet (UV) cross linking.

Various components of compositions which may form part or all of a graft or scaffold utilized in a composition for promoting bone regeneration have been described herein. It is to be understood that a composition according to the present disclosure can comprise any combination of components and features not inconsistent with the objectives of the present disclosure. For example, in some cases, a composition forming part or all of a graft or scaffold utilized in a composition described herein can comprise a combination, mixture, or blend of polymers described herein. Additionally, in some embodiments, such a combination, mixture, or blend can be selected to provide a composition, graft or scaffold having any osteo-promoting property, biodegradability, mechanical property, and/or chemical functionality described herein.

Further, one or more polymers such as one or more phosphate-containing polymers can be present in a composition forming part or all of a graft or scaffold utilized in a composition described herein in any amount not inconsistent with the objectives of the present disclosure. In some cases, a composition, graft or scaffold consists or consists essentially of the one or more polymers such as the one or more phosphate-containing polymers. In other instances, a composition, graft or scaffold comprises up to about 95 weight percent, up to about 90 weight percent, up to about 80 weight percent, up to about 70 weight percent, up to about 60 weight percent, up to about 50 percent, or up to about 40 weight percent phosphate-containing polymer, based on the total weight of the composition, graft or scaffold. In some embodiments, the balance of a composition, graft or scaffold described herein can be water, an aqueous solution, and/or a particulate material, as described further herein below.

As described herein, grafts or scaffolds can further comprise a particulate inorganic material in the graft or scaffold. Any particulate inorganic material not inconsistent with the objectives of the present disclosure may be used. In some cases, the particulate inorganic material comprises one or more of hydroxyapatite, tricalcium phosphate (including α- and β-tricalcium phosphate), biphasic calcium phosphate, bioglass, ceramic, magnesium powder, magnesium alloy, and decellularized bone tissue particles. Other particulate materials may also be used.

In addition, a particulate inorganic material described herein can have any particle size and/or particle shape not inconsistent with the objectives of the present disclosure. In some embodiments, for instance, a particulate material has an average particle size in at least one dimension of less than about 1000 μm, less than about 800 μm, less than about 500 μm, less than about 300 μm, less than about 100 μm, less than about 50 μm, less than about 30 μm, or less than about 10 μm. In some cases, a particulate material has an average particle size in at least one dimension of less than about 1 μm, less than about 500 nm, less than about 300 nm, less than about 100 nm, less than about 50 nm, or less than about 30 nm. In some instances, a particulate material has an average particle size recited herein in two dimensions or three dimensions. Moreover, a particulate material can be formed of substantially spherical particles, plate-like particles, needle-like particles, or a combination thereof. Particulate materials having other shapes may also be used.

A particulate inorganic material can be present in a composition (such as a graft or scaffold) described herein in any amount not inconsistent with the objectives of the present disclosure. For example, in some cases, a composition utilized in a graft or scaffold described herein comprises up to about 30 weight percent, up to about 40 weight percent, up to about 50 weight percent, up to about 60 weight percent, or up to about 70 weight percent particulate material, based on the total weight of the composition. In some instances, a composition comprises between about 1 and about 70 weight percent, between about 10 and about 70 weight percent, between about 15 and about 60 weight percent, between about 25 and about 65 weight percent, between about 25 and about 50 weight percent, between about 30 and about 70 weight percent, between about 30 and about 50 weight percent, between about 40 and about 70 weight percent, or between about 50 and about 70 weight percent particulate material, based on the total weight of the composition. For example, in some cases, a composition comprising a polymer network described herein comprises up to about 50 weight percent hydroxyapatite.

II. Methods of Promoting and/or Accelerating Bone Regeneration

In another aspect, methods of promoting and/or accelerating bone regeneration are described herein. Methods described herein can use one or more compositions described above. For example, in one embodiment, a method of promoting and/or accelerating bone regeneration comprises delivering a biodegradable scaffold to a bone site, the scaffold comprising a citrate component, a phosphate component, and a particulate inorganic material. The biodegradable scaffold can be any graft or scaffold as described above. The phosphate component can be any phosphate containing-polymer or phosphate-containing monomer as described above. Similarly, the citrate component can be any citrate-containing polymer or citrate-containing monomer as described above. In addition, the particulate inorganic material can be any particulate inorganic material as described above.

Moreover, in some embodiments, the biodegradable scaffold is itself microparticulate. The microparticulate scaffold include or contain a liquid, or be substantially "dry" or free of liquid. Moreover, such a liquid that is included in (or mostly excluded from) a scaffold can be any liquid not inconsistent with the objectives of the present disclosure. In some embodiments, for instance, the liquid is water or an aqueous solution or mixture, such as a salt solution or saline. Moreover, in some cases, the liquid can be a "carrier" liquid for introducing other species to the scaffold. For example, in some embodiments, the liquid comprises one or more biomolecules, bioactive materials, or other biomaterials, as described further below. In some cases, the liquid comprises a hyaluronate or hyaluronic acid. In some instances, the liquid comprises blood or plasma.

Additionally, the microparticulate scaffold, in some embodiments, is a paste. More particularly, such a paste can include a microparticulate scaffold that includes a liquid (as opposed to being a "dry" material). Such a "paste" can be a viscous or shape-stable material (at standard temperature and pressure conditions) and can have a viscosity suitable for handling or manipulation, such as scooping, with a microspatula. For example, in some embodiments, the paste has a dynamic viscosity of at least $1.0 \times 10^4$ centipoise (cP), at least $5.0 \times 10^4$, or at least $1.0 \times 10^5$. In other embodiments, the paste has a viscosity between about $1.0 \times 10^4$ cP and $1.0 \times 10^7$ cP, between about $1.0 \times 10^5$ cP and $1.0 \times 10^6$ cP, or between about $1.0 \times 10^6$ cP and $1.0 \times 10^7$ cP. The liquid component of a paste, in some instances, is an isotonic solution, and the paste is a biologically sterile paste. For example, in some embodiments, a paste described herein, can be formed from a salt solution, such as saline, or other biologically active solution such as sodium hyaluronate or blood. In some cases, the biologically active solution can comprise additional biological molecules or factors suitable to promote and/or accelerate bone regeneration. For example, the solution can comprise growth factors or signaling molecules, such as osteogenic factors. Non-limiting examples of biological factors that may be used in some embodiments described herein include osteopontin (OPN), osteocalcin (OCN), bone morphogenetic protein-2 (BMP-2), transforming growth factor β3 (TGFβ3), stromal cell-derived factor-1α (SDF-1α), erythropoietin (Epo), vascular endothelial growth factor (VEGF), Insulin-like Growth Factor-1 (IGF-1), platelet derived growth factor (PDGF), fibroblast growth factor (BGF), nerve growth factor (NGF), neurotrophin-3 (NT-3), and glial cell-derived neurotrophic factor (GDNF). Other therapeutic proteins and chemical species may also be used.

Moreover, in some cases, the biodegradable scaffold used in the methods described herein is a polymer network. The polymer network can comprise any combination of polymers and/or co-polymers as described above. Further, in some embodiments, the polymer network comprises particulate inorganic material. For example, polymers as described above, can be cross-linked to encapsulate or otherwise bond to the particulate inorganic material. Cross-linking can be performed, for example, by exposing the polymer to heat and/or UV light.

In other embodiments, the scaffold can have additional desirable properties suitable for use in methods described herein. For example, the biodegradable scaffold, in some embodiments, has a rough, ridged, or undulating surface morphology. In some embodiments, the surface morphology comprises nano-sized features. For example, the rough, ridged or undulating surfaces can be nanoscale or have nanoscale topographical features (e.g., having a size in at least one dimension of up to 500 nm, up to 100 nm, or up to 50 nm). Such a morphology can promote attachment of cells to the scaffold and can promote bone mineralization. In some embodiments, the surface roughness of a scaffold described herein, in some cases, corresponds to an $R_a$ value of between about 50 and 1000, between 50 and 500, between 100 and 500, between 100 and 400, or between 500 and 1000 μm. In some cases, the surface roughness of a scaffold described herein corresponds to an $R_a$ value of about 200, about 500, or about 1000 μm. In still other embodiments, a scaffold described herein is luminescent. In some cases, such luminescence is photoluminescence and can be observed by exposing the scaffold to a suitable wavelength of light, such as light having a peak or average wavelength between 400 nm and 600 nm. Moreover, in some embodiments, the luminescence intensity of a luminescent scaffold, measured in arbitrary or relative units, can be used as a measure of degradation of the scaffold over time, thereby indicating biodegradability or clearance from a site, such as a bone site. In further embodiments, the biodegradable scaffold has relatively high compressive strength. For example, in some cases, the compressive strength of a graft or scaffold used in methods described herein can be between about 100 and 300 MPa, between about 150 and 250 MPa, or between about 175 and 225 MPa. In some cases, the compressive strength is about 170 or 200 MPa.

In some embodiments, the graft or scaffold used in a method described herein delivers 10 to 1,000 μM phosphate component to the bone site. Delivery of the phosphate component can be in monomer, polymer, and/or free form. For example, the phosphate component can be a phosphate-containing monomer or polymer comprising a phosphate pendant group, as described above. In other embodiments, the phosphate can be a free phosphate, for example, a phosphate in solution. In some cases, a scaffold described herein can deliver between 100 and 1000 μM, between 500 and 1000 μM, between 10 and 100 μM, between 50 and 100 μM, between 1 and 100 μM, between 10 and 50 μM, between 1 and 50 μM, or between 10 and 30 μM phosphate component (or phosphate, as defined in Formula (I)) to the bone site.

In another embodiment, the scaffold delivers 100 to 2,000 μM citric acid, citrate, or ester of a citric acid to the bone site. Delivery of the citric acid, citrate, or ester of a citric acid component can be in monomer, polymer, and/or free form. For example, the citric acid, citrate, or ester of a citric acid can be a citrate-containing polymer comprising a citric acid, citrate, or ester of a citric acid. In other embodiments, the citric acid, citrate, or ester of a citric acid can be a solution. For example, the scaffold can deliver between 100 and 1000 μM, between 100 and 500 μM, between 100 and 300 μM, between 100 and 200 μM, between 200 and 500 μM, or between 200 and 2,000 μM citric acid, citrate, or ester of a citric acid to the bone site. Such delivery of citrate can be in addition to the phosphate delivery described above.

In still further embodiments, the ratio of (i) citrate component to (ii) phosphate component can be between 2:1 and 10:1. For example, the ratio of (i) citrate component to (ii) phosphate component can be between 2:1 and 5:1, between 3:1 and 8:1, or between 3:1 and 6:1, between 3:1 and 5:1. In some cases the ratio is about 5:1.

Methods of promoting and/or accelerating bone regeneration, as described herein, in some embodiments, can further comprise delivering stem cells to the bone site. For example a graft or scaffold delivered to a bone site consistent with methods described herein, in some embodiments, can be delivered to a bone site that is seeded with or contains a biofactor or seed cell. In some embodiments, a graft or scaffold can be seeded with a biofactor or cell such as mesenchymal stem cells (MSCs). In certain other embodiments, a graft or scaffold can be delivered to a bone site in addition to or in combination with an autologous bone graft. Biofactor or cells utilized in combination with a graft or scaffold described herein may be isolated or sourced from any host or by any means not inconsistent with the objectives of the present invention. For example, in some embodiments, the biofactor or cells can be harvested or isolated from the individual receiving the graft or scaffold. In certain other embodiments, the biofactor or cells can be harvested or isolated from a different individual, such as a compatible donor. In some other cases, the biofactor or cells can be grown or cultured from an individual, either the graft or scaffold recipient or another compatible individual. In certain other cases, the graft or scaffold is unseeded with a biofactor or cell upon disposition within, on, or near the bone site. Non-limiting examples of seed cells that may be used in some embodiments described herein include mesenchymal stem cells (MSCs), bone marrow stromal cells (BMSCs), induced pluripotent stem (iPS) cells, endothelial progenitor cells, and hematopoietic stem cells (HSCs). Other cells may also be used. Non-limiting examples of biofactors that may be used in some embodiments described herein include bone morphogenetic protein-2 (BMP-2), transforming growth factor β3 (TGFβ3), stromal cell-derived factor-1α (SDF-1α), erythropoietin (Epo), vascular endothelial growth factor (VEGF), Insulin-like Growth Factor-1 (IGF-1), platelet derived growth factor (PDGF), fibroblast growth factor (BGF), nerve growth factor (NGF), neurotrophin-3 (NT-3), and glial cell-derived neurotrophic factor (GDNF). Other therapeutic proteins and chemical species may also be used.

Methods of promoting and/or accelerating bone regeneration, in some embodiments, can also comprise or include additional steps. Individual steps may be carried out in any order or in any manner not inconsistent with the objectives of the present disclosure. For example, in some embodiments, methods described herein further comprise reestablishing a blood supply to the bone site and/or a biological region adjacent to the bone site. In certain cases, reestablishing a blood supply can comprise or include sealing or suturing biological tissue adjacent to the bone site. Additionally, in some cases, where blood flow has been artificially restricted at or adjacent to the bone site, such as by clamping or suction, reestablishing a blood supply can comprise or include releasing or removing the artificial restriction. Further, in some cases, a method of promoting and/or accelerating bone regeneration can comprise or include increasing one or more of osteoconduction, osteoinduction, osteogenesis, and angiogenesis within the bone site and/or a biological area adjacent to the bone site. Additionally, in some instances, methods further comprise stimulating regeneration of bone and/or soft tissue proximate the bone site.

In some embodiments, the bone site is an intramembranous ossification site. For example, recruitment of resident mesenchymal stem cells and/or MSCs provided in methods described above can transform or differentiate into osteoblasts at the bone site. An intramembranous ossification site can be any developed or developing intramembranous bone tissue in need of bone regeneration.

In other embodiments, the bone site is an endochondral ossification site. For example, recruitment and/or proliferation of resident chondrocytes and/or differentiated MSCs provided in methods described above can further promote and/or accelerate bone regeneration at the bone site. An endochondral ossification site can be any developed or developing cartilaginous bone tissue in need of bone regeneration.

Moreover, in some embodiments, methods of promoting and/or accelerating bone regeneration described herein can comprise delivering a graft or scaffold, as described above, before and/or during an early stage of osteogenic differentiation at the bone site. For example, the scaffold, in some cases, is delivered during early stages of bone regeneration, such as the proliferation stage and/or matrix maturation stage, occurring after initiation of osteogenic differentiation and prior to bone maturation.

Moreover, in some embodiments, methods of promoting and/or accelerating bone regeneration described herein can comprise maintaining the graft or scaffold in the bone site for a period of time after disposing the graft or scaffold in the bone growth site. Any period of time not inconsistent with the objectives of the present disclosure can be used. For example, in some cases, the graft or scaffold can be maintained for at least 1 month, such as for at least 3 months, at least 6 months, at least 9 months, or at least 12 months. In certain embodiments, a graft or scaffold may degrade or biodegrade within the bone site. In such embodiments, maintenance of the graft or scaffold can comprise or include maintaining the graft or scaffold until a desired portion of the graft or scaffold has degraded or biodegraded. For example, methods can comprise maintaining the graft or scaffold in the bone site until at least 50%, at least 60%, at least 70%, at least 80%, at least 90%, at least 95%, or at least 99% of the graft or scaffold has degraded or biodegraded. In certain embodiments, methods can comprise maintaining the graft or scaffold in the bone site until all or substantially all of the graft or scaffold has degraded or biodegraded. In some embodiments, biodegradation of the graft or scaffold can be measured by measuring the fluorescence intensity at the time of delivery (to) and comparing additional fluorescence intensity measurements at later times to the to measurement.

Some embodiments described herein are further illustrated in the following non-limiting examples.

EXAMPLES hMSCs Culture and Differentiation Study hMSCs with passage ≤6 were used in the present differentiation study. To assess the citrate effect on osteogenic differentiation, cells at ~80% confluence were treated with an established osteogenic (OG) medium (low glucose DMEM with $10^{-7}$ M Dexamethasome, 0.05 mM ascorbate-2-phosphate, and 0.01 M β-glycerophosphate) supplemented with citrate (pH adjusted) at different concentrations between 20 µM and 2000 µM to initiate differentiation and culture with cells for predetermined days. To determine whether citrate could induce osteogenic differentiation, hMSCs were cultured in growth medium supplemented with citrate for predetermined time periods. To evaluate whether citrate pretreatment could promote subsequent osteogenic differentiation, hMSCs were treated with 200 µM of citrate supplementation in growth medium for 4 days before the culture medium was changed to OG medium without citrate addition, and cultured with cells for predetermined time periods. To identify differentiation stage specific effects, citrate was supplemented into OG medium at different stages of differentiation (day 0-day 4; day 4-day 14; day 14-day 21). To evaluate whether soluble PSer could have an impact on the citrate effect, hMSCs were treated with OG medium supplemented with 200 µM of citrate as well as PSer at different concentrations between 40 and 1000 µM, and incubated for predetermined time periods. For osteophenotype progression assessment, cells were lysed, and alkaline phosphatase (ALP) production was quantified by using p-nitrophenyl phosphate (PNPP) as its substrate. Alizarin Red was used to stain the calcium nodules formed by the differentiating cells, and the calcium content in the nodules was quantified by Calcium Assay Kit (Sigma-Aldrich, St. Louis, Mo.) and normalized to protein amount as determined by BCA protein assay kit (Thermo Scientific™, Waltham, Mass.). Expression of osteogenic master transcription factor Runx2 was examined by real-time PCR and by using a Runx2 ELISA kit (American Research Products, Inc.™, Waltham, Mass.) according to manufacturer's instructions. Moreover, the expression of bone matrix proteins Collagen type I and osteopontin (OPN) were evaluated with real-time PCR, while OPN expression were also observed by immunofluorescent staining. Western blot was performed to evaluate the expression of ALP, OPN and SLC13a5 before or after differentiating for predetermined time periods. Detailed procedure is provided in the Supplemental Materials and Methods.

Protein Synthesis, ATP Measurements, OCR and ECAR Measurements

To assess the effects of citrate on protein synthesis, undifferentiated hMSCs seeded in 96 well plates with black walls were treated growth medium supplemented with 200 µM of citrate, Chx/Torin1, or both. Upon 24 and 96 hours incubation, protein synthesis was measured by labeling the intracellular translating proteins with clickable probes (Protein Synthesis Assay kit, Cayman Chemical, Ann Arbor, Mich.). For intracellular ATP, mitochondria respiration and glycolytic flux studies, hMSCs and differentiating hMSCs (differentiated for 14 days) were cultured in 96 well plates with black walls with/without citrate supplementation before respective measurement with Luminescent ATP Detection Assay Kit (Abcam, Cambridge, UK), Extracellular $O_2$ Consumption Assay (Abcam, Cambridge, UK), or Glycolysis Assay Kit (Abcam Cambridge, UK). To inhibit citrate uptake, 2 µM of PF06761281 (Sigma-Aldrich, St. Louis, Mo.) was used as the inhibitor for SLC13a5 to pretreat cells for 1 h before the supplemented medium with both citrate and inhibitor was added to cells.

Synthesis, Characterization and Properties of BPLP-PSer

For BPLP-PSer-0.2 synthesis, citric acid, 1,8-octanediol and O-phospho-DL-serine at molar ratios of 1:1.2:0.2 (5:6:1) were mixed in a round bottom flask. After melting at 160° C., the mixture was stirred continuously under magnetic stirring with the temperature lowered to 140° C. to produce the BPLP-PSer pre-polymer. The reaction was quenched with 1,4-dioxane to dissolve the pre-polymer, and purified by precipitating the pre-polymer solution in water followed by freeze drying. For $^{31}P$ nuclear magnetic resonance (NMR) analysis, 5 mg of polymer was dissolved in 1 mL of deuterated dimethyl sulfoxide (DMSO-d6; Sigma-Aldrich, St. Louis, Mo.) and the $^{31}P$-NMR was recorded on a Bruker Advance 600 NMR spectrometer (Bruker, Billerica, Mass.). To quantify PSer incorporation, high performance liquid chromatography (HPLC; Shimadzu, Kyoto, Japan) was applied to determine PSer content from degradation products as well as in release medium. The photoluminescent properties of polymers were studied using a Horiba FluoroMax-4 spectrofluorometer (Horiba Scientific, Edison, N.J.). The fluorescent spectra was measured in 1,4-dioxane solutions at concentrations of 2 wt. % with excitation and emission slit sizes of 1.5 nm by 1.5 nm unless otherwise specified. The photostability of polymers and commercial small molecule were determined by monitoring the decay of the emission intensity at their maximum excitation and emission wavelengths under 3 h of continuous illumination in the spectrofluorometer. Detailed procedure is provided in the Supplemental Materials and Methods below.

Cytocompatibility Evaluation and hMSCs Differentiation

To evaluate the cytocompatibility of polymers, the cytotoxicity of liquid extract from polymer films to L929 cells was evaluated with Cell Counting Kit-8 (CCK-8) assay according to international standard ISO 10993-5:2009(E). To evaluate the cytotoxicity of polymer films to 3T3 cells by direct contact, cells were seeded onto sterilized polymer films (d=6 mm) placed in 96 well plates and cultured for 24 h before the cell viability was evaluated with CCK-8 assay according to manufacturer's instructions. Proliferation of human mesenchymal stem cells (hMSCs) was evaluated by seeding cells at density of 10,000 cells/cm$^2$ to polymer films (d=6 mm) placed in 96 well plates and cultured for 1, 3 and 5 days, before cell viability was evaluated with CCK-8 assay. Immune evaluations of polymer films were performed using the THP-1 monocyte model. Briefly, $10^6$ cells/mL of THP-1 cells were incubated with polymer films (d=10 mm, 48 well plates) for 18 h before the interleukin-1 β(IL-1β) in the cell suspension was determined using ELISA kit (R&D systems, Minneapolis, Minn.). Detailed procedure is provided in the Supplemental Materials and Methods. To test the hMSCs differentiation on films, 10,000 cells/cm$^2$ of hMSCs were seeded and cultured on polymer films for predetermined time periods before cells were lysed for ALP assay and RNA was extracted for real-time PCR assays.

In Vitro Mineralization Study and Scanning Electron Microscopy (SEM) Observation To evaluate the bioactivity of polymer surfaces, polymer films and composite disks with diameters of 6 mm were incubated at 37° C. in simulated body fluid (5×mSBF) for predetermined time periods before the films were washed thoroughly and air-dried. Finally, minerals formed on films/disks were finally observed and analyzed using FESEM (Zeiss Sigma) equipped with energy dispersive X-ray spectroscopy (EDS) elemental analysis after sputter coating with iridium (Emitec Sputter-Coater). Elemental data was collected at each area of interest at 10 kV and analyzed using AZtec (Oxford Instruments, Abingdon, UK).

Preparation and Characterization of Microparticulate (MP) Scaffold

To prepare polymer/HA microparticulate scaffolds, 1.245 g of pre-polymer were first dissolved in 1,4-dioxane to prepare 30 wt. % polymer solutions, followed by mixing with 1.245 g of hydroxylapatite (HA; Sigma-Aldrich; Purum p.a. ≥90%) and 10 g of NaCl particles with diameters of 150-250 µm. The mixture was spread out on Teflon dishes until clay-like to form thin film scaffolds. After solvent evaporation, the scaffolds were cross-linked at 80° C. for 3 days and all salts were leached by soaking the scaffolds in water. Once freeze-dried, the prepared porous scaffolds were ground and sieved to collect the microparticles (MPs) with sizes between 250-500 µm. For SEM observation, the porous scaffolds were cut horizontally after immersing in liquid nitrogen, and cross-section of the scaffolds and the collected MPs were observed by FESEM (Zeiss Sigma) after sputter coating with iridium (Emitec Sputter-Coater).

hMSCs Differentiation with MP Scaffold

To evaluate hMSC differentiation on MPs, 25 mg of MPs were sterilized and transferred into transwell inserts (Sigma-Aldrich) placed in 24 well plates. Following, hMSCs at densities of 1.3×10$^5$ cells/insert were seeded and mixed with MPs. After culturing in GM/OG medium for 14 and 21 days, the generated round disk-like cell-MP constructs were washed thoroughly with PBS. One part of the constructs was lysed with RIPA buffer to generate cell lysate and subjected to further ALP assay and DNA quantification, while the other part was carefully taken out from inserts to take pictures and test their compressive mechanical properties, or to be fixed with 4% paraformaldehyde for cryo-sectioning with a thickness of 25-am, followed by hematoxylin and eosin (H&E) staining and microscope observation. To obtain the "PSU" shaped cell-MPs constructs, the in vitro 3D culture models with permeable bottoms and with the shape of "P", "S" and "U" were prepared by making the three letters with PLA filaments by 3D printing, and by casting PDMS against the letters to fabricate letter-shaped penetrating cavities. Next, permeable membranes with pore sizes of 3 μm were attached to the bottom of the cavity using nail polish, forming letter shaped wells which were prepared for cell culture by washing and sterilizing with 70% ethanol and UV exposure. Then, 80 mg of the sterilized MPs were seeded and mixed with $6.7 \times 10^5$ cells in each letter-culture model, which were cultured in GM for 24 h before changing to OG. After differentiating for 21 days, the generated cell-MPs constructs were taken out and fixed with 4% paraformaldehyde.

Rat Femoral Condyle Defect

Sprague Dawley rats weighing around 300 g were used for in vivo evaluation of our microparticles. All animal experiments were carried out in compliance with a protocol approved by Southern Medical University's Animal Care and Use Committee (Guangzhou, China). The animals were randomly divided into four groups: 1) filled with BPLP-PSer/HA microparticles (BPLP-PSer/HA); 2) filled with POC/HA microparticles (POC/HA); 3) filled with PLGA/HA microparticles (PLGA/HA); and 4) left empty as a negative control (CON). The animals were anesthetized by intraperitoneal injection of chloral hydrate at a dosage of 0.4 mL/100 g. A 1.5-2 cm medial incision on the lateral knee was created to expose the lateral femoral condyle. Bone defects with a diameter of 3.5 mm were drilled at both sides of lateral femoral condyles, which were constantly cooled with sterile saline. The implants, after being wetted with sterile saline, were next inserted into defects via press fit. After all surgical procedures, the rats were kept in cages and maintained with a regular laboratory diet. The knees were harvested after 1, 2 and 3 months of implantation for micro-CT analysis and histological analysis. Moreover, the tissue sections obtained from the BPLP-PSer/HA groups were subjected to fluorescent imaging.

Rat Critical Sized Cranial Defect

Sprague-Dawley rats (male, age 8-10 weeks, weighing ~300 g) were used for the animal experiments. The body weights were closely monitored to confirm feeding and expected growth rates. All animal experiments were carried out in compliance with a protocol approved by Southern Medical University's Animal Care and Use Committee (Guangzhou, China). Animals were randomly assigned into four groups in which the 5 mm defect was: 1) filled with BPLP-PSer/HA microparticles (BPLP-PSer/HA), 2) filled with POC/HA microparticles (POC/HA), 3) filled with PLGA/HA microparticles (PLGA/HA), or 4) left empty as a negative control (CON). Surgeries were performed with animals under anesthesia induced by the intraperitoneal injection 0.4 mL/100 g of chloral hydrate. The surgical site was shaved and cleaned with a 70% ethanol solution. A subcutaneous injection of 0.5 mL of 1% lidocaine (local anesthetic) was given at the sagittal midline of the skull. Following this injection, a sagittal incision (1.5-2 cm long) was made over the scalp from the nasal bone to the middle sagittal crest, and the periosteum was bluntly dissected. A 5 mm diameter pit defect was made with a trephine drill, which was constantly cooled with sterile saline to prevent extensive heat damage. The calvarial disk was then carefully removed to avoid tearing of the dura, and implants were next inserted into defects via press fit. The periosteum and skin were completely closed by suturing with 6-0 vicryl, and the animals were monitored according to standard post-operative animal care protocols. Animals were ultimately anesthetized and sacrificed after 1, 2, 3 months post-surgery, and the skulls were collected for micro-CT imaging, histochemistry and immunostaining analysis.

Micro CT Analysis.

Bone formation within the fixed rat defects was evaluated via isolated bone mode using the LaTheta Laboratory X-ray CT scanning system LCT-200 (Hitachi Aloka Medical Ltd., Japan) at low voltage with an integration time of 200 ms for each of the 360 rotational steps. A total of 100 slices with resolutions of 96 μm and voxel sizes of 48 μm were collected, and the reconstructed dataset was segmented by an automated thresholding algorithm. The projection images were reconstructed into three-dimensional images using VGStudio MAX (version 2.2.2). The volume of interest (VOI) was defined as a hollow cylinder of a height that could cover the entire thickness of defect, and the bone mineral density (BMD) among groups was calculated using Latheta software (Hitachi Aloka Medical Ltd., Japan).

Statistical Analysis

All quantitative data are presented as mean±s.d. with a minimum of three independent samples. Statistical analyses were performed using Statistical Package for Social Sciences (SPSS; v.18), and ordinary One-way analysis of variance (ANOVA) was performed on three or more groups with the Tukey post hoc test applied within groups, while two-tailed unpaired t-test was applied when only two groups were compared. P values <0.05 were regarded as statistically significant.

Cell Culture and Medium

Human mesenchymal stem cells (hMSCs; Lonza) were cultured in low glucose Dulbecco's Modified Eagle Medium (DMEM) with 10 vol. % fetal bovine serum (FBS) (Atlanta Biologicals; Flowery Branch, Ga.) and GlutaMAX (Gibco Laboratories, Gaithersburg, Md.). Mouse 3T3 embryo fibroblasts and L929 fibroblasts were respectively cultured in DMEM with 10 vol. % FBS and Eagle's Minimum Essential Medium (MEM) with 10 vol. % FBS. Human acute monocytic leukemia cells, THP-1, were thawed using RPMI-1640 with 20 vol. % FBS and 0.05 mM 2-Mercaptoethanol, with the culture flask placed upright for better cell recovery. After passaging cells once, the culture flask was layed down and cells were cultured in RPMI-1640 medium with 10 vol. % FBS and 0.05 mM 2-Mercaptoethanol. All the cells were cultured in a humidified atmosphere with 5% $CO_2$ at 37° C.

ALP Assay and DNA Quantification

For ALP expression analysis, cell samples were lysed using RIPA buffer, and the cell lysate was centrifuged to remove debris. Then ALP activity measurement was performed by utilizing p-nitrophenyl phosphate (PNPP) which is hydrolyzed by ALP into a yellow colored product. Briefly, the PNPP stock solution (IM) was diluted with ALP assay buffer at a ratio of 1:100, 50 μL of which was subsequently added to 50 μL of lysate sample. After 10-30 min of incubation at 37° C., the plates were measured at 405 nm on a plate reader (TECAN, Männedorf, Switzerland). The same cell lysate solutions were used to determine DNA amount via a PicoGreen dsDNA quantification kit (Invitrogen, Carlsbad, Calif.) according to the manufacturer's instructions.

Alizarin Red Staining and Calcium Quantification

For Alizarin Red staining, cell samples were fixed with 4% paraformaldehyde, and 40 mM Alizarin red solutions were used to stain calcium nodules for 30 min with gentle shaking. After thoroughly washing, the stained cells were observed on a Microscope (Nikon, Tokyo, Japan). For calcium quantification, cell samples were washed with PBS and decalcified in 0.6 N HCl for 12 h with gentle shaking. Calcium content in the supernatants was determined colorimetrically by using the Calcium assay kit (Sigma-Aldrich, St. Louis, Mo.), while protein content in cell lysate solutions (lysed with RIPA buffer) was determined using the Pierce BCA protein assay kit (Thermo Scientific™, Waltham, Mass.) according to manufacturer's instructions.

Real-Time PCR

Total RNA from whole cells was isolated with QIAGEN RNeasy kit (Hilden, Germany) and was transcribed into cDNA using High-Capacity cDNA Reverse Transcription Kits (Applied Biosystems™, Foster City, Calif.). For quantitative analysis, real-time PCR was performed using cDNA as the template, together with TaqMan Gene Expression Master Mix and the TaqMan Gene Expression Assays with both primers and probe included (Applied Biosystems™, Foster City, Calif.), and using the ABI 7900HT Fast Real-Time PCR system (Applied Biosystems™, Foster City, Calif.) according to manufacturer's instructions. Human PPIA (Cyclophilin A) was used for normalization. The primers and TaqMan probe for human Runx2, CoL1A1, SPP1 and PPIA were Hs00231692_ml, Hs00164004_ml, Hs00959010_ml, and Hs99999904_ml, respectively.

Immunofluorescent Staining

For OPN expression analysis, hMSCs differentiated for 21 days were fixed with 4% paraformaldehyde. After washing with PBS, cells were blocked using 0.1% PBST with 1% BSA/10% normal goat serum/0.3M glycerin at room temperature for 1 h. Then the rabbit anti-osteopontin primary antibody (Abcam; ab8448) 1:500 diluted with blocking buffer was added to samples and incubated overnight at 4° C. After washing with PBS 3 times, the samples were incubated with Alexa Fluor 647 labeled secondary antibody Goat-anti-rabbit IgG (Molecular Probes, Eugene, Oreg.) 1:500 diluted with PBS-1% BSA for 1 h. Subsequently, DAPI 1:1000 diluted with PBS was applied to stain the cell nucleus, and the stained cells were observed and recorded on a Fluorescence microscope (Keyence BZ-9000, Osaka, Japan).

Western Blotting

To evaluate ALP, OPN and SLC13a5 expression, hMSCs differentiated in OG for predetermined days with different concentrations of citrate were lysed using ice-cold RIPA buffer with protease inhibitor added, and centrifuged at 16,000 g to remove insoluble debris. After protein quantification by BCA assay, gel electrophoresis was carried out on AnykD™ Mini-Protean TGX stain-free Protein gels at 50 V for 10 min, followed by 250 V for 10-20 min, and was transferred to PVDF membranes with the Trans-Blot Turbo™ system. Then, membranes were blocked with TBST-5 wt % non-fat milk at room temperature for 2 hr, and incubated with primary antibodies (anti-ALP & anti-OPN primary antibody: Abcam, Cambridge, UK; anit-SLC13a5 antibody: CUSABIO, Tex., USA) overnight at 4° C. After washing with TBST with five times for 5 min, the membranes were incubated in the HRP conjugated secondary antibody solution diluted in TBST-5 wt % non-fat milk for 1 hr at room temperature, followed by rinsing and incubating with Clarity™ western ECL substrate mixture for 5 min, which was finally imaged by the ChemiDoc MP imager.

HPLC Determination of PSer

High performance liquid chromatography (HPLC; Shimadzu, Kyoto, Japan) was performed to confirm the presence of PSer in polymer degradation products and to quantify the PSer released from polymer films. To prepare degradation products, 0.5 g polymer films were fully degraded in 5 mL 0.2 N NaOH solution, and 2N HCl was added to adjust the pH to be 7.2-7.4. To determine the PSer concentration in the releasing media, films at the diameter of 16 mm were put in 24 well plates and 1 mL of PBS was added to each well. After 3, 7 and 14 days, the release media was collected for analysis.

For HPLC determination, 220 μL of each prepared samples were mixed with 100 μL of 1.5M $NaHCO_3$ (pH 9.0) and 200 μL of 2 mg/mL of dabsyl chloride in acetone followed by vortexing. After heating to 70° C. for 10 min, the mix was subsequently dried under vacuum, followed by resuspending with 400 μL of 70% ethanol and centrifuging for 2 min at 14,000 g. Finally, the supernatant was transferred to a new tube and filtered through a 0.2 μm filter. HPLC analysis was performed on a Shimadzu HPLC system equipped with a UV-visible PDA detector and a C18 column at room temperature. The detection of PSer was set at 460 nm, and a calibration curve of PSer was obtained under the same conditions.

Preparation of Polymer Films and Polymer/HA Composites

To prepare polymer films, the BPLP-PSer pre-polymer was dissolved in 1,4-dioxane to obtain a 30 wt. % solution and then was casted into a Teflon mold followed by solvent evaporation and thermal cross-linking at 80° C. for 3 days and 100° C. for another 3 days unless otherwise specified. To prepare BPLP-PSer/HA composites, 30 wt. % pre-polymer solution was mixed with 50 wt. % HA, and stirred in teflon dishes to prepare homogenous mixture. Following solvent evaporation, the composite mixture was rolled up and pressed into thin sheet using pasta roller machine, which was subsequently cut into round disks, and lastly cross-linked at 80° C. for 3 days.

Degradation Studies

For accelerated degradation studies, polymer films were cut into round disks weighing ~50 mg (d=10 mm; Thickness-0.5 mm) and placed in tubes containing 10 mL of 0.05 M NaOH solutions. All samples were incubated at 37° C. for predetermined times. At each time point, the samples were taken out, washed thoroughly with deionized water and subsequently lyophilized. Film degradation was measured by mass remaining according to equation 1:

$$W_1/W_0 \times 100\% \quad (1)$$

where $W_0$ refers to the original scaffold weight and $W_1$ represents the remaining film weight. The in vitro degradation of POC-PSer films was also monitored by fluorescent analysis. The remaining fluorescent signal in lyophilized films was measured on an in vivo fluorescent imaging system (Maestro™ EX, Woburn, Mass.) and the degradation was evaluated using equation 2:

$$F_1/F_0 \times 100\% \quad (2)$$

where $F_0$ refers to the fluorescence signal of the original film and $F_1$ represents that of the degraded film. In conjunction, fluorescent molecules released into degradation media was quantified by transferring 200 uL of the degradation media to 96 black well plates and by measuring on a plate reader (TECAN; Männedorf, Switzerland) at 370 nm excitation and 440 nm emission. The degradation pattern was plotted as cumulative release profile over the time using equation 3:

$$F_2/F_{total} \times 100\% \quad (3)$$

where $F_{total}$ refers to the total fluorescence signal that released from polymer from and $F_2$ represents the cumulative released fluorescence signal at specific time point. All three curves were fit with Allometric2.

Cytocompatibility Evaluation and hMSC Differentiation

Cytotoxicity Evaluation of Liquid Extraction of Polymer Films: To prepare liquid extracts of polymer films, both POC and BPLP-PSer films (thickness<0.5 mm) were cut into round disks with diameters of 16 mm and placed into 12 well plates once sterilized. Next, 670 μL of complete culture medium was added and incubated with polymer films for 24 h at 37° C. with agitation. Next, the liquid extracts of different polymers were collected and added to L929 cells at sub-confluence in 96 well plates and incubated for 24 h before cell viability was measured with a CCK-8 assay (Dojindo Molecular Technologies Inc., Rockville, Md.) according to international standard ISO 10993-5:2009(E).

Cytotoxicity Evaluation by Direct Contact: To evaluate the cytotoxicity of polymer films to 3T3 cells by direct contact, cells were seeded onto sterilized polymer films (d=6 mm) placed in 96 well plates and cultured for 24 h before the cell viability was evaluated with CCK-8 assay according to manufacturer's instructions.

Cytotoxicity Evaluation of Degradation Products: To prepare degradation products, 0.5 g polymer films were fully degraded in 5 mL 0.2 N NaOH solution, and 2N HCl was added to adjust the pH to be 7.2-7.4. Once centrifuged, the supernatant was filtered to another tube. Dilutions of degradation products were prepared using culture medium and 20 μL of each dilution were added to cells cultured in 96 well plates with 200 μL medium. After culturing for 24 h, CCK-8 evaluation (Dojindo, Rockville, Md.) was performed according to manufacturer's instructions.

Cell Proliferation Assay: To test cell proliferation on polymer films, BPLP films with different feeding ratio of PSer (d=6 mm) were sterilized and placed in 96 well plates before hMSC cells were seeded at densities of 10,000 cells/cm$^2$ to each well and incubated on the films. After 1, 3 and 5 days, cell viability was evaluated with CCK-8 assay (Dojindo, Rockville, Md.).

Immune Evaluation of Polymer Cytocompatibility: Immune evaluation of polymer films with THP-1 monocyte model cells was performed. Briefly, 700 μL of THP-1 monocytes at densities of 10$^6$ cells/mL were incubated with polymer film disks (PLA and BPLP-PSer) with the diameter of 10 mm in 48 well plates. As positive control, 50 ng of Lipopolysaccharides (LPS) from *Escherichia coli* 01 11:B4 (Sigma-Aldrich, St. Louis, Mo.) was added to THP-1 cell suspensions in wells without films to positively activate THP-1 to produce inflammatory factors. After 18 hours, the cell suspension of each sample was collected and centrifuged at 1500 rpm for 5 min. The supernatant was collected to determine the IL-1β concentrations using ELISA kit (R&D systems, Minneapolis, Minn.) while the pelleted cells were resuspended by CCK-8 working solutions to evaluate their cell viability.

Mechanical Testing

Compression testing of cylindrical composites: To test the compressive strength of polymer/HA composites, cylindrical samples were first prepared by mixing pre-polymers with various amounts of HA particles to prepare composites of 50 wt. % and 60 wt. % HA. Once the polymer-HA mixtures became clay-like, they were then inserted into PTFE tubing molds followed by post-polymerizing at 80° C. for 3 days and then 100° C. for 3 days. Next, compression tests were performed on the cylindrical shaped specimens using an Instron 5966 machine equipped with a 10 kN load (Instron, Norwood, Mass.) at a rate of 1.3 mm/min to failure. The initial modulus was calculated by measuring the gradient at 10% of compression of the stress-strain curve.

Compression testing of hMSC-MPs constructs: To test the compressive strengths of cell-MPs, the constructs were differentiated for predetermined time in transwell, then were taken out of transwells carefully. Compression tests were then performed on the constructs on an Instron 5966 machine equipped with a 1 kN load (Instron, Norwood, Mass.) at a rate of 1.3 mm/min, with the test reaching completion when 50% of the original specimen height was reached. The initial modulus was calculated by measuring the gradient at 10% of compression of the stress-strain curve.

ALP Treatment of Polymer Films and Determination of Inorganic Phosphate

To determine whether ALP could cleave the phosphate group from polymer films, BPLP-PSer and POC films were cut into small disks (d=10 mm; Thickness-0.5 mm) and placed in 48 well plates (n=8). Next, 250 μL/well of ALP solution in diethanolamine buffer with 5 U/mL of enzyme was added to each well and incubated from 30 min to 1 h before the samples were transferred to 1.5 mL tubes. Finally, the inorganic phosphate amount in each sample was determined by the PiPer™ Phosphate Assay Kit (P22061, Molecular Probes, Eugene, Oreg.) according to the manufacturer's instruction.

hMSC Adhesion and Proliferation Study on MP Scaffold

To observe adhesion of hMSCs, 20 mg of BPLP-PSer/HA MPs were sterilized and transferred to a 5 mL centrifuge tube. Then, 2 mL of cell suspension solutions with 5×10$^5$ cells was added to the MPs in the tube followed by continuously mixing the two on a vertical sample mixer (ThermoFisher Scientific). Following every 1 h of shaking, the shaker was paused and the cap of the tube was opened to balance the culture medium. After 6 h of shaking, the cell suspension was removed, and the cells adhered onto MPs were washed twice with PBS, followed by fixed in 2.5% glutaraldehyde. After serial dehydration, critical-point drying and coating, the adherent cells on MPs were observed with SEM. For hMSC proliferation studies, 5-6 mg/well of MPs were sterilized and transferred into 96 well plates. Next, hMSCs at densities of 1.6×10$^4$ cells/cm$^2$ were seeded to each well. After 1, 3 and 7 days of culture, CCK-8 was performed to determine the cell viability according to the manufacturer's instruction.

Histological and Histomorphometric Analysis

Histological Analysis: The defect and surrounding tissues were fixed in 4% paraformaldehyde for 48 h, decalcified with 0.5 M ethylenediaminetetraacetic acid (EDTA) at pH 7.4 at 4° C. for 4-7 weeks, and embedded in paraffin. Tissues were sectioned with a 4-μm thickness, deparaffinated with xylene, gradually hydrated, and stained with H&E for light microscopic analysis. Images were captured at 200× magnification using an Olympus Bx51 microscope (Olympus, Japan) and a digital camera (ProgRes C14, Jenoptik, Germany).

Immunohistochemical Analysis: To detect osteocalcin (OCN) expression, paraffin-embedded sections were deparaffinated and dehydrated through a graded series of alcohol. Endogenous peroxidase activity was blocked with 3% hydrogen peroxide. Then, the sections were blocked with 5% normal goat serum for 1 h and incubated with the primary anti-OCN antibody (Abcam, Cambridge, Mass.; 1:50 dilution) at 4° C. overnight. The sections were washed with PBS three times and incubated with secondary HRP-Goat anti-mouse IgG (Proteintech Group, US) for 1 h at 37° C. Colorization was subsequently developed in DAB solution and counterstained by HE. Two individual pathologists assessed IHC staining in a blinded and randomized fashion.

Fluorescent Imaging of Tissue Sections

The paraffin embedded tissues were sectioned with 4-mm thickness, and the images of remnant scaffolds in those tissue sections were obtained using a BZ-9000 fluorescent microscope with a DAPI blue cube (EX 360/40) under the same exposure time. Then, the area of remaining scaffold and the integrated density reflecting the total fluorescence were analyzed using Image J.

Citrate is an Osteo-Promotive Factor that Enhances Osteo-Phenotype Progression

Growth medium (GM) was supplemented with exogenous citrate at different dosages (0 to 2000 μM citrate, pH 7.4), which showed little increase in hMSCs proliferation and an absence of calcium deposition by Alizarin Red staining (FIGS. 7A&7B). In contrast, citrate supplementation in osteogenic medium (OG) revealed a dose-dependent elevation of osteogenic markers (FIG. 7B-7E), indicating an osteo-promotive role of citrate only after osteo-differentiation is initiated. Among the concentrations studied, 200 μM was identified as a preferred dosage for exogenous citrate supplementation based on alkaline phosphatase (ALP) and osteopontin (OPN) expression (FIG. 7C-7E). The osteo-promotive effect of citrate was confirmed by real-time PCR (FIG. 2A), which showed remarkably elevated expression of Runt-related transcription factor2 (Runx2), the earliest master determinant of osteogenesis, as well as the genes encoding bone matrix proteins, such as Col1a1 (encoding Collagen Type 1 Alpha 1) and SPP1 (encoding osteopontin) in the 200 μM citrate treatment group compared to the OG control after 7 and 14 days. Consistently, ELISA tests (FIG. 2B) showed favorable accumulation of Runx2 protein by citrate treatment as early as day 4.

Osteogenic differentiation is a three-stage process of proliferation, matrix maturation, and mineralization (FIG. 2C). To investigate the differentiation-stage dependence of the citrate effect, citrate (200 μM) supplementation was restricted to one of three time periods (days 0-4, days 4-14, and days 14-21) corresponding to each stage of differentiation, plus a pre-treatment period prior to osteo-induction (Group IV). Notably, early citrate supplementation only at the proliferation stage (Group I) already significantly elevated ALP production at day 7 (FIG. 7F), well sustaining the osteogenic effects of this early treatment through day 14 (FIG. 2D). In contrast, late citrate supplementation during the mineralization stage (Group III) exhibited diminished cumulative osteo-promotive potential compared to the other groups, measured by total calcium/protein ratio after 21 days (FIG. 2D), highlighting the important role of citrate treatment at early stages of osteogenic differentiation. Surprisingly, even citrate pre-treatment in growth medium for 4 days prior to osteogenic induction greatly improved the downstream osteo-phenotype progression, shown by increased ALP production and higher calcium/protein ratio (FIG. 2E). These exciting results above indicated that exogenous citrate was an osteo-promotive factor with a dosage-dependence centered around 200 μM and timing-dependence favoring supplementation at early stages.

Citrate Enhances Osteo-Phenotype Progression Through SLC13a5

Protein synthesis and altered metabolic activity precede and crosstalk with Runx2 expression in cells of osteoblast lineage for orchestrated osteo-phenotype progression. Thus, 24 h and 96 h of citrate pretreatment, protein synthesis in hMSCs increased significantly compared with their respective control groups without citrate in GM (FIG. 3A), while protein synthesis inhibitor Cycloheximide (Chx) as negative control, and Torin1 as an mTOR inhibitor, abolished this activity, revealing the mTOR-dependence of citrate-mediated protein synthesis. Together with the fact that citrate serves as a key metabolite for regulating cell energy metabolism we therefore speculated a "metabonegenic" model in which exogenous citrate mediates intracellular metabolic events in preparation for osteogenic differentiation To set the groundwork for this model, we next demonstrated that uptake of extracellular citrate is linked to downstream osteogenic processes by identifying and validating the transport mechanism involved. First, we performed a citrate assay (FIG. 8A) showing a marked increase in intracellular citrate of hMSCs upon 24 h incubation with citrate supplemented medium, affirming that exogenous citrate is indeed uptaken by cells since little endogenous citrate is produced by hMSCs which rely mostly on glycolysis. Using western blot, we next studied the expression of the citrate plasma membrane transporter, SLC13a5, before and after osteogenesis of hMSCs. We discovered that SLC13a5 expression was greatest in undifferentiated and early-stage differentiating hMSCs, gradually decreasing after 4 days of differentiation (FIG. 3B). Importantly, the addition of PF06761281, an inhibitor of SLC13a5, negated the citrate-induced elevation of ALP production (FIG. 3C). It is believed that exogenous citrate enters hMSCs through SLC13a5, affecting downstream osteo-phenotype progression.

Citrate Elevates Intracellular ATP by Metabolic Regulation

In response to osteo-stimulation, hMSCs undergo a metabolic switch from glycolysis to oxidative respiration to generate more ATP, since production of abundant matrix proteins during bone formation is highly energy demanding. The role of soluble citrate was investigated in hMSC energy metabolism, specifically whether citrate as a metabolic regulator affects cell energy status by regulating primary energy-generating metabolic flux. At 24 h of citrate treatment, hMSCs exhibited elevated intracellular ATP levels (FIG. 3D) and increased oxygen consumption rate (OCR) (FIG. 3E) as key indicators of mitochondrial respiration, also accompanied by a decrease in glycolytic flux indicating inhibition of glycolysis (FIG. 3F), along with reduced production of lactate (FIG. 3G) as the end product of glycolysis. It is believed that exogenous citrate facilitates the metabolic shift in hMSCs from glycolysis to oxidative respiration to induce higher intracellular ATP synthesis. Importantly, the citrate effect on metabolic flux to elevate intracellular ATP levels could be abolished by blocking the SLC13a5 with inhibitor PF06761281 (FIG. 3D-3G). It is believed that the regulatory role of exogenous citrate on cell energy metabolism is also mediated by SLC13a5. Moreover, citrate treatment of hMSCs differentiated for 14 days elicited significant effects on intracellular ATP only after 4 days of treatment (FIGS. 8B&2C), while just 1 day of treatment markedly increased hMSC mitochondrial respiration (FIG. 8D), which was likewise abolished with inhibitor PF06761281. However, the 1 day citrate treatment had no significant effect on glycolytic flux (FIG. 8E). Taken together with the findings that citrate treatment promoted mTOR-dependent protein synthesis and favored Runx2 accumulation, it is believed that there is a previously unexplored citrate metabonegenic regulation through which exogenous citrate enters hMSCs through SLC13a5 to regulate cell energy metabolism, elevating cellular energy levels, which in turn facilitates osteo-phenotype progression (FIG. 1).

Phosphoserine Prolongs Citrate Osteopromotive Effect Via Concerted Citrate/PSer Metabonegenic Regulation Phosphoserine (PSer) is a functional moiety that is abundant in non-collagenous proteins (NCPs) of natural bone. To examine the effects of PSer on the citrate-elevated cell energy status, undifferentiated hMSCs were treated with citrate, PSer, or both. The addition of PSer exerted no significant effect on the respective intracellular ATP levels of hMSCs with or without citrate treatment (FIG. 3H), indicating that PSer had no direct influence on metabonegenic processes, likely due to the low levels of phosphatases present in undifferentiated cells that render exogenous PSer biologically inactive. There was a marked increase of intracellular ATP in differentiating hMSCs from the combination of citrate and PSer, whereas individual treatments showed no difference from the OG medium control (FIG. 3I). Interestingly, the osteo-promotive effects of the dual treatment were evident particularly at late stages of osteogenesis, sustaining high levels of ALP (FIGS. 3J & 8F) and OPN production (FIG. 3K) well into day 21, whereas ALP level dropped off in the citrate-only and control treatment groups. Even a low dosage of 40 µM PSer substantially enhanced the citrate-promoted osteo-phenotype progression, with higher PSer dosages resulting in further elevation of ALP production (FIG. 8G). It is believed that citrate-induced elevation of ALP levels in differentiating cells catalyzes the dephosphorylation of PSer, thereby liberating the bioactive inorganic phosphate from PSer, while exogenous PSer in turn favorably prolongs the citrate metabonegenic effect, facilitating intracellular ATP synthesis to fuel osteo-phenotype progression (FIG. 1).

BPLP-PSer is a New Biodegradable Photoluminescent, Phosphoserine- and Citrate-Based Polymer Polymers were designed in which PSer incorporation in citrate-based polymers may facilitate mineral deposition and regulate bone cell activities. To prepare biodegradable photoluminescent polymers incorporating PSer (BPLP-PSer), O-Phospho-DL-serine was reacted with citric acid and 1,8-octanediol via a one-pot condensation reaction to prepare the pre-polymer, which could be further post-polymerized to generate an elastomeric crosslinked polymer network (FIG. 9A). The PSer incorporation was next confirmed by 31P-nuclear magnetic resonance (NMR, FIG. 9B). High performance liquid chromatography (HPLC) analysis further verified the presence of PSer in both the accelerated degradation product and the release medium of BPLP-PSer films (FIGS. 9C&9D), while phosphate assay of crosslinked films demonstrated the release of inorganic phosphate from the incorporated PSer in BPLP-PSer after ALP treatment (FIG. 9E).

Figure 4B:
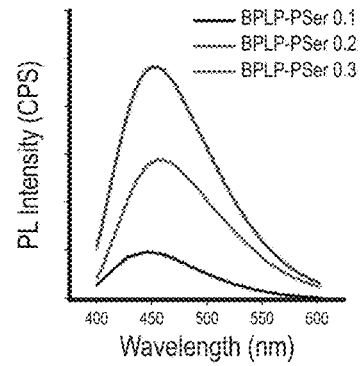
Figure 4C:
Figure 4D:
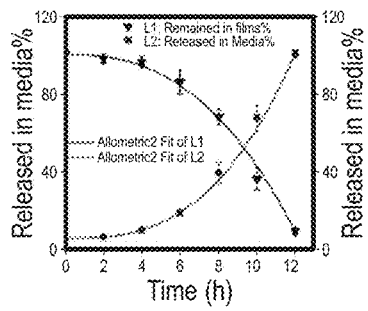
Figure 4E:
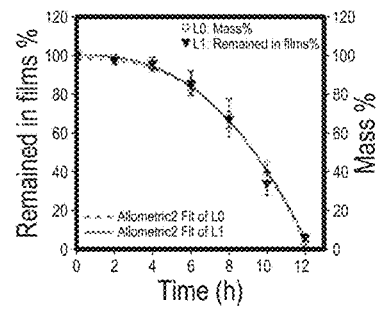

BPLP-PSer emitted strong fluorescence with excellent photostability (FIGS. 9F&9G), attributed to a conjugated heterocyclic structure within the polymer backbone generated by a key condensation step between citrate and PSer. The wavelength of fluorescence emission was tunable by changing the excitation wavelength, consistent with the band-shifting behavior described previously, while the fluorescence intensity was tunable by changing the molar ratio of PSer (FIGS. 4A&4B). To demonstrate fluorescence tracking, the gradual decay was measured in total fluorescence signal of BPLP-PSer films using the Maestro™ EX in-vivo imaging system (FIG. 4C), which was accompanied by a corresponding increase in accumulated fluorescent signals of the degradation solution over the same (accelerated) degradation time (FIG. 4D). Moreover, the mass remaining profile by conventional gravimetric analysis coincided with the remaining total fluorescence profile (FIG. 4E), indicating that the degradation of BPLP-PSer could be reliably tracked by either the remaining fluorescence in polymer films or the fluorescent moiety released from the polymer films over time.

Incorporated PSer Facilitated Mineral Deposition and Improved Cytocompatibility

Figure 10:
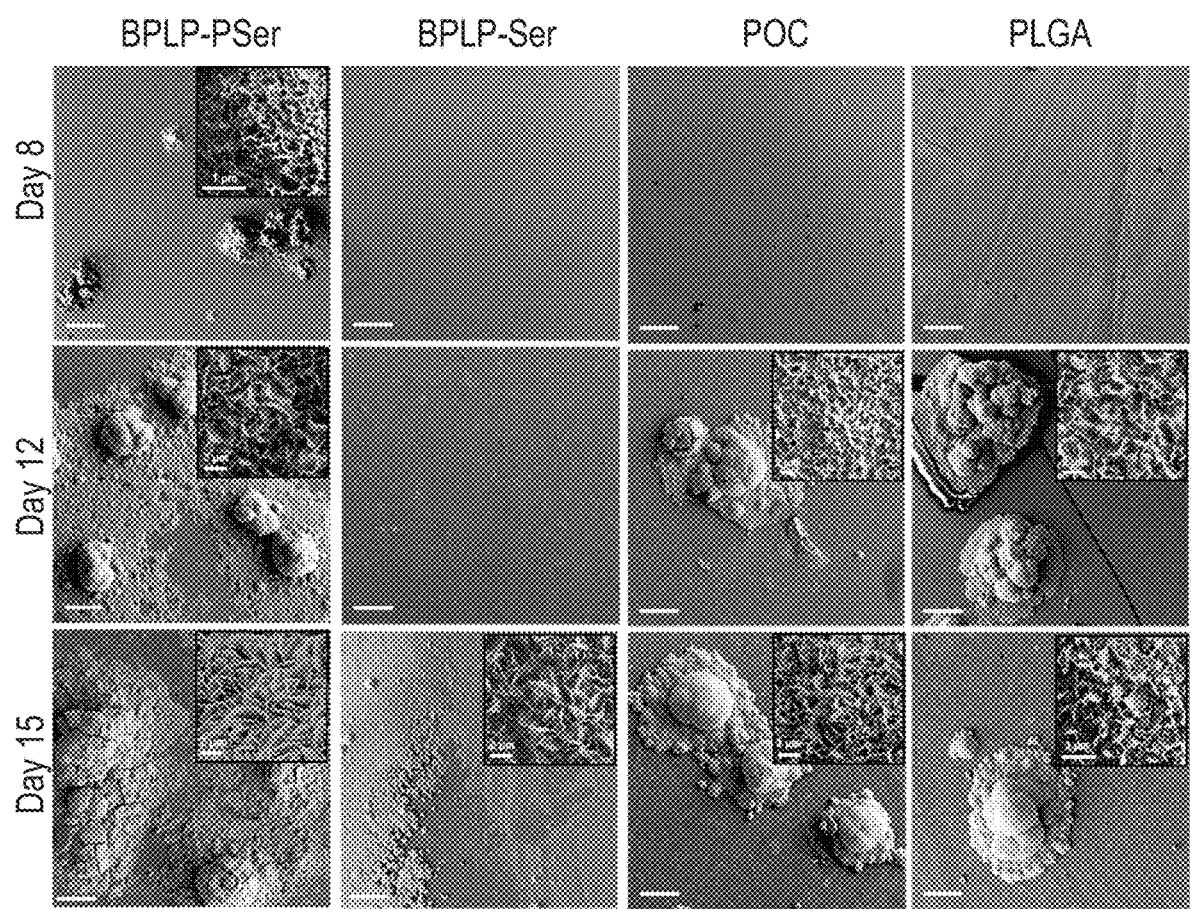
FIG. 10 are images showing in vitro mineralization tests on polymer films (Scale bar: 200 µm). BPLP-PSer films induced accelerated mineral deposition compared to poly (octamethylene citrate) (POC) and BPLP-Ser as citrate-based materials control, as well as PLGA 75/25 as a general control. Inserted high magnification images presenting the morphology of the formed minerals further showed that BPLP-PSer films also induced earlier formation of petal-like minerals than other control materials, confirming the improved surface bioactivity brought by PSer incorporation.

To evaluate surface bioactivity for mineralization, an in vitro mineralization assay was conducted by immersing crosslinked BPLP-PSer films in simulated body fluid (SBF), with PLGA 75/25 as a general control, along with poly (octamethylene citrate) (POC) and BPLP-Ser (incorporating L-Serine) as citrate-based material controls. BPLP-PSer films displayed accelerated mineral deposition compared to all controls (FIG. 10). It is believed that PSer was a key monomer for facilitating mineralization in citrate-based polymer formulations, which was supported by a follow-up mineralization assay using polymer/50% hydroxylapatite (HA) (FIG. 11A). In mechanical evaluations, the BPLP-PSer/50% HA composites possessed an impressive compressive strength of ~200 MPa (FIG. 11B) falling into the range of human cortical bone (100-230 MPa). Such materials are believed to have applicability in orthopedic applications. BPLP-PSer also improved the maximum HA binding capability (up to 60%) compared to BPLP-Ser (FIG. 11B), notable as BPLP-PSer/60% HA improved the modulus two-fold compared to its 50% HA composition.

Figure 4F:
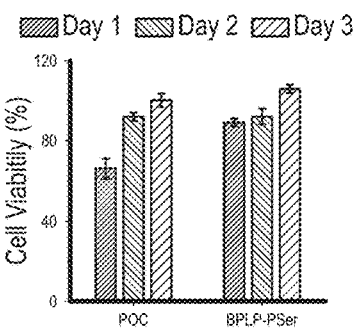
Figure 4G:
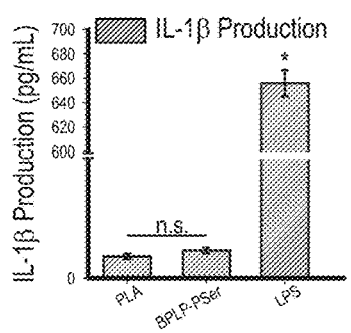
Figure 4H:
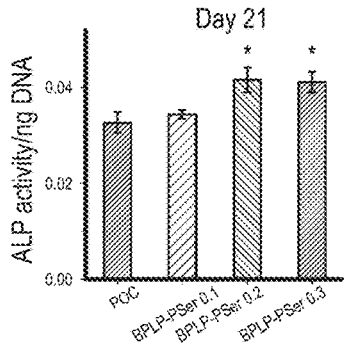
Figure 4I:
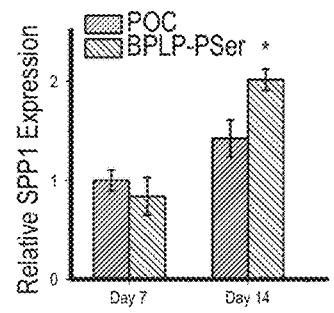
Figure 12A:
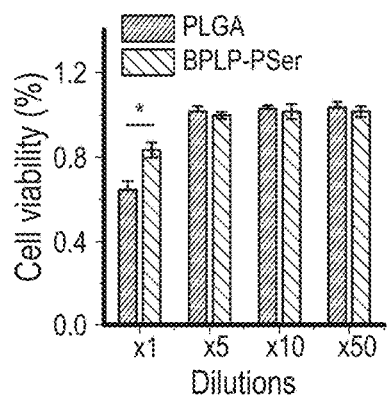
FIGS. 12A-12E are plots showing results of cytocompatibility evaluations of BPLP-PSer. (A) Cytotoxicity of degradation products of polymer films to MG63 cells, showing reduced MG63 cytotoxicity compared to control PLGA75/25 samples. (B) Viability of MG63 cells cultured on polymer film with direct contact by CCK-8, showing no significant reduction of cell viability from culturing osteoblast-like MG63 cells directly on films (In A&B, n=6 biological replicates per group). (C) Cell viability of THP-1 cells incubated with polymer films tested by CCK-8, showing no negative effect on cell viability by incubating THP-1 with polymer films. (D) Cell proliferation on polymer films with various molar ratio of PSer incorporated determined by CCK-8. (E) ALP production of differentiating hMSCs cultured on polymer films in OG medium at day 14 (In C-E, n=3-4 biological replicates per group; All plots represent mean±s.d.; * indicating P<0.05).
Figure 12B:
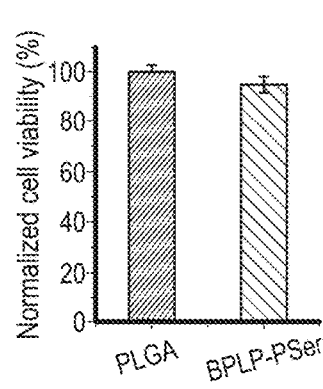
Figure 12C:
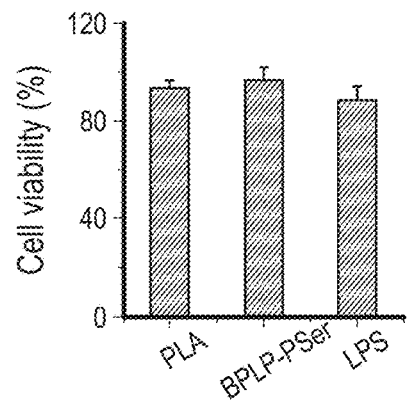
Figure 12D:
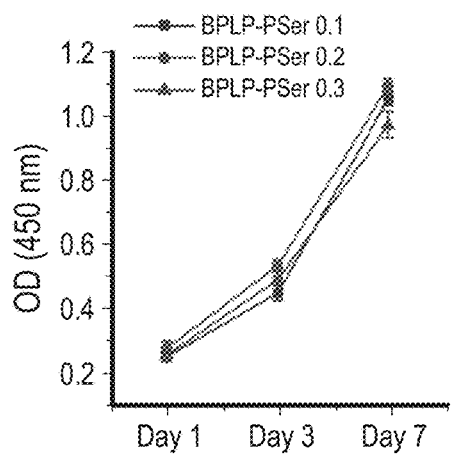
Figure 12E:
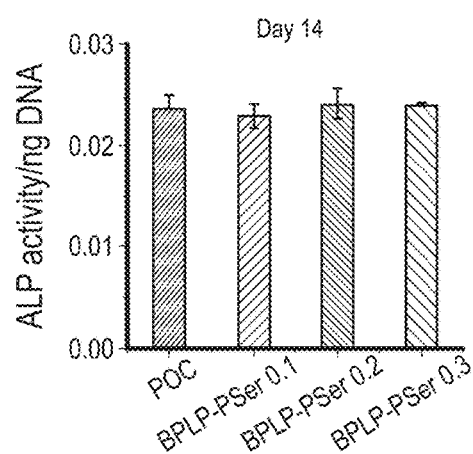

The cytocompatibility of BPLP-PSer was systematically evaluated on leachable extracts (FIG. 4F), degradation products (FIG. 12A) and by direct contact on films (FIG. 12B), demonstrating cell viabilities comparable with those of PLGA control. ELISA studies further supported that the release of inflammatory factor IL-1β from THP-1 monocytes induced by BPLP-PSer films was equivalent to the PLA control (FIGS. 4G&12C). Furthermore, BPLP-PSer film compositions varying PSer content (0.1 to 0.3 molar ratios to citrate) were all shown to support hMSC proliferation (FIG. 12D) and osteogenic differentiation, with BPLP-PSer-0.2 and BPLP-PSer-0.3 compositions significantly elevating ALP production by day 21 (FIGS. 4H&12E), and BPLP-PSer 0.2 exhibiting significantly higher OPN gene expression by day 14 (FIG. 4I) compared to its POC counterpart.

Figure 5A:
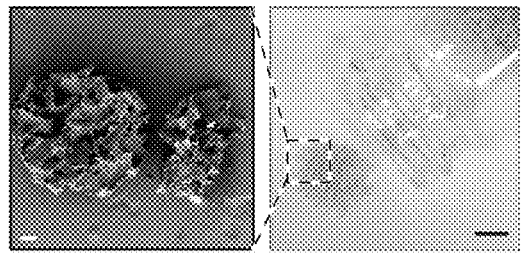
FIGS. 5A-5H are plots and images related to BPLP-PSer/HA microparticulate scaffolds promoted hMSC differentiation. (A) Bright field (right; scale bar: 5 mm) and scanning electron microscope (SEM; left; scale bar: 100 µm) images of BPLP-PSer/HA Microparticule scaffolds (MPs). (B) Intracellular ATP levels (normalized to DNA) of hMSCs cultured on different MPs in GM for 4 days (n≥8 biological replicates per group). ALP production of hMSCs cultured on Mps in transwell 3D models (C) in GM without osteogenic inducers, and (D) differentiated in OG medium for 21 days (n=3-5 biological replicates per group). (E) Compressive strength of round disk shaped cell-MP constructs after differentiating cells for 1, 2 and 3 weeks in OG (n=3 cell-MPs constructs per time point; All plots represent mean±s.d.; * indicating P<0.05). (F) Bright field photos and fluorescent images of hMSC-MP constructs obtained from 21 days of cultures in round transwells (left) or from cultures in PDMS wells with permeable bottom and the shape of "P" "S" and "U" (right; scale bar, 5 mm), casted from 3D printed letter molds. (G) SEM images of the thick cell layer covering and bridging MPs (top) and extensive interwoven extracellular matrix (ECM) network (bottom; left) produced by hMSCs differentiated for 21 days in OG to enable mineral formation (bottom; right). (H) Fluorescent images (blue, green and red channels) and H&E staining (bottom; right) of the cell-MP construct sections obtained by cryo-sectioning (scale bar: 200 µm).
Figure 5B:
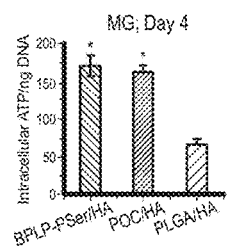

BPLP-PSer/HA Microparticles with "Ridge and Cliff" Surface Features Supported hMSCs Adhesion and Proliferation To translate the concerted, osteopromotive actions of citrate and PSer towards a new biomimetic material for orthopedic applications, a composite microparticulate (MPs) scaffold was developed from porous BPLP-PSer/50% HA scaffold (150-250 µm pore size by salt leaching, FIG. 13A), ground and sieved into 250-500 µm sized MPs (FIG. 5A). The procedure was repeated for the POC/50% HA control, although the PLGA control could only composite up to 30% of HA for MPs preparation. The BPLP-PSer/HA MPs demonstrated excellent handling ability, easily mixing with saline solution (FIGS. 13B&13C), sodium hyaluronate carrier (FIG. 13D) or blood from patients to facilitate surgical applications. The resulting BPLP-PSer/HA MPs greatly supported hMSCs adhesion as examined by SEM, revealing that cells were abundantly adhered onto the "cliff", "ridge" as well as "groove" (FIGS. 13E&13F) structures of MPs after 6 h of continuous mixing of MPs and suspended hMSCs. In addition, BPLP-PSer/HA MPs supported immediate and earlier proliferation of hMSCs compared to POC/HA MPs (FIG. 13G). More importantly, hMSCs cultured on POC/HA and BPLP-PSer/HA for 4 days showed a substantial increase in intracellular ATP, almost twice that of PLGA/HA MPs (FIG. 5B), likely due to citrate metabonegenic regulation innate in both citrate-based MPs, while PSer incorporation did not provide additional benefits to undifferentiated hMSCs as expected.

BPLP-PSer/HA MPs Promoted hMSC Differentiation

Figure 5C:
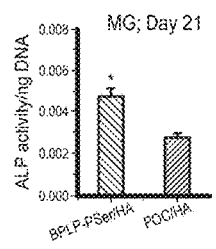
Figure 5G:
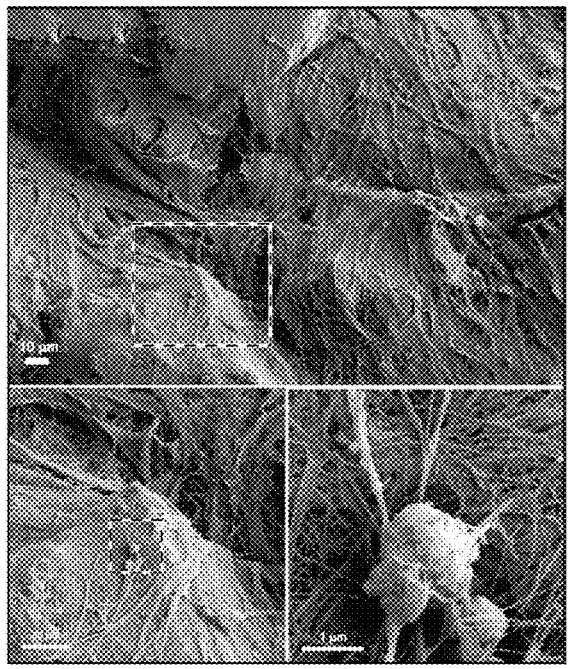
Figure 5D:
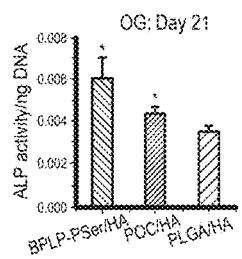
Figure 5E:
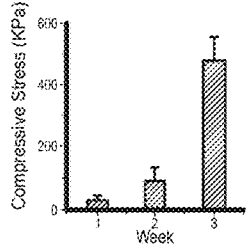
Figure 5F:
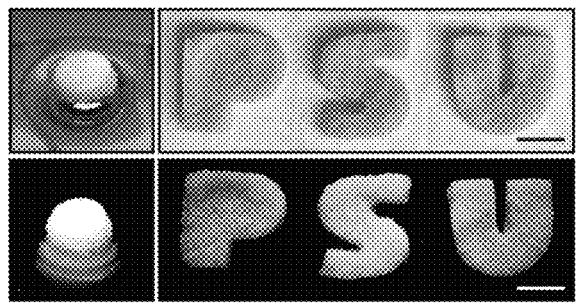
Figure 5H:
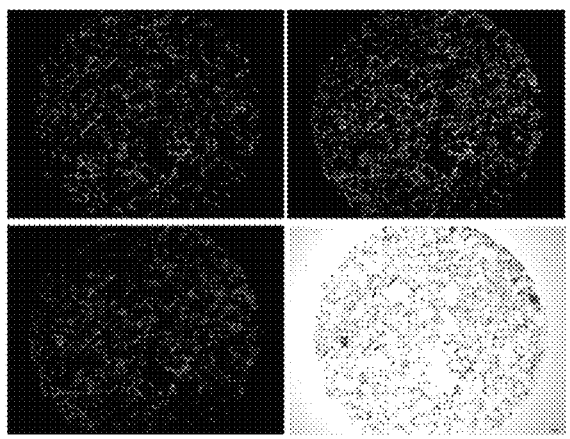

To determine whether citrate and PSer presenting MPs could exert concerted action on osteogenic progression by 3D transwells (Pore size: 3 µm) were used as an in-vitro cavity defect model, into which different MP formulations were inserted and cultured with hMSCs. Notably, even in the absence of osteogenic inducers, hMSCs in growth medium showed significantly higher ALP expression in the BPLP-PSer/HA group compared to that of POC/HA (FIGS. 5C&13H). In osteogenic medium, hMSCs displayed a substantial elevation of ALP expression in the BPLP-PSer/HA MP group by day 21 (FIG. 5D), outperforming those in the PLGA control and even in the citrate-only POC control, supporting the notion that citrate and PSer may collaborate to elicit sustained bone forming activities. Of note, as osteo-differentiation progressed, the MPs were integrated by cells to form fluorescent bone-like tissue constructs (FIGS. 5F&15A) that remained intact upon compression and recovered upon unloading, along with increased compressive strength and modulus (FIGS. 5E&14B). By designing PDMS culture wells in the shape of the letters P, S and U, a "PSU" shaped fluorescent constructs were generated (FIG. 5F), demonstrating the ability of MPs to fill and bridge irregular defects. In fact, SEM revealed a thick layer of cells covering MP surfaces and bridging together adjacent MPs (FIG. 14C), along with extensive ECM production forming intertwined networks that was accompanied by significant calcium phosphate mineral deposition (FIGS. 5G&14D). Further, cryo-sectioning and H&E staining of the rounded bone-like disks revealed a homogeneous distribution of cells throughout the constructs (FIG. 5H) such that cells and MP interfaces were closely integrated (FIG. 14E). Meanwhile, fluorescent imaging of the sections showed strong fluorescence from MPs at different excitation wavelengths, which also confirmed a highly porous framework generated by packed MPs in transwell (FIG. 5H), beneficial for cell interaction and tissue penetration.

BPLP-PSer/HA MPs Efficacy in the Femoral Condyle Defect Model

Figure 15A:
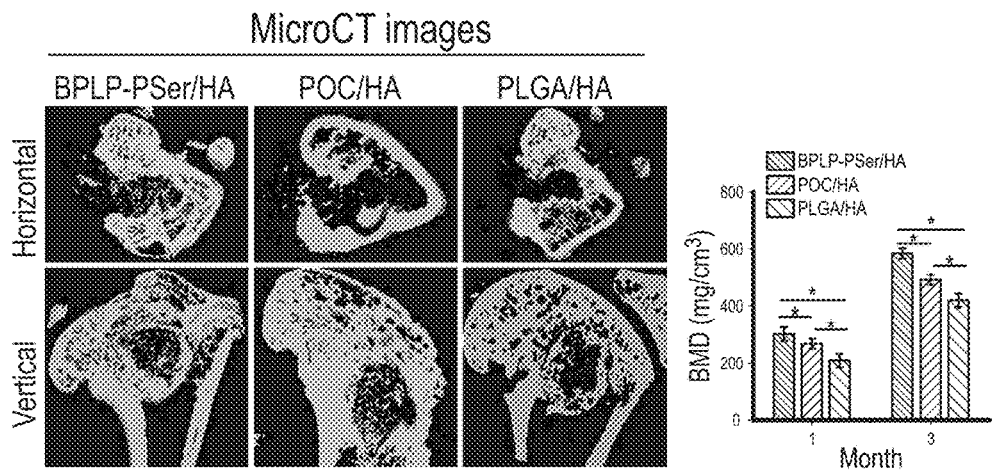
FIGS. 15A-15C are images and a plot showing in vivo results in femoral condyle defects. (A) MicroCT images of femoral condyle defects with BPLP-PSer/HA, POC/HA, and PLGA/HA MP scaffolds at 1 month after implantation with BMD analysis (Right; n=6 defects per group). (B) H&E staining of femoral condyle defects with no MPs implanted at 1 and 3 month after implantation (Scale bar: 50 µm). (C) Fluorescent images of remaining BPLP-PSer/HA scaffold in tissue sections at 1, 2 and 3 month after implantation (Scale bar: 400 µm).

Next, to evaluate the in vivo efficacy for promoting bone regeneration, BPLP-PSer/HA MPs were implanted into a rat femoral condyle defect, a standardized unicortical defect widely used for screening particulate implants, while POC/HA MPs, PLGA/HA MPs, and no implant groups served as comparisons. Micro-computed tomography (micro-CT) analyses at 1 and 3 months showed more new bone formation in the BPLP-PSer/HA group at the margin of defects, resulting in decreased defect sizes compared to POC/HA and PLGA/HA (FIGS. 15A&6A). Additionally, growth of bone islands could be observed within the defects of both BPLP-PSer/HA and POC/HA groups, while very few isolated bone islands formed in the PLGA/HA group. Of note, new bone formation was enhanced on BPLP-PSer/HA MPs compared to on POC/HA in island size and number, which was confirmed by quantitative bone mineral density (BMD) analysis (FIG. 15A)

Figure 15B:
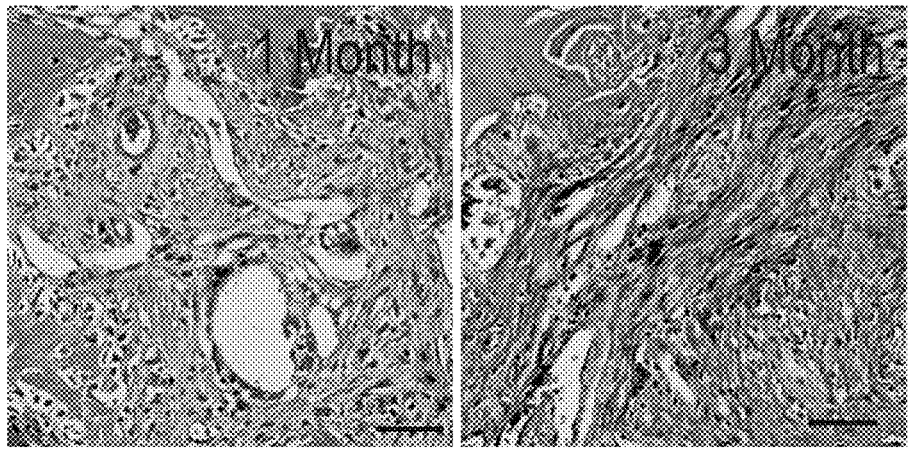
Figure 15C:
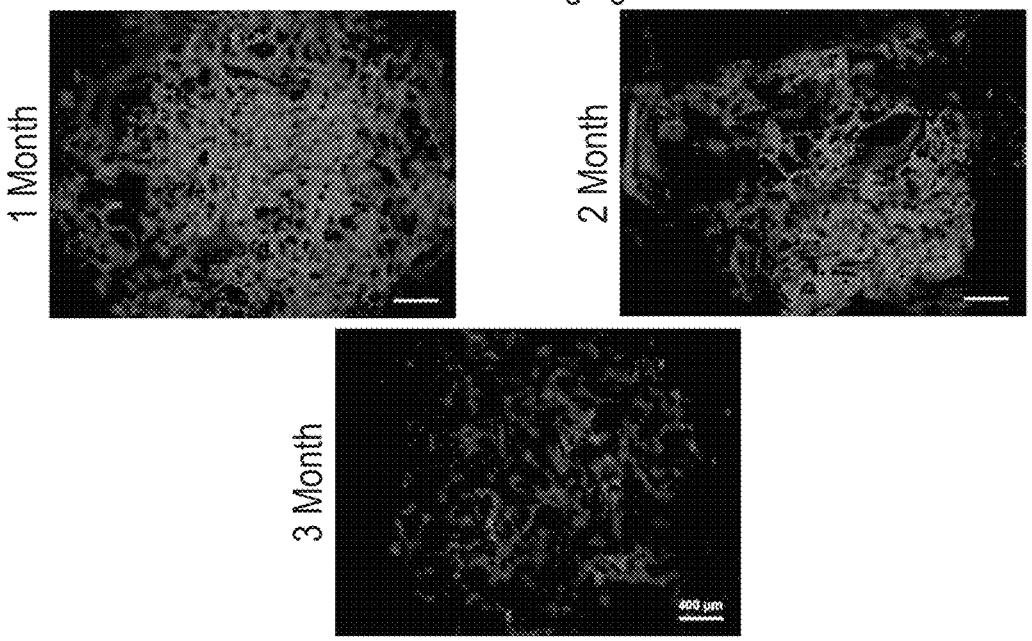

H&E staining further revealed that at 1 month, new bone began to be directly deposited onto BPLP-PSer/HA MPs, while minimal bone formation was visible on other groups (FIG. 6B). With longer implantation, enough bone filled the intraparticulate and interparticulate spaces in BPLP-PSer/HA and POC/HA groups bridging adjacent MPs. In contrast, in the PLGA/HA group, fibrous tissue was found between the newly formed bone and the remnant materials, likely due to rapid degradation of the implant, while in the negative control group, only fibrous tissue was observed (FIG. 15B). Masson's trichrome staining showed substantially more matured bone in the BPLP-PSer/HA group, which was gathered along the MP material surface and extending outward, compared to that in the POC/HA and PLGA-HA groups. Moreover, fluorescence emitted from BPLP-PSer/HA MPs in tissue sections provided strong contrast between the MPs and surrounding tissue (FIG. 15C), enabling a facile method for analyzing the remaining materials once implanted for predetermined time. Densitometry showed a decrease in MP section surface areas with the healing time, especially after 2 month of implantation, coinciding with the total remained fluorescence profile (FIG. 6C).

BPLP-PSer/HA MPs Efficacy in Critical-Sized Cranial Defect Model

The results above demonstrated that BPLP-PSer/HA MPs can elicit faster bone formation and maturation in the femoral condyle defect model, such that the MPs can bridge nonunion defects of endochondral origin even in the absence of exogenous cell sources and growth. Still, defect size and location are major determinants that affect the innate capability for bone healing. In particular, the craniofacial bone of intramembraneous origin suffers from reduced healing responses due to poor blood supply and relative deficiency of bone marrow sources. A second in vivo study was performed to evaluate the potential application of BPLP-PSer/HA MPs in rat critical-sized full-thickness cranial defects, considered a severe test for bone implants.

Figure 16A:
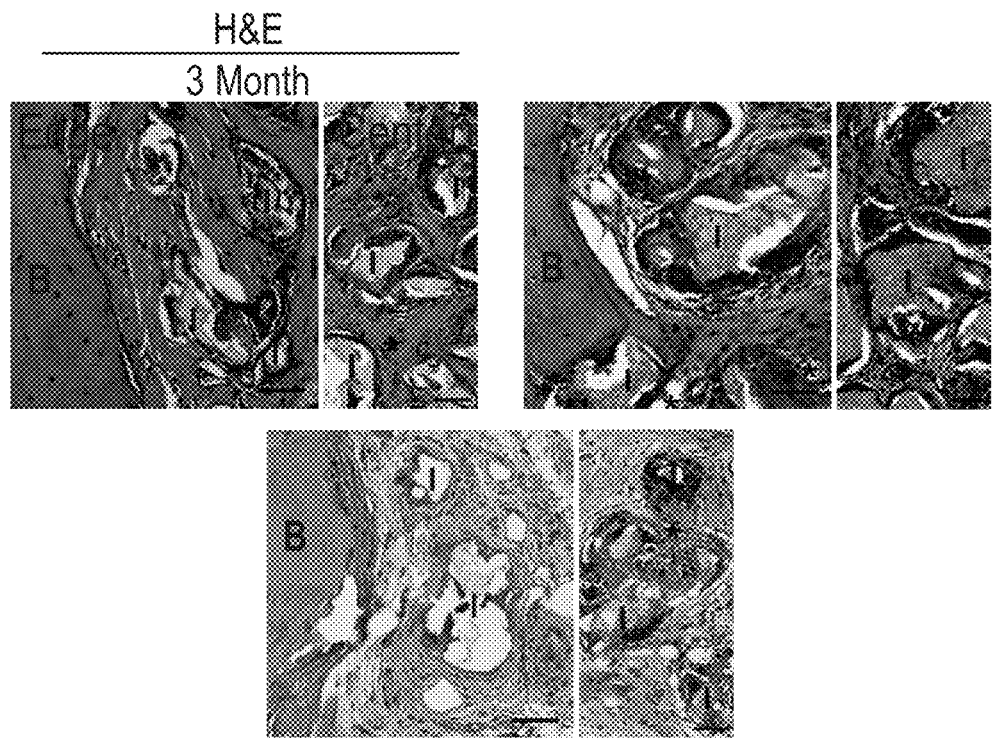
FIGS. 16A-16C are images showing in vivo results in cranial defects. (A) H&E staining of cranial defects treated with different Mps. Scale bars, 50 µm. I indicates implants. B indicates bony front, * indicates new blood vessel. (B) H&E staining of cranial defects in the Control group with no MP scaffolds implanted (Scale bars, 50 µm). (C) H&E staining of cranial defects treated with BPLP-PSer/HA Mps with blood vessels infiltrated. Scale bars, 50 µm, I indicates implants, B indicates bony front, * indicates new blood vessel.
Figure 16B:
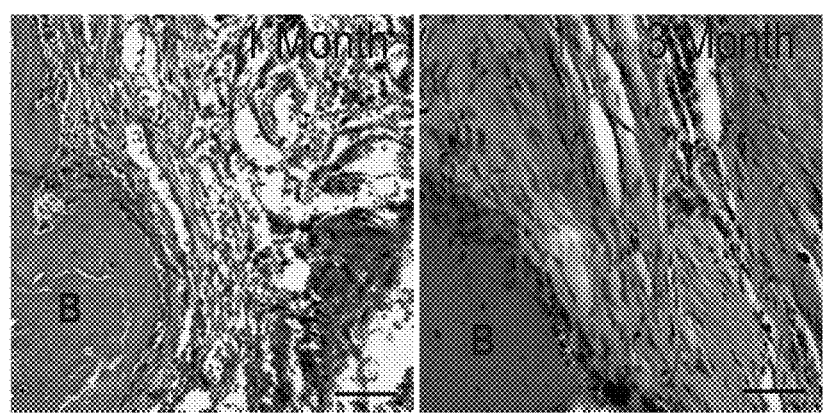
Figure 16C:
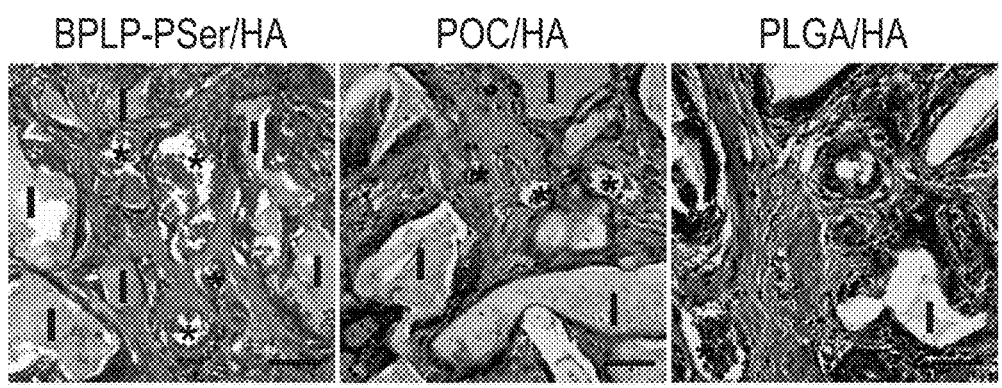

MicroCT images revealed that implantation of BPLP-PSer/HA MPs resulted in a significant reduction of the defective gap, which bridged over partial length of defect (relatively good bridging and fast healing), whereas POC/HA and PLGA/HA MPs mostly bridged at the defect margins (FIG. 6D). Quantitative analysis of BMD further confirmed the superior in-vivo performance of BPLP-PSer/HA over other groups. Meanwhile, histomorphometric analysis at 3 months revealed more woven bone (FIG. 16A) and increased red stained mature bone generated in the BPLP-PSer/HA group than that formed in other groups (FIG. 6E). In contrast, the negative control defects were filled with loose fibrous connective tissue (FIG. 16B). More new blood vessels were found in the BPLP-PSer/HA group with the presence of red blood cells (FIGS. 16C&6E), indicating their functional connection to the surrounding circulation. Immunohistochemical staining consistently revealed a remarkably higher VEGF expression in peri-implant cells on BPLP-PSer/HA MPs as compared to MPs control groups (FIG. 6E), suggesting higher blood vessel forming activity, since VEGF producing cells in bone could largely stimulate the formation of new blood vessels. Also, OCN staining revealed a prominently higher bone matrix formation activity of peri-implant cells around BPLP-PSer/HA MPs. Collectively, both femoral condyle and cranial defect models confirmed that BPLP-PSer/HA MPs elicited faster and superior bone formation and osteointegration in defects, such that new bone formation and maturation was found conducting along the material surface, indicating the extensive influence of the concerted action of citrate and PSer in fueling bone regeneration.

The present study has identified citrate as an osteo-promotive factor, and specifically its beneficial effects are mediated by SLC13a5, the plasma membrane transporter responsible for citrate uptake. Here, a previously unexplored central link in which uptaken citrate mediates metabolic regulation of cellular energy status that influences the osteo-phenotype progression of hMSCs, referred to as metabonegenic regulation, has been identified as a central mechanism underlying citrate-promoted osteo-differentiation.

The findings herein support the involvement of SLC13a5 in the beneficial effects of citrate. The expression of SLC13a5 in hMSCs was demonstrated for the first time, further showing that citrate-elevated ALP expression was affected by SLC13a5. These findings have significant implications in bone stem cell biology, providing a biological mechanism behind the reported contribution of exogenous citrate in the development and function of teeth and bone. These studies demonstrated that inhibition of SLC13a5 in hMSCs can negate the citrate-mediated metabolic changes such as ATP production, highlighting the metabolic impact of citrate towards bone growth.

The expression pattern of SLC13a5 matched the stage-dependent effects of citrate supplementation (FIG. 3B), suggesting that hMSCs exhibit higher demand for exogenous citrate during pre- and early-stage differentiation (toward Runx2 expression, protein synthesis, etc.) when their primary energy production is via glycolysis, typically, without the production of endogenous citrate in large amount.

The foregoing contributes to a comprehensive understanding of the temporal dependence of exogenous citrate in coordinated bone formation, and also can help facilitate design (or even improvement) of citrate metabonegenic regulation. For example, the present study showed that the introduction of PSer as a natural organic phosphate donor uniquely complemented the citrate metabonegenic effect, resulting in elevated intracellular ATP levels particularly in the later stages of hMSC differentiation to prolong active osteogenesis. Consistently, BPLP-PSer also induced elevated ALP production in late-stage differentiating hMSCs, likely due to bioactive inorganic phosphates generated by both the incorporated PSer in the polymer (FIG. 9E) and the soluble PSer released during degradation (FIG. 9D).

In addition to the studies above, the BPLP-PSer/HA composite MP scaffolds provided growth guidance and osteogenic benefits for accelerated bone repair. As an exemplified scaffold modality, MP scaffolds provide abundant bioactive surfaces for cell interactions, along with well-interconnected pores for fast tissue penetration, enabling in vitro 3D culture studies and facile in vivo applications for bone defect filling or augmentation. The incorporation of citrate greatly boosted cellular energy levels (FIG. 5B), while further introduction of PSer led to sustained osteogenic activity of the surrounding osteoblasts (FIGS. 5C&5D). This is in accordance with in vivo results showing that significantly more new and mature bone was formed by peri-implant cells around the BPLP-PSer/HA implants in both animal models of different origin. Of note, VEGF expression was highest on peri-implant cells surrounding the BPLP-PSer/HA implants, accompanied by greater numbers of new blood vessels.

This disclosure provides a new understanding of the citrate effect on osteo-phenotype progression, revealing a previously unexplored expression pattern of SLC13a5 citrate transporter along osteo-differentiation, and a mechanism focusing on the metabolic regulation of citrate to elevate cell energy status for bone formation, referred to as citrate metabonegenic regulation. These findings not only identify citrate as a new metabolic factor in the stem cell micro-environment favorable for osteo-differentiation, but also indicate that citrate can be used in bone biomaterials design, providing design guidance for orthopedic biomaterials for enhanced bone regeneration. These understandings were translated in a design of novel citrate-phosphate presenting materials BPLP-PSer/HA for orthopedic applications, based on the newly identified concerted action of citrate and PSer for prolonged citrate metabonegenic effect well into late stage of differentiation, which demonstrated therapeutic potential for bone injuries, particularly for bone defect filling or augmentation. In addition, BPLP-PSer represents a singular base material that can be readily tuned to match the temporal needs of osteopromotive factors at different stages of bone healing, either by selecting material degradation for soluble citrate/PSer release, or by incorporation of other micro-environment factors (e.g., cells, biochemical or biophysical factors) that can coordinate with citrate metabonegenic regulation to amplify bone regrowth.

The invention claimed is:

1. A composition comprising a polymer or oligomer formed from one or more monomers of Formula (A1), optionally one or more monomers of Formula (A2), one or more monomers of Formula (B1), (B2), or (B3), and one or more monomers of Formula (J), wherein the one or more monomers of Formula (J) comprise a phospho-amino acid:

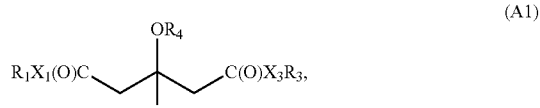

(A1)

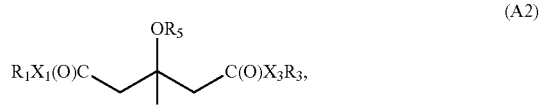

(A2)

(B1)

(B2)

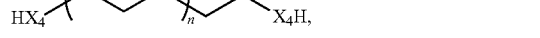

(B3)

wherein $X_1$, $X_2$, $X_3$, and $X_4$ are each independently —O— or —NH—;

$R_1$, $R_2$, and $R_3$ are each, independently, —H or a C1 to C22 alkyl or alkenyl or $M^+$, $R_4$ is H;

$R_5$ is $C(O)R_{23}$;

$R_6$ is —H, —NH$_2$, —OH, —OCH$_3$, —OCH$_2$CH$_3$, —CH$_3$, or —CH$_2$CH$_3$;

$R_7$ is —H or C1 to C23 alkyl or alkenyl group-CH$_3$;

$R_8$ is —H, a C3 to C22 alkyl or alkenyl group, —CH$_2$CH$_2$OH, or —CH$_2$CH$_2$NH$_2$;

$R_{23}$ is a C14 to C22 alkyl or alkenyl group; and n and m are independently integers ranging from 1 to 20.

2. The composition of claim 1, wherein the polymer or oligomer is formed from one or more monomers of Formula (A1), optionally one or more monomers of Formula (A2), one or more monomers of Formula (B1), (B2), or (B3), one or more monomers of Formula (J), and one or more monomers of Formula (C), Formula (D1), Formula (D2), Formula (D3), Formula (D4), Formula (E1), Formula (E2), Formula (F), Formula (G), Formula (H1), Formula (H2), Formula (H3), Formula (I1), Formula (I2), Formula (I3), Formula (I4), Formula (I5), and/or Formula (I6):

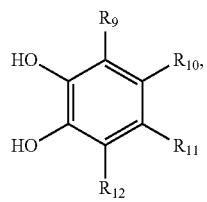

(C)

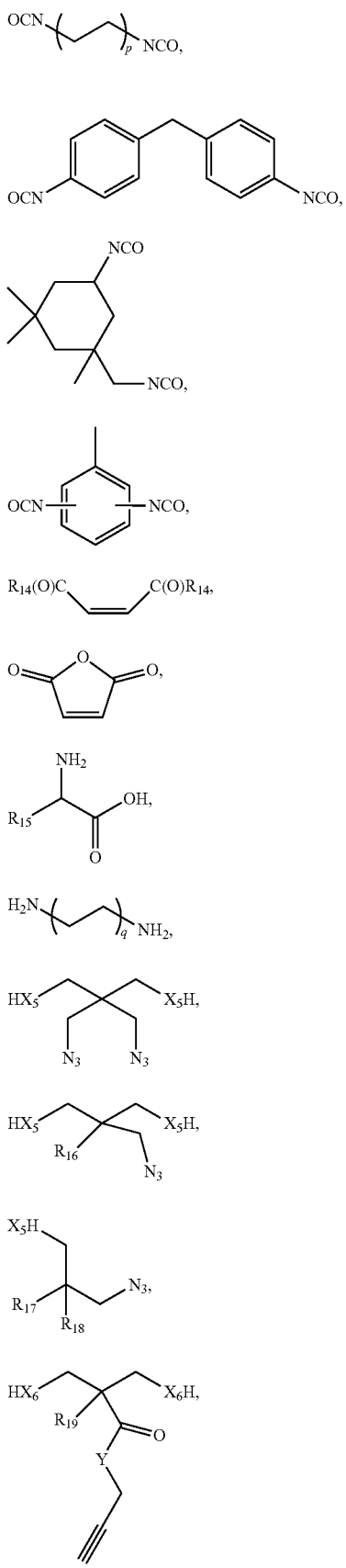

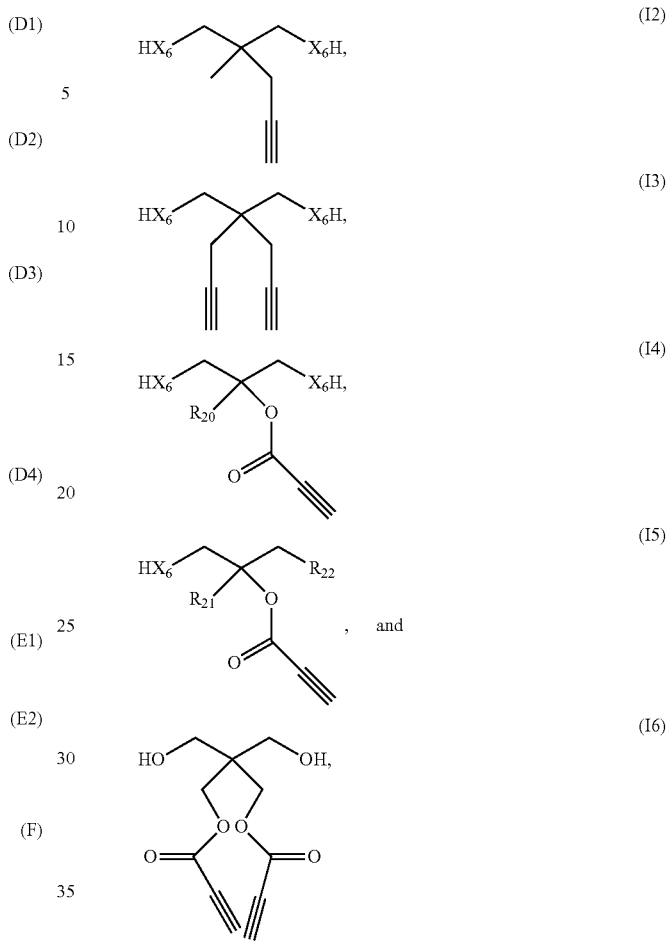

Wherein $R_9$, $R_{10}$, $R_{11}$ and $R_{12}$ are each independently —H, —OH, —CH$_2$(CH$_2$)$_x$NH$_2$, —CH$_2$(CHR$_{13}$)NH$_2$, —CH$_2$(CH$_2$)$_x$OH, —CH$_2$(CHR$_{13}$)OH, or —CH$_2$(CH$_2$)$_x$COOH;

$R_{13}$ is —COOH or —(CH$_2$)$_y$COOH;

x is an integer ranging from 0 to 10;

y is an integer ranging from 1 to 10;

p is an integer ranging from 1 to 10;

$R_{14}$ is —OH, —OCH$_3$, —OCH$_2$CH$_3$, or —Cl;

$R_{15}$ is an amino acid side chain;

q is an integer ranging from 1 to 20;

$X_5$ is —O— or —NH—;

$R_{16}$ is —CH$_3$ or —CH$_2$CH$_3$;

$R_{17}$ and $R_{18}$ are each independently —CH$_2$NH$_3$, —CH$_3$, or —CH$_2$CH$_3$;

$X_6$ and Y are each independently —O— or —NH—;

$R_{19}$ and $R_{20}$ are each independently —CH$_3$ or —CH$_2$CH$_3$;

$R_{21}$ is —O(CO)C≡CH, —CH$_3$, or —CH$_2$CH$_3$; and $R_{22}$ is —CH$_3$, —OH, or —NH$_2$.

3. The composition of claim 1, wherein the molar ratio of the one or more monomers of Formula (A1) and Formula (A2) to the one or more monomers of Formula (B1), Formula (B2), or Formula (B3) is between about 1:10 and about 10:1.

4. The composition of claim 3, wherein the molar ratio of the one or more monomers of Formula (A1) and Formula (A2) to the one or more monomers of Formula (B1), Formula (B2), or Formula (B3) is about 5:6.

5. The composition of claim 1, wherein the molar ratio of the one or more monomers of Formula (B1), Formula (B2), or Formula (B3) to the one or more monomers of Formula (J) is between about 1:20 to about 20:1.

6. The composition of claim 5, wherein the molar ratio of the one or more monomers of Formula (B1), Formula (B2), or Formula (B3) to the one or more monomers of Formula (J) is about 6:1.

7. The composition of claim 1, wherein the molar ratio of the one or more monomers of Formula (A1) and Formula (A2) to the one or more monomers of Formula (J) is between about 1:20 to about 20:1.

8. The composition of claim 7, wherein the molar ratio of the one or more monomers of Formula (A1) and Formula (A2) to the one or more monomers of Formula (J) is about 5:1.

9. The composition of claim 1, wherein the polymer or oligomer is formed from one or more monomers of Formula (A1), one or more monomers of Formula (B2), and one or more monomers of Formula (J).

10. The composition of claim 1, wherein the one or more monomers of Formula (A1) comprises citric acid.

11. The composition of claim 1, wherein the one or more monomers of Formula (B2) comprises 1,8-octanediol.

12. The composition of claim 1, wherein the one or more monomers of Formula (J) comprises O-phospho-D,L-serine.

13. The composition of claim 12, wherein the one or more monomers of Formula (A1) comprises citric acid.

14. The composition of claim 13, wherein the one or more monomers of Formula (B2) comprises 1,8-octanediol.

15. The composition of claim 1, wherein $X_1$, $X_2$, and $X_3$ are each —O—.

16. The composition of claim 15, wherein $R_1$, $R_2$, and $R_3$ are each —H.

17. The composition of claim 16, wherein n is between 6 and 8.

18. The composition of claim 17, wherein the polymer or oligomer is formed from citric acid, 1,8-octanediol, and O-phospho-D,L-serine.

* * * * *